US011096934B2

(12) United States Patent
Sykes et al.

(10) Patent No.: US 11,096,934 B2
(45) Date of Patent: Aug. 24, 2021

(54) COMPOUNDS AND METHODS USEFUL FOR TREATING OR PREVENTING HEMATOLOGICAL CANCERS

(71) Applicants: THE BROAD INSTITUTE, INC., Cambridge, MA (US); THE GENERAL HOSPITAL CORPORATION, Boston, MA (US); PRESIDENT AND FELLOWS OF HARVARD COLLEGE, Cambridge, MA (US); BAYER PHARMA AKTIENGESELLSCHAFT, Berlin (DE)

(72) Inventors: David B. Sykes, Boston, MA (US); David Scadden, Boston, MA (US); Timothy A. Lewis, Cambridge, MA (US); Andreas Janzer, Berlin (DE); Hanna Meyer, Berlin (DE); Detlef Stöckigt, Potsdam (DE)

(73) Assignees: THE BROAD INSTITUTE, INC., Cambridge, MA (US); THE GENERAL HOSPITAL CORPORATION, Boston, MA (US); PRESIDENT AND FELLOWS OF HARVARD COLLEGE, Cambridge, MA (US); BAYER PHARMA AKTIENGESELLSCHAFT, Berlin (DE)

( * ) Notice: Subject to any disclaimer, the term of this patent is extended or adjusted under 35 U.S.C. 154(b) by 49 days.

(21) Appl. No.: 15/756,469

(22) PCT Filed: Aug. 29, 2016

(86) PCT No.: PCT/EP2016/070320
§ 371 (c)(1),
(2) Date: Feb. 28, 2018

(87) PCT Pub. No.: WO2017/037022
PCT Pub. Date: Mar. 9, 2017

(65) Prior Publication Data
US 2018/0263970 A1 Sep. 20, 2018

Related U.S. Application Data

(60) Provisional application No. 62/329,796, filed on Apr. 29, 2016, provisional application No. 62/212,992, filed on Sep. 1, 2015.

(51) Int. Cl.
| | | |
|---|---|---|
| *A61K 31/47* | (2006.01) | |
| *A61P 35/02* | (2006.01) | |
| *A61K 31/277* | (2006.01) | |
| *A61K 33/36* | (2006.01) | |
| *A61K 31/42* | (2006.01) | |
| *A61K 31/505* | (2006.01) | |
| *A61K 31/27* | (2006.01) | |

(52) U.S. Cl.
CPC ............ *A61K 31/47* (2013.01); *A61K 31/27* (2013.01); *A61K 31/277* (2013.01); *A61K 31/42* (2013.01); *A61K 31/505* (2013.01); *A61K 33/36* (2013.01); *A61P 35/02* (2018.01)

(58) Field of Classification Search
None
See application file for complete search history.

(56) References Cited

U.S. PATENT DOCUMENTS

| | | | | |
|---|---|---|---|---|
| 5,886,033 A | * | 3/1999 | Schwab | A61K 31/275 514/521 |
| 2013/0109644 A1 | * | 5/2013 | MacBeth | A61K 45/06 514/43 |

FOREIGN PATENT DOCUMENTS

| | | | |
|---|---|---|---|
| CN | 104666272 A | 6/2015 | |
| WO | 98/13047 A1 | 4/1998 | |
| WO | WO-9813047 A1 * | 4/1998 | ............ A61K 45/06 |
| WO | 2011032929 A1 | 3/2011 | |

OTHER PUBLICATIONS

Schwartsmann et al.; "DUP 785 (NCS 3683902): Schedule-Dependency of Growth-Inhibitory and Antipyrimidine effects." 1988, PERGAMON; Biochemical Pharmacology, vol. 37, No. 17, pp. 3257-3266. (Year: 1988).*
Ringhauser et al.; "The immunomodulatory drug Leflunomide inhibits cell cycle progression of B-CLL cellls," 2007, Nature Publishing Group, Leukemia, vol. 22, No. 3, pp. 635-638. (Year: 2007).*
Goussetis et al.; "Autophagy Is a Critical Mechanism for the Induction of the Antileukemic Effects of Arsenic Trioxide," ASBMB; Journal of Biological Chemistry, vol. 285, No. 39, p. 29989-29997. (Year: 2010).*
Schwartsmann, G. et al., "DUP 785 (NSC 368390): Schedule-dependency of growth-inhibitory and antipyrimidine effects", Biochemical Pharmacology, ELSEVIER, US, vol. 37, No. 17, Sep. 1, 1988, pp. 3257-3266.
Ringshausen, I. et al., "The immunomodulatory drug Leflunomide inhibits cell cycle progression of B-CLL cells," Leukemia, vol. 22, No. 3, Sep. 6, 2007, pp. 635-638.
International Search Report and Written Opinion for corresponding PCT Application No. PCT/EP2016/070320, dated Nov. 18, 2016 (8 pages).
Unknown Author, "The drug teriflunomide for the treatment of multiple sclerosis," Progress in Pharmaceutical Sciences, 2011, vol. 35, No. 1, pp. 42-44 (Translation).

(Continued)

*Primary Examiner* — David J Blanchard
*Assistant Examiner* — Ivan A Greene
(74) *Attorney, Agent, or Firm* — Greenberg Traurig, LLP; Melissa Hunter-Ensor; Scott Goncher

(57) ABSTRACT

The present invention includes methods of treating patients with acute myeloid leukemia across a range of genetic subtypes with DHODH inhibitors, such as 6-fluoro-2-(2'-fluoro-[1,1'-biphenyl]-4-yl)-3-methylquinoline-4-carboxylic acid).

10 Claims, 33 Drawing Sheets

(56) References Cited

OTHER PUBLICATIONS

Dietrich et al., "Leflunomide Induces Apoptosis in Fludarabine-Resistant and Clinically Refractory CLL Cells," Clinical Cancer Research, Jan. 15, 2012, vol. 18, No. 2, pp. 417-431.
Unknown Author, "The drug teriflunomide for the treatment of multiple sclerosis," Progress in Pharmaceutical Sciences, 2011, vol. 35, No. 1, pp. 42-44.

* cited by examiner

Fig. 1H (SUPPL S1)

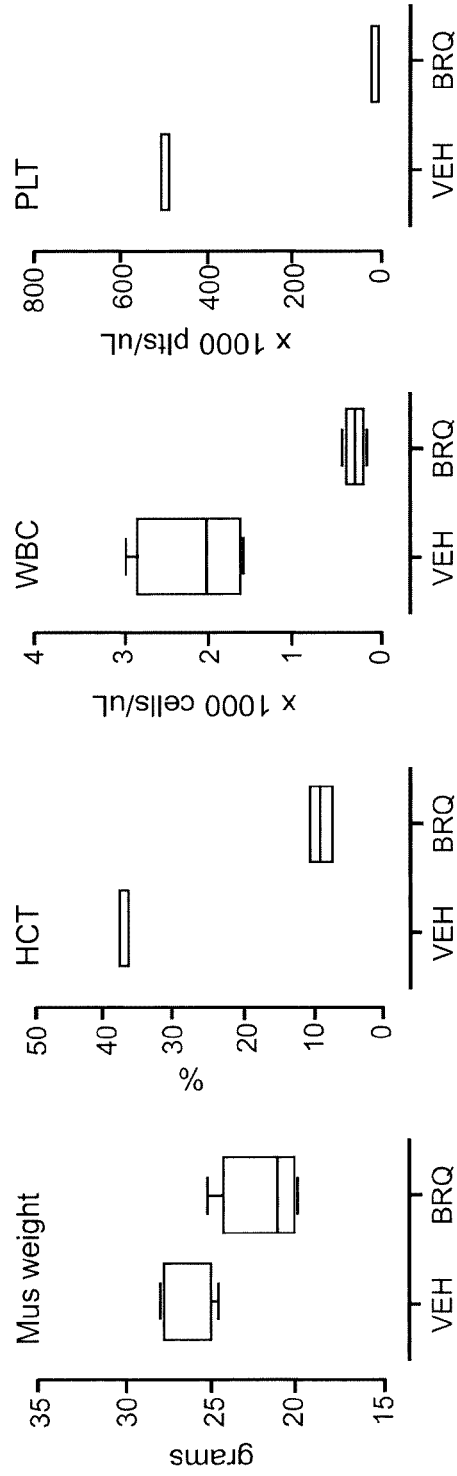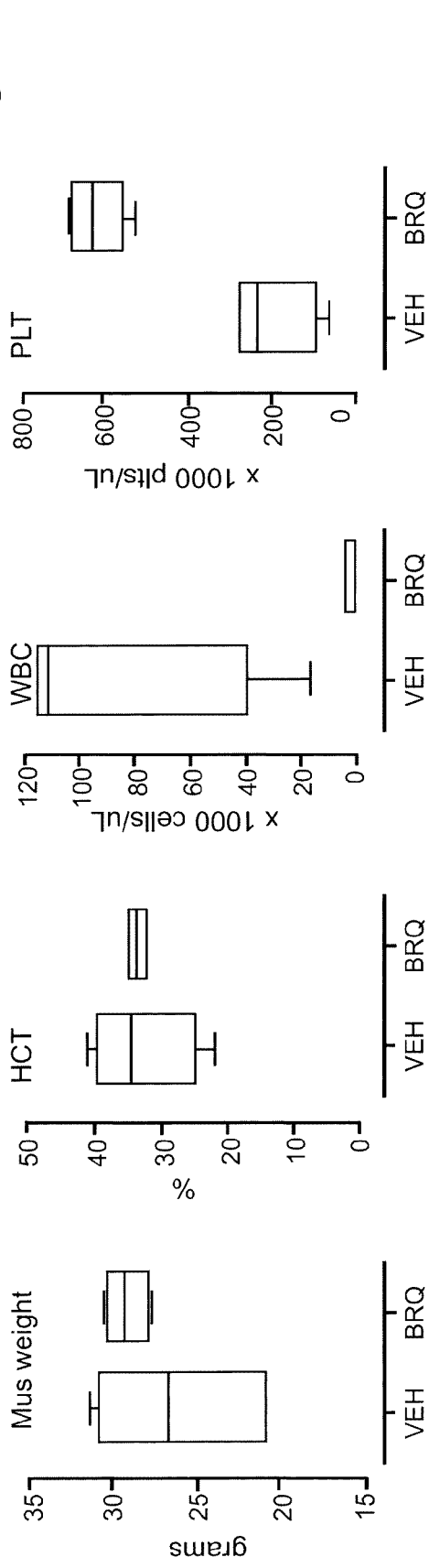
Fig. 6E
Fig. 6F

COMPOUNDS AND METHODS USEFUL FOR TREATING OR PREVENTING HEMATOLOGICAL CANCERS

CROSS-REFERENCE TO RELATED APPLICATIONS

This application is the U.S. national phase application, pursuant to 35 U.S.C. § 371, of PCT International Application Serial No.: PCT/EP2016/070320, filed Aug. 29, 2016, designating the United States and published in English which claims the benefit of the following U.S. Provisional Application Nos. 62/212,992, filed Sep. 1, 2015 and 62/329,796, filed Apr. 29, 2016, the entirety which are herein incorporated by reference.

STATEMENT OF RIGHTS TO INVENTIONS MADE UNDER FEDERALLY SPONSORED RESEARCH

This invention was made with government support under Grant No. DA032471 awarded by the National Institutes of Health. The government has certain rights in the invention.

BACKGROUND OF THE INVENTION

Acute myeloid leukemia (AML), also known as acute myelogenous leukemia or acute non-lymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease (accounting for approximately 1.2% of cancer deaths in the U.S.) its incidence is expected to increase as the population ages.

The symptoms of AML are caused by replacement of normal bone marrow with leukemic cells, which causes a drop in red blood cells, platelets and normal white blood cells. These symptoms include fatigue, shortness of breath, easy bruising and bleeding, and increased risk of infection. Several risk factors and chromosomal abnormalities have been identified, but the specific cause of AML is unclear at this time. As an acute leukemia, AML progresses rapidly and is typically fatal within weeks or months if left untreated.

AML has several subtypes, and treatment and prognosis varies among subtypes. Five-year survival rate is only 25%, and relapse rate varies from 33-78%, depending on subtype. AML is treated initially with chemotherapy aimed at inducing a remission, and patients may go on to receive additional chemotherapy or a hematopoietic stem cell transplant.

The standard of care chemotherapy is a combination of cytarabine and an anthracycline which has remained unchanged in the last 40 years. This in view of the 25% survival rate mentioned above clearly indicates the need for new therapies.

One approach for a 10% subset of patients diagnosed with acute promyelocytic leukemia (APL) has achieved limited success in AML comprising treating the subject with small molecules, such as all-trans retinoic acid (ATRA) and arsenic trioxide, that trigger the differentiation of the leukemic AML cells. ATRA and arsenic trioxide overcome the differentiation arrest imposed by the retinoic acid receptor alpha (RARα) fusion oncoprotein, and treated leukemic promyelocytes terminally differentiate to mature neutrophils. These small molecules are remarkably well-tolerated by patients in comparison to traditional cytotoxic chemotherapy. Furthermore, incorporating ATRA into treatment regimens single-handedly improved the overall survival of patients with acute promyelocytic leukemia (APL) from 20% to 75%. Unfortunately, differentiation therapy does not exist for the much larger fraction of non-APL acute myeloid leukemias, where the standard of care results in an overall survival rate of only 25%.

The mammalian homeobox transcription factors contribute to lineage-specific hematopoietic differentiation, and their expression is tightly regulated during normal hematopoiesis. More specifically, HoxA9 has an important role in normal hematopoiesis and leukemogenesis. Though critical to early hematopoiesis, the expression of the HoxA cluster of genes is normally downregulated as cells mature. The persistent, and inappropriate, expression of members of the HoxA cluster of genes takes place in the majority of acute myeloid leukemias. HoxA9 is directly involved in human leukemias as one partner of the fusion protein NUP98-HoxA9. In analyses of human AML, the level of HoxA9 expression correlates with poor prognostic karyotype and inversely correlated with survival. Furthermore, in patients with CML, a relatively higher level of HoxA9 expression is associated with transition from chronic phase to accelerated and blast phase. HoxA9 is critical to the small subset of lymphoid and myeloid leukemias that express fusion oncoproteins involving the mixed lineage leukemia (MLL) gene. Leukemias harboring MLL-rearrangements are a particularly poor prognosis subgroup of AML and depend on HoxA9 for proliferation and survival. Overall, this suggests that HoxA9 dysregulation, through fusion with NUP98 and/or inappropriate maintenance of HoxA9 expression, is a common mechanism in the differentiation arrest in myeloid leukemia.

There is a need in the art to identify compounds that can be used to treat or prevent a hematological cancer, such as but not limited to acute myeloid leukemia (AML), acute promyelocytic leukemia (APL), myelodysplastic syndrome (MDS), mixed-lineage leukemia (MLL), and/or chronic myeloid leukemia (CML), in a subject in need thereof. The present invention meets this need.

SUMMARY OF THE INVENTION

As described below, the present invention generally provides compounds that can be used to treat or prevent certain types of hematological cancer in a subject in need thereof. In certain embodiments, the compounds of the invention overcome differentiation arrest in a subject afflicted by a hematological cancer.

The invention provides a method of treating or preventing a hematological cancer in a subject in need thereof, the method comprising administering to the subject a therapeutically effective amount of brequinar, or a salt or solvate thereof, wherein brequinar is administered to the subject with a frequency less than or equal to once every 48 hours.

The invention further provides a method of depleting or promoting differentiation of leukemia initiating cells in a subject in need thereof, the method comprising administering to the subject a therapeutically effective amount of brequinar, or a salt or solvate thereof, wherein brequinar is administered with a frequency equal to or less than once every 48 hours.

In certain embodiments, brequinar is administered to the subject with a frequency less than or equal to once every 72 hours.

In certain embodiments, brequinar is administered to the subject with a frequency equal to once every 72 hours.

In certain embodiments, the hematological cancer is characterized by differentiation arrest. In other embodiments, the subject has been treated or is being treated for a hematological cancer characterized by differentiation arrest.

In certain embodiments, the hematological cancer comprises acute myeloid leukemia (AML), acute promyelocytic leukemia (APL), mixed-lineage leukemia (MLL), myelodysplastic syndrome (MDS), and/or chronic myeloid leukemia (CML).

In certain embodiments, the hematological cancer comprises AML.

In certain embodiments, brequinar is administered to the subject by at least one route selected from oral, rectal, mucosal, transmucosal, topical, intravenous, intradermal, intramuscular, subcutaneous, intracutaneous, intrauterine, epidural and intracerebroventricular injections.

In certain embodiments, to the subject is further administered at least one additional agent useful for treating or preventing a hematological cancer.

In certain embodiments, the agent comprises ATRA or arsenic trioxide.

In certain embodiments, the compound and the agent are coformulated.

In certain embodiments, the subject is a mammal. In other embodiments, the mammal is human.

In certain embodiments, the subject is not responsive to one or more anticancer agents.

In one aspect, the invention provides use of a dihydroorotate inhibitor in a method of treating or preventing a hematological cancer in a subject in need thereof. The method involves administering to the subject a therapeutically effective amount of a dihydroorotate dehydrogenase (DHODH) inhibitor, or a salt or solvate thereof, wherein the dihydroorotate inhibitor selected from the group consisting of 6-fluoro-2-(2'-fluoro-[1,1'-biphenyl]-4-yl)-3-methylquinoline-4-carboxylic acid) (brequinar); 5-methyl-N-[4-(trifluoromethyl) phenyl]-isoxazole-4-carboxamide); (2Z)-2-cyano-3-hydroxy-N-[4-(trifluoromethyl)phenyl]but-2-enamide) or any combinations thereof or a salt or solvate thereof is administered to the subject with a frequency less than or equal to once every 72 hours.

In particular embodiments, 6-fluoro-2-(2'-fluoro-[1,1'-biphenyl]-4-yl)-3-methylquinoline-4-carboxylic acid) or a salt or solvate thereof is administered to the subject with a frequency less than or equal to once every 72 hours or with a frequency less than or equal to once every 48 hours.

In various embodiments of any aspect delineated herein, the hematological cancer includes acute myeloid leukemia (AML), acute promyelocytic leukemia (APL), mixed-lineage leukemia (MLL), myelodysplastic syndrome (MDS), and/or chronic myeloid leukemia (CML). In certain embodiments, the hematological cancer includes AML.

In various embodiments of any aspect delineated herein, the subject is a mammal. In certain embodiments, the mammal is human. In various embodiments of any aspect delineated herein, the subject has been treated or is being treated for a hematological cancer characterized by differentiation arrest. In various embodiments, the subject is not responsive to one or more anticancer agents.

In various embodiments of any aspect delineated herein, 6-fluoro-2-(2'-fluoro-[1,1'-biphenyl]-4-yl)-3-methylquinoline-4-carboxylic acid) is administered to the subject by at least one route selected from oral, rectal, mucosal, transmucosal, topical, intravenous, intradermal, intramuscular, subcutaneous, intracutaneous, intrauterine, epidural and intracerebroventricular injections.

In various embodiments of any aspect delineated herein, at least one additional agent useful for treating or preventing a hematological cancer (e.g., arsenic trioxide and/or ATRA) is further administered to the subject.

In various embodiments of any aspect delineated herein, the method involves administering to the subject a composition comprising a dihydroorotate dehydrogenase (DHODH) inhibitor (e.g., 6-fluoro-2-(2'-fluoro-[1,1'-biphenyl]-4-yl)-3-methylquinoline-4-carboxylic acid (brequinar) or a salt or solvate thereof) in an amount and for a duration sufficient to increase levels of dihydroorotate and/or to reduce levels of uridine in a biological sample obtained from the subject, thereby treating the hematological cancer.

In various embodiments of any aspect delineated herein, the method involves administering to the subject a first dose of a DHODH inhibitor (e.g., 6-fluoro-2-(2'-fluoro-[1,1'-biphenyl]-4-yl)-3-methylquinoline-4-carboxylic acid (brequinar) or a salt or solvate thereof); detecting dihydroorotate and/or uridine in a biological sample obtained from the subject; and administering a second dose of a DHODH inhibitor (e.g., 6-fluoro-2-(2'-fluoro-[1,1'-biphenyl]-4-yl)-3-methylquinoline-4-carboxylic acid (brequinar) or a salt or solvate thereof), where the amount and or timing of the administration is modified based on the amounts of dihydroorotate (DHO) and/or uridine detected, thereby treating the hematological malignancy in the subject.

In various embodiments of any aspect delineated herein, the amount and/or timing of DHODH inhibitor administration is sufficient to increase levels of dihydroorotate by at least about 100-500 fold.

In various embodiments of any aspect delineated herein, the second dose of DHODH inhibitor (e.g., 6-fluoro-2-(2'-fluoro-[1,1'-biphenyl]-4-yl)-3-methylquinoline-4-carboxylic acid (brequinar) or a salt or solvate thereof) is administered after the amount of DHO has returned to baseline. In certain embodiments, the second dose is administered when the amount of uridine is 10-25% greater than the level of uridine present 12 hours after administration of the first dose.

The invention provides compounds with anticancer activity, compositions comprising the same, and methods of treating or preventing certain types of hematological cancer, such as AML. Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well known and commonly employed in the art.

As used herein, the articles "a" and "an" refer to one or to more than one (i.e., to at least one) of the grammatical object of the article. By way of example, "an element" means one element or more than one element.

As used herein, the tet in "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "administration" means providing the composition of the present invention to a subject by any suitable method.

As used herein, the term "alkenyl" employed alone or in combination with other terms means, unless otherwise stated, a stable mono-unsaturated or di-unsaturated straight chain or branched chain hydrocarbon group having the stated number of carbon atoms. Examples include vinyl, 1-propenyl, 2-propenyl (allyl), 2-butenyl (crotyl), isopentenyl, butadienyl, 1,3-pentadienyl, 1,4-pentadienyl, and the higher homologs and isomers. A functional group representing an alkene is exemplified by —CH$_2$—CH=CH$_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$) alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is (C$_1$-C$_6$) alkyl, such as, but not limited to, ethyl, methyl, isopropyl, isobutyl, n-pentyl, n-hexyl and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH. The term "substituted propargylic" refers to a group exemplified by —CR$_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —CR$_2$CR$_2$—C≡CR, wherein each occurrence of R is independently H, alkyl, substituted alkyl, alkenyl or substituted alkenyl, with the proviso that at least one R group is not hydrogen.

As used herein, the term "AML" refers to acute myeloid leukemia.

As used herein, the term "APL" refers to acute promyelocytic leukemia, which is also known as PML or promyelocytic leukemia.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl" or "arene" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl (including 1- and 2-naphthyl). Preferred are phenyl and naphthyl, most preferred is phenyl.

As used herein, the term "aryl-(C$_1$-C$_3$)alkyl" means a functional group wherein a one to three carbon alkylene chain is attached to an aryl group, e.g., —CH$_2$CH$_2$-phenyl or —CH$_2$-phenyl (benzyl). Preferred is aryl-CH$_2$— and aryl-CH(CH$_3$)—. The term "substituted aryl-(C$_1$-C$_3$)alkyl" means an aryl-(C$_1$-C$_3$)alkyl functional group in which the aryl group is substituted. Preferred is substituted aryl (CH$_2$)—, whereby the substitutents are selected from halogen, C$_1$-C$_3$-alkyl, C$_1$-C$_3$-alkoxy, cyano, amino. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. Preferred is substituted heteroaryl-(CH$_2$)— whereby the substitutents are selected from halogen, C$_1$-C$_3$-alkyl, C$_1$-C$_3$-alkoxy, cyano, amino.

As used herein, the term "ATRA" refers to all-trans retinoic acid, or a salt or solvate thereof.

As used herein, the term "brequinar" refers to 6-fluoro-2-(2'-fluoro-[1,1'-biphenyl]-4-yl)-3-methylquinoline-4-carboxylic acid, or a salt or solvate thereof.

In one aspect, the terms "co-administered" and "co-administration" as relating to a subject refer to administering to the subject a composition of the invention, or salt thereof, along with a composition that may also treat any of the diseases contemplated within the invention. In one embodiment, the co-administered compositions are administered separately, or in any kind of combination as part of a single therapeutic approach. The co-administered composition may be formulated in any kind of combinations as mixtures of solids and liquids under a variety of solid, gel, and liquid formulations, and as a solution.

As used herein, the term in "CML" refers to chronic myeloid leukemia.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "cycloalkyl" by itself or as part of another substituent means, unless otherwise stated, a cyclic chain hydrocarbon having the number of carbon atoms designated (i.e., C$_3$-C$_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is (C$_3$-C$_6$)cycloalkyl, such as, but not limited to, cyclopropyl, cyclobutyl, cyclopentyl and cyclohexyl.

As used herein, the term "δ" refers to delta (ppm).

As used herein, the term "DHODH" refers to dihydroorotate dehydrogenase.

By "DHODH inhibitor" is meant an agent that detectably reduces the activity of dihydroorotate dehydrogenase. In some embodiments, the reduction in DHODH activity is by at least about 10%, 20%, 30%, 40%, 50% or more. In one embodiment, DHODH activity is measured by detecting the conversion of dihydroorotate (DHO) to orotate. In one embodiment, DHODH inhibition is measured by detecting dihydroorotate (DHO). In another embodiment, DHODH activity is measured by detecting depletion of uridine.

By "disease" or "disorder" is meant any condition that damages or interferes with the normal function of a cell, tissue, or organ. In certain embodiments, the disease comprises a hematological cancer, such as acute myeloid leukemia (AML), acute promyelocytic leukemia (APL), mixed-lineage leukemia (MLL), acute lymphocytic leukemia (ALL), myelodysplastic syndrome (MDS), chronic myeloid leukemia (CML), and/or myelo-monocytic leukemia (MML).

As used herein, the term "DMSO" refers to dimethyl-sulfoxide.

By "effective amount" is meant the amount of a compound that is required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In the context of cancer, an effective amount sufficient to treat disease reduces or stabilizes neoplastic cell proliferation, reduces neoplastic cell survival, or increases neoplastic cell death.

As used herein, the term "EtOAc" refers to ethyl acetate.

As used herein, the term "halo" or "halogen" employed alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles being heteroaromatic or at least partially non aromatic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listings of heterocyclyl and heteroaryl moieties are intended to be representative and not limiting.

As used herein, the term "instructional material" includes a publication, a recording, a diagram, or any other medium of expression that may be used to communicate the usefulness of the compositions and methods of the invention. In some instances, the instructional material may be part of a kit useful for treating a hematological cancer in a subject. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

As used herein, the term "leflunomide" refers to 5-methyl-N-[4-(trifluoromethyl) phenyl]-isoxazole-4-carboxamide, or a salt or solvate thereof.

As used herein, the term "MDS" refers to myelodysplastic syndrome (MDS).

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent" or "preventing" or "prevention," as used herein, means avoiding or delaying the onset of symptoms associated with a disease or condition in a subject that has not developed such symptoms at the time the administering of an agent or compound commences. Disease, condition, and disorder are used interchangeably herein.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated within the invention, including inorganic acids, organic acids, inorganic bases, organic bases, solvates, hydrates, or clathrates thereof. As used herein, the term "salt" embraces addition salts of free acids or free bases that are compounds useful within the invention. Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl-ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "subject," "patient" or "individual" may be a human or non-human mammal or a bird. Non-human mammals include, for example, livestock and pets, such as ovine, bovine, equine, porcine, canine, feline and murine mammals. Preferably, the subject is human.

As used herein, the term "substituted" means that an atom or group of atoms has replaced hydrogen as the substituent attached to another group. Unless stated otherwise, any group recited within the invention may be substituted.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, with straight being preferred.

As used herein, the term "teriflunomide" refers to (Z)-2-cyano-3-hydroxy-N-(4-(trifluoromethyl)phenyl)but-2-enamide, or a stereoisomer, salt or solvate thereof.

The terms "treat" and "treating" and "treatment," as used herein, means reducing the frequency or severity with which symptoms of a disease or condition are experienced by a subject by virtue of administering an agent or compound to the subject.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 1A provides a FACS analysis. Primary murine bone marrow cells transduced with MSCVneo-ER-HoxA9 grow as lineage-negative cells in the presence of beta-estradiol ((+) E2; left panel). Removal of E2 (from left to right: (−) 24 hr, (−) 48 hr, (−) 72 hr, and (−) 96 hr) and inactivation of ER-HoxA9 results in the synchronous upregulation of the myeloid differentiation markers CD11b (Mac1) and Gr-1 as demonstrated by flow cytometry FIG. 1B provides panels showing flow cytometry propidium iodide analysis showing that terminal differentiation of ER-HoxA9 cells is accompanied by exit from the cell cycle (from left to right: (+) E2; (−) 24 hr, (−) 48 hr, (−) 72 hr, and (−) 96 hr).

FIG. 1C provides micrographs showing the morphologic changes that accompany myeloid differentiation are confirmed by Wright-Giemsa staining of cells in the presence (+)E2 and absence of E2 (−96 h).

FIG. 1D provides micrographs showing that terminally differentiated cells, but not undifferentiated cells, are capable of phagocytosis of fluorescently labeled *E. coli* (left: in the presence of beta-estradiol, (+) E2; right: 96 hrs. after removal of E2, (−) 96 hr.).

FIG. 1E provides a series of graphs analyzing changes in expression of the specified genes (from left to right, top to bottom: Csfra2, Cc14, Elane, Cd34, Lyz1, Cd33, Mpo, Sox4, Mmp9, Ltf, Myb, Flt3, eGFP, Itgam, Pim1, Cebpa). Lys-GFP-ER-HoxA9 cells demonstrate expected changes in gene expression upon myeloid differentiation over a 5-day time course. Their stepwise gene expression parallels the gene-expression patterns of unmanipulated murine bone marrow myeloid cells (FIG. 1F) as well as purified populations of primary human bone marrow cells (FIG. 1G).

FIG. 1F is a schematic showing a comparison time course in untreated murine bone marrow myeloid cells. This analysis illustrates a global gene expression time line, which resembles normal gene expression in bone marrow derived neutrophils.

FIG. 1H is a schematic diagram showing wild-type HoxA9 and a HoxA9 ER fusion protein comprising a G400V mutation.

FIG. 2A includes two graphs showing GFP expression analysis (left: in the presence of beta-estradiol, (+) E2; right: removal of E2, (−) E2). Following differentiation upon the removal of estradiol, Lys-GFP-ER-HoxA9 GMPs upregulate GFP fluorescence.

FIG. 2B includes two graphs showing an expression analysis of the cell-surface markers CD11b (Mac1) and Gr-1 in the cells described in FIG. 2A (left: in the presence of beta-estradiol (+) E2; right: removal of E2 (−) E2).

FIG. 2C is a schematic showing that a high-throughput flow cytometry phenotypic screen was established to identify compounds that could trigger differentiation of Lys-GFP-ER-HoxA9 cells as monitored by upregulation of GFP and CD11b.

FIG. 2D shows two of the twelve biologically active compounds identified in the screen described in FIG. 2C, including Compound 3 (C03) and Compound 7 (C07).

FIG. 2E shows the most potent small molecule was a derivative of (R)-C07, designated ML390.

FIG. 2F is a graph showing that C03 (graph with squares) and (R)-C07 triggered myeloid differentiation [%] (graph with triangles) while (S)-C07 (graph with rhombs) completely lacked activity vs log [M].

FIG. 2G is a graph showing that ML390 is capable of causing myeloid differentiation [%] in murine (ER-HoxA9 graph with dots) and human acute myeloid leukemia (AML) models (U937 graph with squares and THP1 graph with triangles).

FIG. 2H shows that imaging flow cytometry demonstrates upregulation of GFP and CD11b expression as well as the downregulation of KIT expression in Lys-GFP-ER-HoxA9 cells during differentiation in the absence of beta estradiol (−E2) or differentiation as the result of treatment with ML390 (top: in the presence of beta-estradiol, (+) E2; middle: removal of E2, (−) E2; bottom: in the presence of beta-estradiol and ML390, (+) E2+ML390).

FIG. 3A is a graph showing resistant cell line growth [log cell count] over time [days]. ER-HoxA9 and U937 cell lines resistant to C03 and (R)-C07 were generated by continuous culture in slowly increasing concentration of compound, graph of squares 10 µmol, 25 µmol, 50 µmol, DMSO, line of dots.

FIG. 3B is a diagram showing a comparison of gene expression between DMSO control and compound-resistant cells, which demonstrates that only eight overexpressed genes were shared across the four resistant cell lines.

FIG. 3C is a graph showing that eight genes consistently showed more than 8-fold upregulation and were gene neighbors on chromosome 16 (human) and chromosome 8 (mouse) shown as graph "Fold change [log 2]" vs "DMSO vs C07 in U937 cells".

FIG. 3D is a diagram illustrating that analysis of the whole-exome sequencing data revealed an increased coverage over a narrow region of chromosome 16, consistent with chromosomal amplification as the mechanism underlying increased gene expression, the diagram showing "copy number ratio" vs chromosome 16 position.

FIG. 3E is a graph showing DHODH enzyme inhibition with the specified compounds. DHODH was confirmed as the target of C03 (graph with triangles pointing down), C07((R) C07 graph with dots; (S)-C07 graph with squares), and ML390 (graph with triangles pointing up) using an in vitro enzyme inhibition assay.

FIG. 3F is a graph showing that the differentiating effects of C03 and ML390 could be abrogated by supplementation of uridine in the cell-culture media. The graph is showing "% rescue from differentiation" vs "log [M] Uridine".

FIG. 3G provides a Gene Set Enrichment Analysis (GSEA) of gene expression in Lys-GFP-ER-HoxA9 cells treated with ML390. The cells demonstrated gene-expression changes consistent with myeloid differentiation by gene set enrichment analysis, "enrichment score" vs "rank in gene list" (top: upregulated genes; bottom: down-regulated genes).

FIG. 4A is a graph showing tumor size during treatment with brequinar. THP1 cells were implanted subcutaneously in the flank of SCID mice, and the mice were treated with vehicle (graph with dots) or brequinar IP (5, g/kg once daily (QD) graph with squares, 15, g/kg every three days (Q3D) graph with triangles) over the course of 10 days. The graph showing "tumor area (mm$^2$)" vs "days"

FIG. 4B shows the results of a flow cytometry analysis of CD11b expression in THP1 cells (top: vehicle; middle panel: brequinar (BRQ) at 5 mg/kg once daily (QD); bottom: brequinar (BRQ) at 5 mg/kg every three days (Q3D)). Tumors were explanted at the end of the 10 days of treatment and analyzed for the differentiation marker CD11b by flow cytometry.

FIG. 4C is a graph showing CD11b expression in cells treated with brequinar (BRQ) at the indicated dose relative to control cells. The geometric mean fluorescence intensity of CD11b-APC expression was compared for the explanted tumors from three mice per group, left vehicle, middle 5 mg/kg QD BRQ, right 15 mg/kg Q3D BRQ.

FIG. 4D shows levels of metabolites that were extracted into methanol from explanted tumors, and levels of intracellular uridine measured by mass spectroscopy. Data in (A) and (C) are represented as the mean±SD. Z, vehicle left dots, BRQ 5 mg/kg QD right squares.

FIG. 5A is a schematic diagram showing a model of the enzymatic steps involved in de novo pyrimidine synthesis. DHODH is located in the mitochondrial inner membrane and passes electrons to ubiquinone.

FIG. 5B is a graph showing fold change in Dihydroorotate. Treatment of ER-HoxA9 cells with ML390 results in an accumulation of dihydroorotate.

FIG. 5C provides a graph showing a depletion of downstream metabolites including left to right UMP, uridine, UDP, UDP-GlcNAc, and UDP-Glucose, Control dark rectangle, ML390 dotted rectangle.

FIG. 5D provides a graph showing percent differentiation in ER-HoxA9 cells treated with pyrazofurin. Treatment of ER-HoxA9 cells with pyrazofurin, an inhibitor of OMP decarboxylase, results in differentiation that can be rescued by uridine supplementation of the culture medium, (–) uridine graph with dots, (+) uridine graph with squares, "% differentiation" vs "log [M] pyrazofurin".

FIG. 5E is an immunoblot. Treatment of cells with ML390 or brequinar, followed by immunoblotting, demonstrates a global decrease in the degree of protein N-acetyl glycosylation (GlcNAc), left to right (–)E2 4 days, (+)E2 control, Brequinar, ML390.

FIG. 6A-E show that brequinar causes differentiation and shows anti-leukemia activity in an in vivo syngeneic model of acute myeloid leukemia (AML).

FIG. 6A is a schematic diagram showing a treatment regimen. A syngeneic model of HoxA9 and Meis1-driven acute myeloid leukemia was used to determine the in vivo activity of brequinar.

FIG. 6B shows results of a flow-cytometric analysis of bone marrow leukemic cells from mice treated with brequinar demonstrates an increase in the expression of differentiation markers CD11b and Gr-1 (left: vehicle; right: brequinar (BRQ) at 25 mg/kg), "Gr-1" vs "Mac1 (CD11b)".

FIG. 6C includes a series of graphs showing an analysis of brequinar treatment. Mice treated with 25 mg/kg brequinar given every other day for a total of 4 doses show decreased leukemic burden in the bone marrow (top, left), normalization of spleen weight (top, center), decreased leukemia in the peripheral blood (top, right), decreased leukemia cells (bottom, left), and increased differentiation markers MAC1 (bottom, center) and GR1 (bottom, right) compared to vehicle-treated mice.

FIG. 6D provides a series of graphs showing an analysis of brequinar treatment. Mice treated with 25 mg/kg brequinar given on day 1 and 4 of a 7-day schedule for a total of 6 doses show an even more dramatic decrease in leukemia burden-leukemic burden in the bone marrow (top, left), normalization of spleen weight (top, center), leukemia in the peripheral blood (top, right), leukemia cells (bottom, left), and differentiation markers MAC1 (bottom, center) and GR1 (bottom, right) compared to vehicle-treated mice.

FIG. 6E provides a series of graphs showing an analysis of brequinar treatment (left to right: mus weight,), hematocrit (HCT), white blood cell count (WBC and platelet count (PLT)). Mice were treated for 3 weeks (from day 14 to day 33) with 5 mg/kg or 10 mg/kg brequinar given every other day (left panel) or 25 mg/kg brequinar given day 1 and 4 of a 7-day schedule. Brequinar-treated mice in all three groups survived longer than vehicle-treated mice.

FIG. 6F provides a series of graphs showing an analysis of brequinar treatment on mouse weight (left to right: mus weight, hematocrit (HCT), white blood cell count (WBC), and platelet count (PLT)).

FIG. 7A provides two micrographs (left: vehicle; right: brequinar). Leukemia cells from mice that were treated with vehicle or brequinar were purified via FACS. Cytospin preparations stained with Wright-Giemsa showed signs of granulocytic maturation, including nuclear condensation and cytoplasmic clearing, in leukemic cells isolated from brequinar-treated mice.

FIG. 7B provides two graphs showing a survival time course for mice treated with brequinar or control (left: study with mice receiving brequinar (BRQ) at 25 mg/kg every other day (Q2D) for 4 doses; right: study with mice receiving brequinar (BRQ) at 25 mg/kg at day 1 (d1) and day 4 (d4) of a 7-day cycle for 6 doses). The same number of purified live leukemia cells from mice treated with vehicle or brequinar were introduced into recipient mice as a functional assay for leukemia-initiating cell activity.

DETAILED DESCRIPTION OF THE INVENTION

Figure 1A:
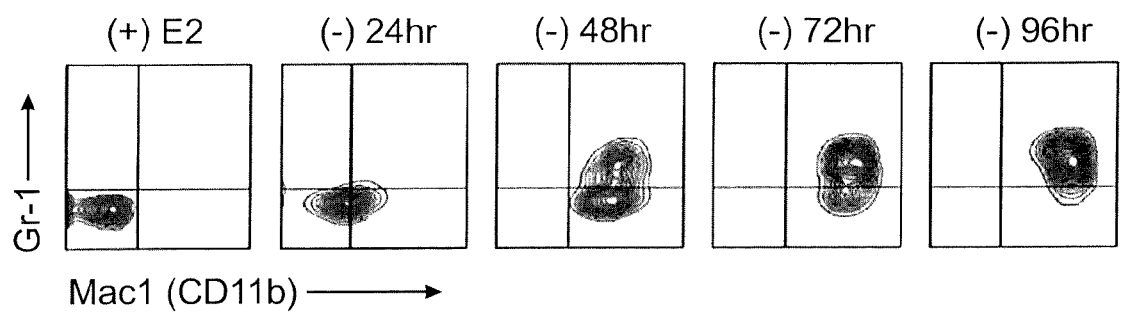
FIG. 1A-1F show that ER-HoxA9 cells faithfully represent a model of conditional myeloid differentiation.

The invention generally provides compounds that can be used to treat or prevent certain types of hematological cancer in a subject in need thereof and methods of administering those compounds to subjects having a hematological cancer. In certain embodiments, the compounds of the invention overcome differentiation arrest in a subject afflicted by a hematological cancer.

The invention is based, at least in part, on the discovery that inhibition of dihydroorotate dehydrogenase (DHODH) enables myeloid differentiation, as well as on the discovery of methods for administering these compounds to enhance their efficacy. In in vivo acute myeloid leukemia (AML) models, DHODH inhibitors reduced leukemic cell burden, decreased levels of leukemia-initiating cells, and improved survival. DHODH inhibition may provide a new metabolic target for overcoming differentiation blockade in patients with AML.

In particular embodiments, the invention provides for the use of the DHODH inhibitor, brequinar, for the treatment of AML. Previous studies of DHODH inhibitors had dosed the inhibitor in a weight-based fashion. In those studies, administration of the DHODH inhibitor led to toxicity and lacked efficacy. Similar results were observed when DHODH inhibitors were administered daily to mice. Such dosing led to severe anemia, severe thrombocytopenia, and death after ~10-days of treatment. Unexpectedly, when the DHODH inhibitor brequinar was administered every 3-days, it was both effective against AML and well-tolerated.

In certain embodiments, the cancers contemplated within the invention are characterized by differentiation arrest. In other embodiments, administration of the compounds of the invention to a subject affected by the cancers contemplated within the invention overcomes differentiation arrest in the cancer. The present invention further comprises compositions comprising one or more of the compounds of the invention, and methods of treating or preventing certain types of hematological cancers using the compounds of the invention.

Acute Myeloid Leukemia

Acute myeloid leukemia (AML) is a clinically devastating disease. Even with improvements in diagnosis and supportive care, the five-year survival rate of an adult with AML is only 30%, with an even more dismal prognosis in those patients over the age of 65. Despite these disappointing outcomes and highlighting the need for novel therapies, the chemotherapy standard of care, a combination of cytarabine and an anthracycline, remains unchanged for more than 40 years.

One hallmark of AML is that the myeloid leukemic blast is arrested at an early stage of differentiation. Prior to the development of fine karyotyping and genetic analysis, morphologic hallmarks of immaturity were used to classify a patient's disease histologically (e.g. the 1976 FAB classification scheme). The recognition that leukemic blasts seemed frozen at an immature stage of differentiation suggested that new therapies might be directed at promoting differentiation rather than simply killing leukemic cells.

In the small subset (10%) of patients with acute promyelocytic leukemia (APL, FAB M3), recurrent chromosomal translocations result in fusion oncoproteins involving the retinoic acid receptor. Exploiting this dependency by treating patients with all-trans retinoic acid (ATRA) and arsenic trioxide releases the cells from differentiation arrest, allowing the leukemic blasts to resume their normal maturation process to terminally differentiated neutrophils. The dramatic success and clinical impact of this differentiation therapy has inverted the survival curve for patients with APL. Where APL was once among the worst prognostic subsets of AML, it now has the best outlook for cure, with overall survival rates in excess of 85%. An unmet challenge is to identify similar differentiation therapies for the remaining 90% of patients with non-APL acute myeloid leukemia.

Extensive efforts to identify new therapeutic targets to overcome myeloid differentiation blockade have been largely unsuccessful. In a recent development analogous to APL, small-molecule inhibitors of mutant isocitrate dehydrogenase 2 (IDH2) may be capable of inducing cellular differentiation among that subset (9%) of patients with IDH2 mutations. However, the remainder of AML cases involve complex and heterogeneous combinations of chromosomal alterations and gene mutations. The development of mutation-specific therapeutics is a daunting challenge, and even rationally designed potent inhibitors of targets such as mutant Flt3 have been clinically disappointing.

An alternative strategy was pursued based on reasoning that diverse mutagenic events that affect differentiation or self-renewal may funnel through common molecular pathways. This strategy sought to define and target pathways of differentiation that might be shared across a range of genetic subtypes of AML. Intriguingly, the expression of the homeobox transcription factor HoxA9 was upregulated in 70% of patients with AML, likely reflecting that the leukemic blasts are halted at a common stage of differentiation arrest. HoxA9 is critical to normal myelopoiesis, and its expression must be downregulated to permit normal differentiation. Furthermore, HoxA9 is important to the maintenance of leukemias driven by MLL translocations such as MLL/AF9, HoxA9 is upregulated during the transition in chronic myeloid leukemia patients to blast-phase disease, and HoxA9 expression itself is an independent risk factor in children with leukemia. Therefore, without intending to be bound by theory, though it is not found to be mutated, the persistent expression of HoxA9 might represent a commonly dysregulated node in AML suitable for therapeutic targeting across a range of disparate subtypes.

As there are no known small-molecule inhibitors of HoxA9, a cellular model of HoxA9-enforced myeloid differentiation arrest that could be used in an unbiased phenotypic screen was developed. As the persistent expression of HoxA9 results in myeloid differentiation arrest, an estrogen receptor-HoxA9 (ER-HoxA9) fusion protein was used to conditionally immortalize cultures of primary murine bone marrow. ER-HoxA9 cells were generated from the bone marrow of a mouse in which GFP was knocked into the lysozyme locus. Since lysozyme is a myeloid granule protein expressed only in terminally differentiated cells, this cell-line system permitted a large-scale phenotypic screen of small molecules to identify those capable of triggering differentiation in the presence of active HoxA9.

Dihydroorotate dehydrogenase (DHODH) was identified as the target of the most active compounds. DHODH is the enzyme responsible for the fourth and rate-limiting step of de novo pyrimidine biosynthesis, and its modulation has not previously been shown to induce AML differentiation. In this study, DHODH inhibitors exerted potent differentiation activity in vitro and in vivo in both murine and human models of AML. Without intending to be bound by theory, the anti-leukemic activity of DHODH inhibitors points towards a novel link between uridine biosynthesis and cell fate decisions, and may offer a much-needed new therapeutic option for treatment of patients with AML.

Compounds

In one aspect, the invention provides anticancer compounds. In certain embodiments, the compounds comprise an inhibitor of a mammalian DHODH (dihydroorotate dehydrogenase), or a salt or solvate thereof. In other embodiments, the mammalian DHODH comprises human DHODH.

In certain embodiments, the invention includes at least one compound, or a salt or solvate thereof, selected from the group consisting of:

brequinar (also known as 6-fluoro-2-(2'-fluoro-[1,1'-biphenyl]-4-yl)-3-methyl-quinoline-4-carboxylic acid)

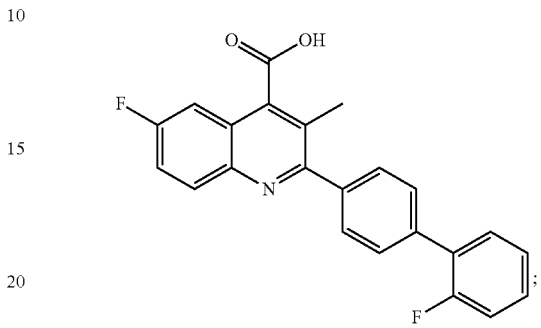

leflunomide (also known as 5-methyl-N-[4-(trifluoromethyl) phenyl]-isoxazole-4-carboxamide)

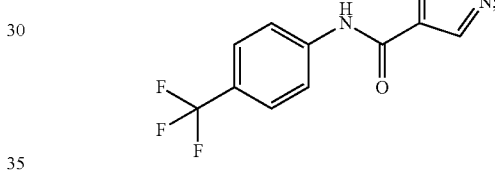

teriflunomide (also known as (2Z)-2-cyano-3-hydroxy-N-[4-(trifluoromethyl) phenyl]but-2-enamide)

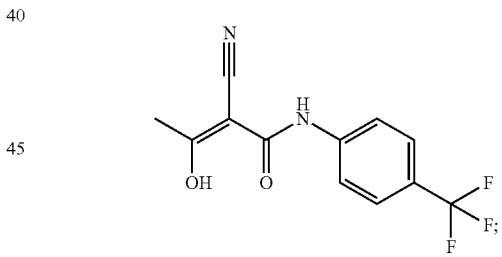

or any combinations thereof.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, or methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The invention further includes a pharmaceutical composition comprising the compound of the invention and a pharmaceutically acceptable carrier.

In certain embodiments, the pharmaceutical composition further comprises at least one additional agent that is useful to treat the diseases or disorders contemplated herein. In certain embodiments, the compound of the invention and the additional agent are co-formulated in the composition.

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Combination Therapies

In certain embodiments, the compounds of the invention are useful in the methods of the invention in combination with at least one additional agent useful for treating or preventing a disease or disorder contemplated within the invention. This additional agent may comprise compounds identified herein or compounds, e.g., commercially available compounds, known to treat, prevent or reduce the symptoms of a hematological cancer, such as, but not limited to, acute myeloid leukemia (AML), acute promyelocytic leukemia (APL), mixed-lineage leukemia (MLL), acute lymphocytic leukemia (ALL), myelodysplastic syndrome (MDS), chronic myeloid leukemia (CML), and/or myelo-monocytic leukemia (MML).

In certain embodiments, the at least one additional agent is an anticancer agent.

The anti-cancer agent may be selected from the group consisting of 131I-chTNT, abarelix, abiraterone, aclarubicin, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, Iasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumabpentetreotide, nilotinib, nilutamide, nimorazole, nimotuzumab, nimustine, nintedanib, nitracrine, nivolumab, obinutuzumab, octreotide, ofatumumab, olaparib, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+ sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin but is not limited thereto.

In other embodiments, the at least one additional agent is an anticancer agent, especially cytarabine and/or an anthracycline.

In other embodiments, the at least one additional agent comprises ATRA or arsenic trioxide.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Methods and Use

In one aspect, the invention includes a method of treating or preventing a hematological cancer in a subject. In certain embodiments, the method comprises administering to the subject a therapeutically effective amount of at least one compound of the invention. In other embodiments, the at least one compound of the invention is formulated in a pharmaceutical composition.

In certain embodiments, the hematological cancer is characterized by differentiation arrest. In other embodiments, the hematological cancer comprises acute myeloid leukemia (AML), acute promyelocytic leukemia (APL), mixed-lineage leukemia (MLL), myelodysplastic syndrome (MDS), and/or chronic myeloid leukemia (CML). In yet other embodiments, the hematological cancer comprises AML.

In certain embodiments, the compound of the invention comprises at least one compound, or a salt or solvate thereof, selected from the group consisting of brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof.

In certain embodiments, the compound of the invention comprises brequinar (also known as 6-fluoro-2-(2'-fluoro-[1,1'-biphenyl]-4-yl)-3-methylquinoline-4-carboxylic acid) or a salt or solvate thereof.

In certain embodiments, the compound or composition is administered to the subject by at least one route selected from oral, rectal, mucosal (e.g., by oral or nasal inhalation), transmucosal, topical (transdermal), and intravenous, intradermal, intramuscular, subcutaneous, intracutaneous, intrauterine, epidural and intracerebroventricular injections. In other embodiments, the subject is further administered at least one additional agent useful for treating or preventing a hematological cancer. In yet other embodiments, the subject is a mammal. In yet other embodiments, the mammal is human. In yet other embodiments, the subject is not responsive to one or more commercially available and/useful anticancer agents.

In certain embodiments the invention includes the compounds for use in treating or preventing hematological cancer, more specifically dihydroorotate dehydrogenase inhibitors (DHODH inhibitors), even more specifically brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof or a salt or solvate thereof.

In further certain embodiments the invention includes the compounds for use in treating or preventing hematological cancer, more specifically dihydroorotate dehydrogenase inhibitors (DHODH inhibitors), even more specifically brequinar (also known as 6-fluoro-2-(2'-fluoro-[1,1'-biphenyl]-4-yl)-3-methylquinoline-4-carboxylic acid) or a salt or solvate thereof.

In certain further embodiments the invention includes the compounds for use whereby the hematological cancer is acute myeloid leukemia (AML), acute promyelocytic leukemia (APL), mixed-lineage leukemia (MLL), myelodysplastic syndrome (MDS), and/or chronic myeloid leukemia (CML).

In certain other embodiments the invention includes the compounds for use whereby the hematological cancer is acute myeloid leukemia (AML).

In certain other embodiments the invention includes dihydroorotate dehydrogenase inhibitors (DHODH inhibitors) for use in treating or preventing hematological cancer, more specifically is acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML).

In certain other embodiments the invention includes compounds selected from the group consisting of brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof or a salt or solvate thereof for use in treating or preventing hematological cancer, more specifically is acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML).

In other embodiments the invention includes a use of a compound selected from the group consisting of brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof or a salt or solvate thereof for the manufacture of a medicament for the prophylaxis or treatment of hematological cancer, more specifically is acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML).

Formulations/Administration

The compositions of the present invention may contain a pharmaceutical acceptable carrier, excipient and/or diluent, and may be administered by a suitable method to a subject.

Thus in certain further embodiments the invention includes a composition comprising a compound selected from the group consisting of brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof or a salt or solvate thereof for use in the prevention or treatment, more specifically for the treatment of hematological cancer, more specifically is acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML).

In certain other embodiments the invention includes a composition comprising a compound selected from the group consisting of brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof or a salt or solvate thereof together with a pharmaceutical acceptable carrier, excipient and/or diluent for use in the prevention or treatment, more specifically for the treatment of hematological cancer, more specifically is acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML).

The compositions of the present invention may be formulated in various forms, including oral dosage forms or sterile injectable solutions, according to any conventional method known in the art. In other embodiments, the compositions may also be used as an inhalation-type drug delivery system. In yet other embodiments, the compositions of the invention may be formulated for injectable solutions.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.). Carriers, excipients and diluents that may be contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyl hydroxylbenzoate, talc, magnesium stearate or mineral oil.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g., BHT), buffering agents (for example phosphate or citrate buffers), and effervescent agents such as citrate/bicarbonate mixtures. Such excipients are well known and do not need to be discussed in detail here. Capsule formulations may be of the hard gelatin or soft gelatin variety and can contain the active component in solid, semi-solid, or liquid form. Gelatin capsules can be formed from animal gelatin or synthetic or plant derived equivalents thereof. The solid dosage forms (e.g., tablets, capsules etc.) can be coated or un-coated, but typically have a coating, for example a protective film coating (e.g. a wax or varnish) or a release controlling coating. The coating (e.g., a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes. Instead of, or in addition to, a coating, the antibiotic can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. Each tablet, capsule, caplet, pill, etc. can be a single dose, with a dose, for example, as herein discussed, or a dose can be two or more tablets, capsules, caplets, pills, and so forth; for example if a tablet, capsule and so forth is 125 mg and the dose is 250 mg, the patient may take two tablets, capsules and the like, at each interval there is to administration.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, Laurin fat, or glycerogelatin may be used.

The preferred dose of the pharmaceutical compositions of the present invention varies depending on the patient's condition and weight, the severity of the disease, the type of drug, and the route and period of administration and may be suitably selected by those skilled in the art. For preferred effects, the pharmaceutical composition of the present invention may be administered at a dose of 0.01-100 mg/kg/day. The administration may be anywhere from 1 to 4 times daily, e.g., once, twice, three times or four times daily. The maximum amount administered in a 24 hour period may be up to 1500 mg. The administration may be over a course of 2 to 30 days, e.g., 3 to 21 days, such as 7, 10 or 14 days. The skilled person can adjust dosing depending on the subject's body weight and overall health condition and the purpose for administering the antibiotic. Repeated courses of treatment may be pursued depending on the response obtained.

In certain embodiments the invention includes dihydroorotate inhibitors (DHODH inhibitors), more specifically brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl] but-2-enamide); or any combinations thereof or a salt or solvate thereof for use in a method of preventing or treating hematological cancer, more specifically acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML) comprising administering the compound to a subject in need thereof with a frequency less than or equal to once every 48 hours.

In certain other embodiments the invention includes dihydroorotate inhibitors (DHODH inhibitors), more specifically brequinar (also known as 6-fluoro-2-(2'-fluoro-[1,1'-biphenyl]-4-yl)-3-methylquinoline-4-carboxylic acid); leflunomide (also known as 5-methyl-N-[4-(trifluoromethyl) phenyl]-isoxazole-4-carboxamide); teriflunomide (also known as (2Z)-2-cyano-3-hydroxy-N-[4-(trifluoromethyl)phenyl]but-2-enamide); or any combinations thereof or a salt or solvate thereof for use in a method of preventing or treating hematological cancer, more specifically acute myeloid leukemia (AML), acute promyelocytic leukemia (APL), mixed-lineage leukemia (MLL), myelodysplastic syndrome (MDS), and/or chronic myeloid leukemia (CML), even more specifically acute myeloid leukemia (AML) comprising administering the compound to a subject in need thereof with a frequency less than or equal to once every 72 hours.

The compositions of the present invention may be administered to a subject by various routes. All modes of administration are contemplated, for example, orally, rectally, mucosally (e.g., by oral or nasal inhalation), transmucosally, topically (transdermal), or by intravenous, intradermal, intramuscular, subcutaneous, intracutaneous, intrauterine, epidural or intracerebroventricular injection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and therapeutic methods of the invention, and are not intended to limit the scope of what the inventor(s) regard(s) as the invention.

EXAMPLES

The invention is now described with reference to the following Examples. These Examples are provided for the purpose of illustration only, and the invention is not limited to these Examples, but rather encompasses all variations that are evident as a result of the teachings provided herein.

Unless noted otherwise, the starting materials for the synthesis described herein were obtained from commercial sources or known synthetic procedures and were used without further purification.

Biological Examples

Example 1: An ER-HoxA9 Fusion Establishes a Model of Conditional Myeloid Differentiation Arrest High-throughput myeloid differentiation assays are challenging, as specific measures of myeloid differentiation are cumbersome and have historically relied on morphologic or enzymatic assays or more recently on changes in gene expression. Furthermore, myeloid differentiation has typically been assessed in AML cell lines where the mechanism of differentiation arrest is not defined.

An estrogen receptor-HoxA9 (ER-HoxA9) fusion protein was used to immortalize cultures of primary murine bone marrow conditionally. The persistent expression of the wild-type HoxA9 protein is sufficient to enforce myeloid differentiation arrest in cultures of murine bone marrow, and injection of these cells into recipient mice leads to acute myeloid leukemia (AML), albeit with a long latency (Kroon et al., The EMBO Journal 17, 3714-3725, 1998). Fusion of the hormone-binding domain of the human estrogen receptor (ER) to the N-terminus of HoxA9 results in a protein that is constitutively translated and sequestered in an inactive form in the cytoplasm in the absence of beta-estradiol (E2). Upon binding its beta-estradiol ligand, the ER-HoxA9 protein translocates to the nucleus where it retains its wild-type activity as a transcription factor. The G400V variant of the human ER was used. This variant renders it insensitive to physiologic concentrations of estrogen or to the trace estrogens that are found in fetal bovine serum (FIG. 1H).

Figure 1B:
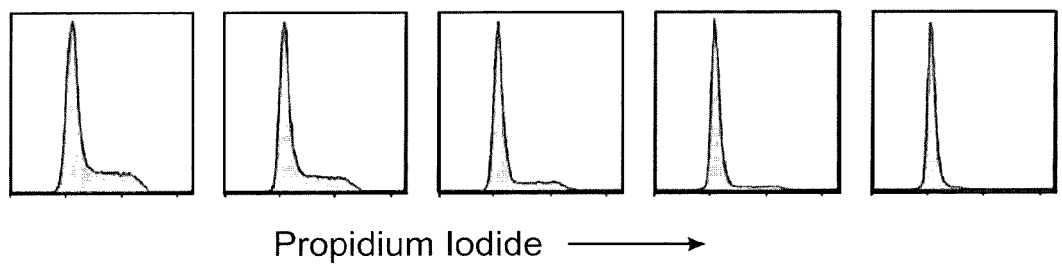
Figure 1C:
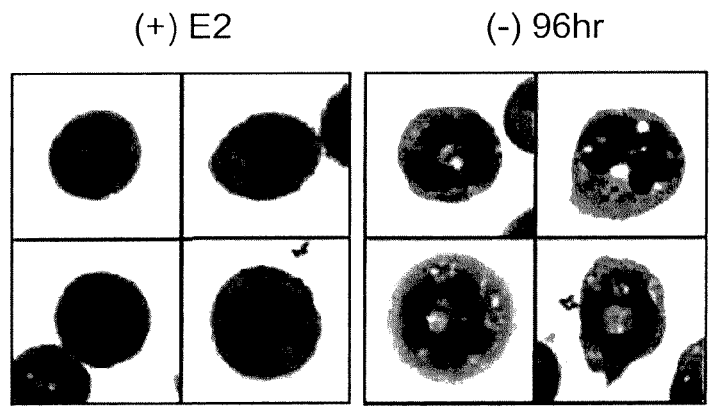
Figure 1D:
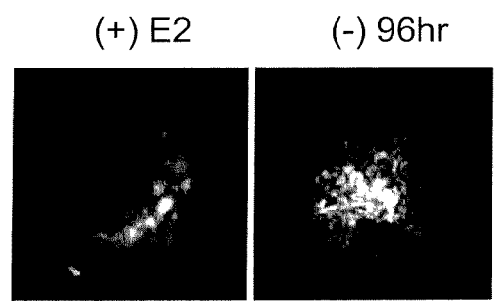
Figure 1E:
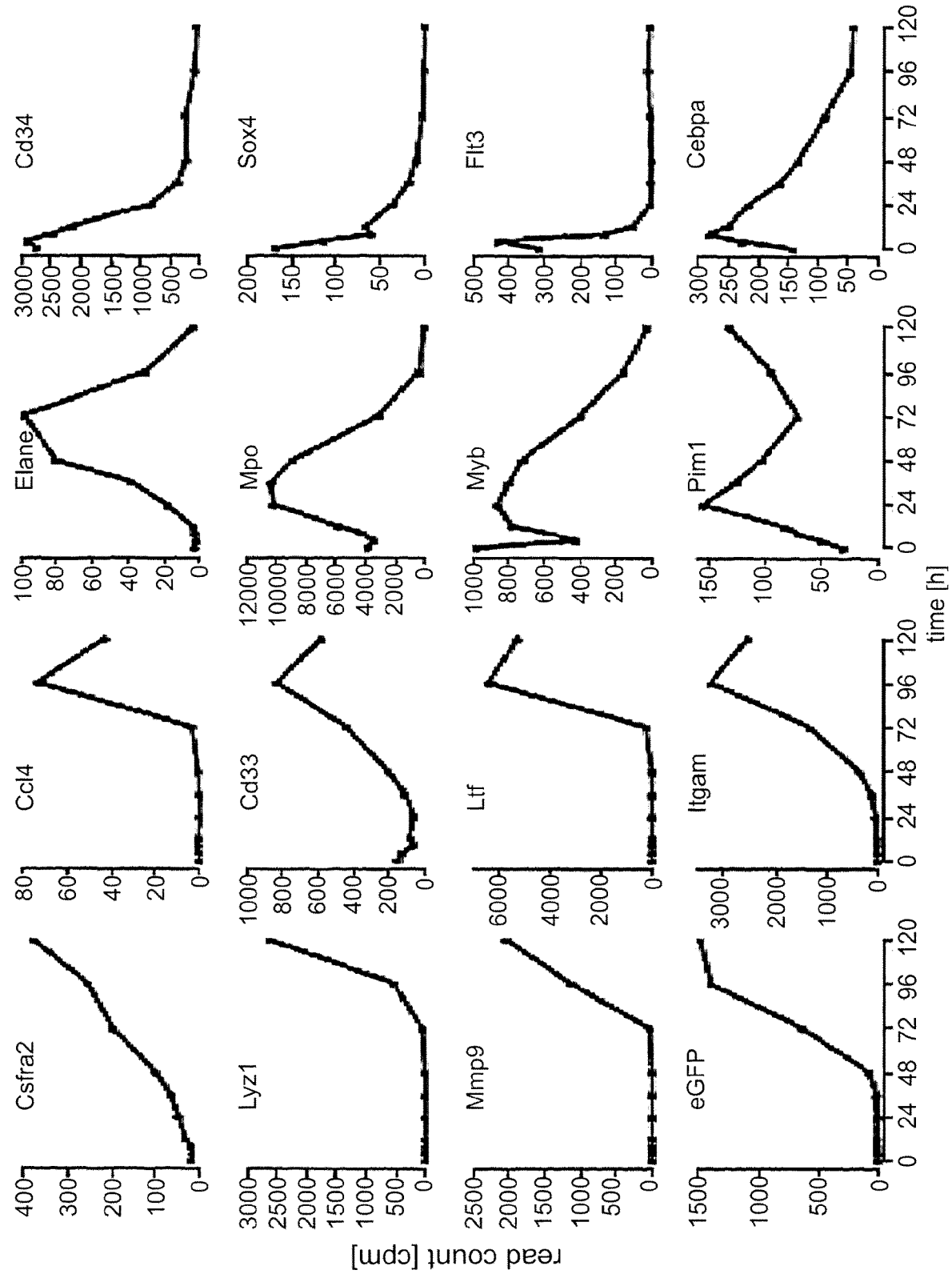
Figure 1F:
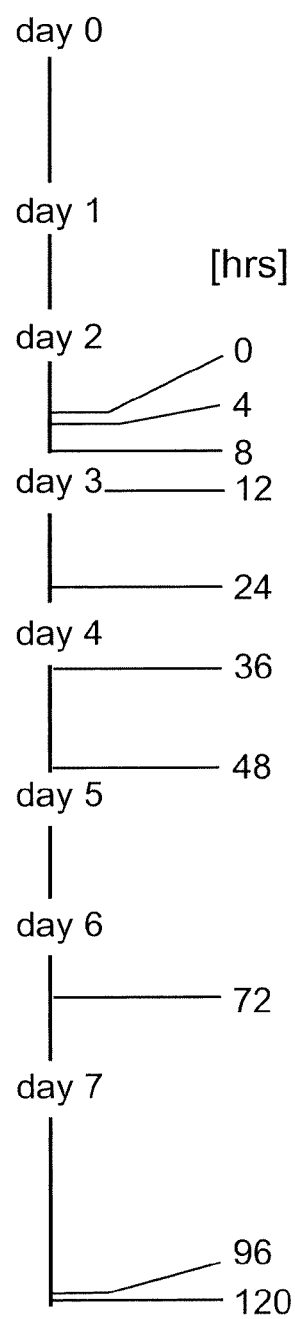
Figure 1G:
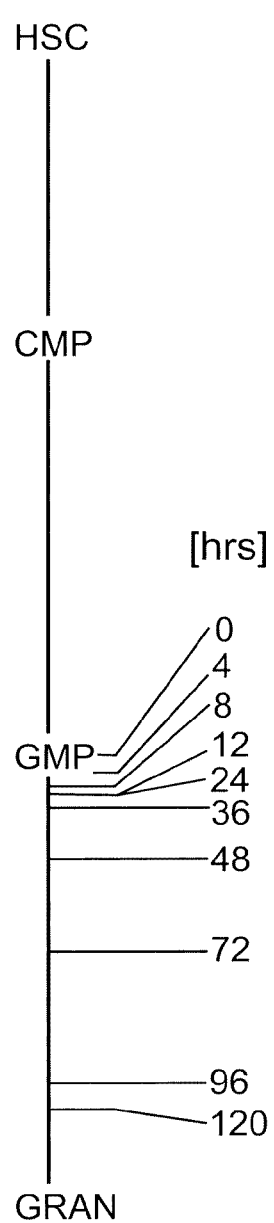
FIG. 1G is a schematic showing a comparison time course in primary human bone marrow cells.
Figure 1I:
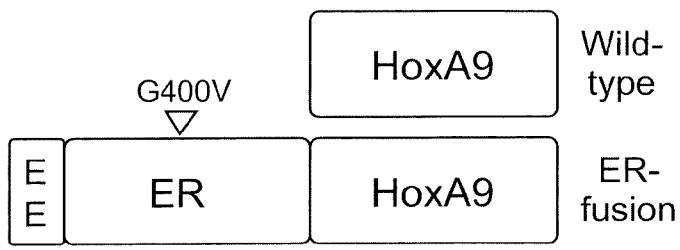
FIG. 1I shows a cell surface marker profile of primary murine bone marrow cells transduced with the ER-HoxA9 construct (top, from left to right: SSC-A vs. FSC-A; FSC-W vs. FSC-A; SSC-W vs. SSC-A; 7AAD vs. FSC-A; bottom, from left to right: KIT vs. LIN; KIT vs. SCA; CD16/32 vs. CD34; normal bone marrow: CD16/32 vs. CD34).
Figure 1I:
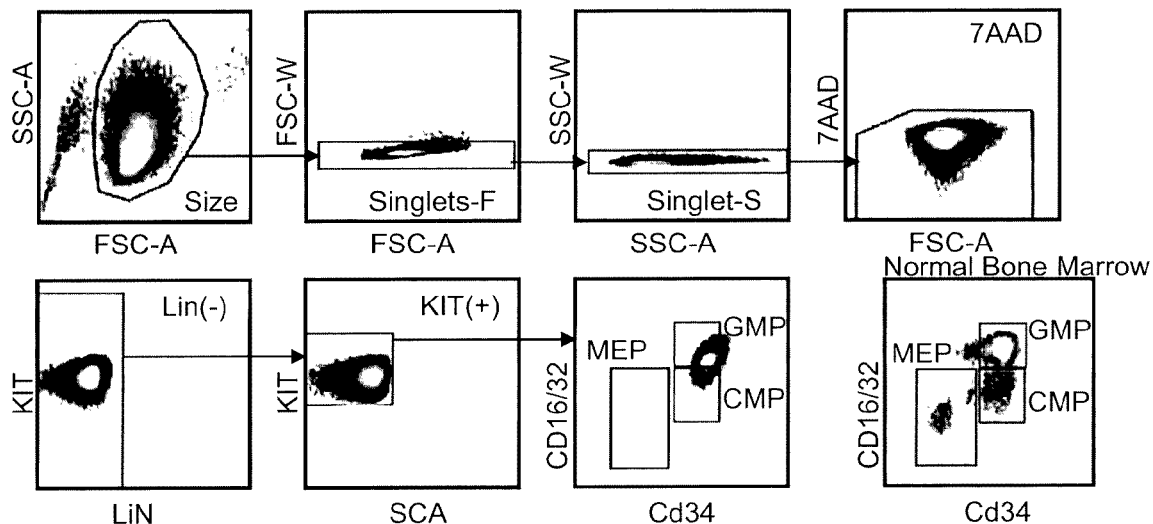
Figure 1J:
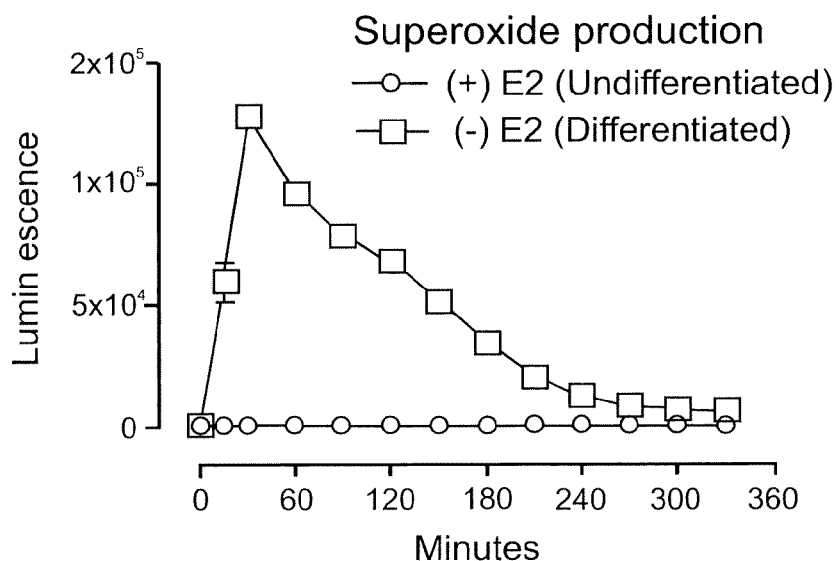
FIG. 1J is a graph showing superoxide production in undifferentiated murine bone marrow cells transduced with the ER-HoxA9 construct (graph with squares) and in undifferentiated control cells (graph with dots).

Primary murine bone marrow cells transduced with the ER-HoxA9 construct proliferate as stem cell factor-dependent myeloblast cell lines, with the cell-surface receptor profile consistent with that of granulocyte-macrophage progenitors (GMPs) (FIG. 1I). In the presence of beta-estradiol and active ER-HoxA9 protein these cells proliferate indefinitely as immature myeloblasts, while upon withdrawal of beta-estradiol, the cells undergo synchronous and terminal neutrophil differentiation over the course of 4-5 days, demonstrating the expected changes in cell-surface CD11b and Gr-1 expression (FIG. 1A). This normal and terminal granulopoietic differentiation was confirmed by assaying changes in cell cycle (FIG. 1B) and morphology (FIG. 1C), as well as by assays of functional neutrophil effector function including phagocytosis (FIG. 1D) and superoxide production (FIG. 1J).

Figure 1K:
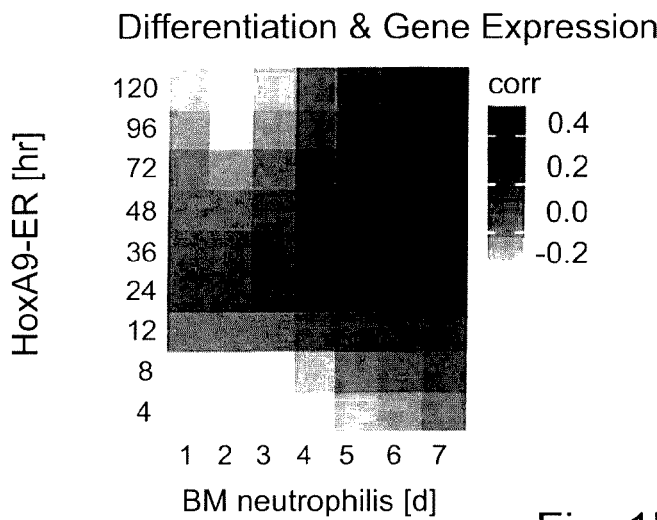
FIG. 1K is a heat-map showing gene expression patterns during beta-estradiol (E2) induced differentiation of HoxA9-ER [hr] bone marrow derived neutrophils [d] vs. control cells.
Figure 1L:
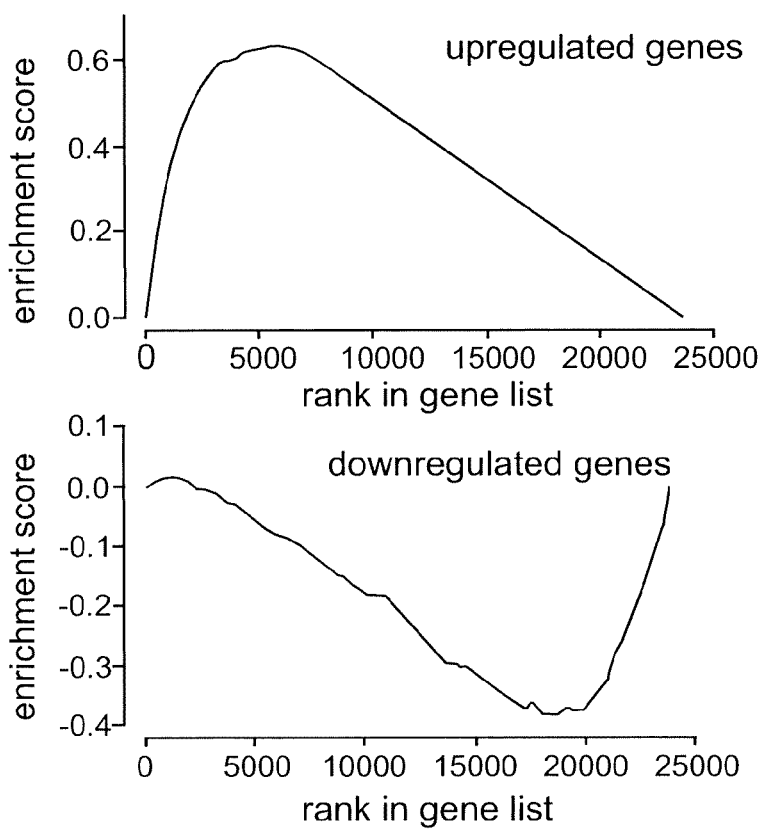
FIG. 1L provides two graphs showing a Gene Set Enrichment Analysis (GSEA) of gene expression patterns during beta-estradiol (E2) induced differentiation of HoxA9-ER bone marrow derived neutrophils vs. control cells (top: upregulated genes; bottom: down-regulated genes).

Example 2: Lysozyme-GFP-ER-HoxA9 Cells Establish a Model for a Phenotypic Screen of AML Differentiation In order to facilitate a small-molecule differentiation screen, an ER-HoxA9 GMP cell line was derived from the bone marrow of the lysozyme-GFP (green fluorescent protein) knock-in mouse, in which the expression of GFP is limited to mature myeloid cells. Time-course gene-expression analysis by RNA-sequencing (RNA-Seq) was performed on undifferentiated cells cultured in beta-estradiol as well as at 9 time points following the removal of beta-estradiol, up to 120 hours. The pattern of expression of key neutrophil genes (Elane, Mpo) as well as HoxA9 target genes (Cd34, Flt3) demonstrates the expected stepwise pattern of transcription factors, primary granule proteins, and secondary granule proteins (FIG. 1E). Gene expression was compared to that of unmanipulated cultures of primary murine myeloblasts allowed to differentiate in vitro over 7 days (FIGS. 1F, 1K, 1L, as well as to freshly sorted subsets of human myeloid cells (FIG. 1G). The step-wise pattern of gene expression during the differentiation of ER-HoxA9 cells shows remarkable similarity with that of murine and human primary myeloblasts.

Figure 2A:
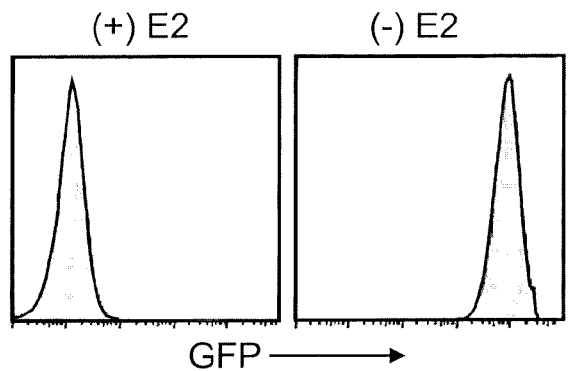
FIG. 2A-2H shown high-throughput screening and medicinal chemistry identifies the small molecule ML390 as an inducer of myeloid differentiation.
Figure 2B:
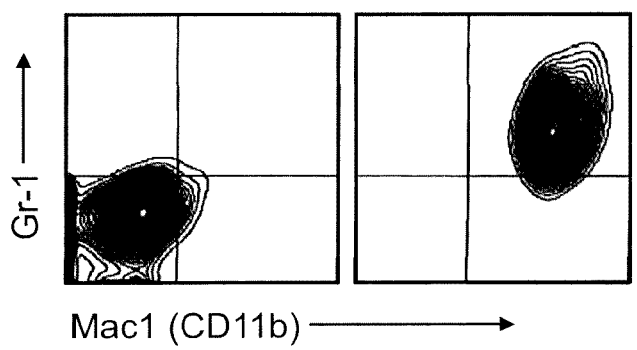
Figure 2C:
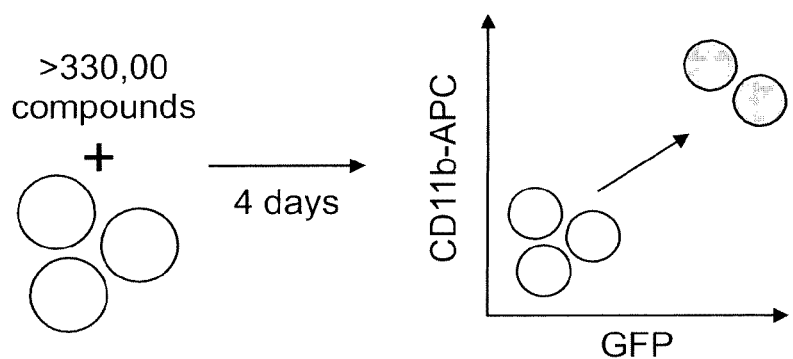
Figure 2D:
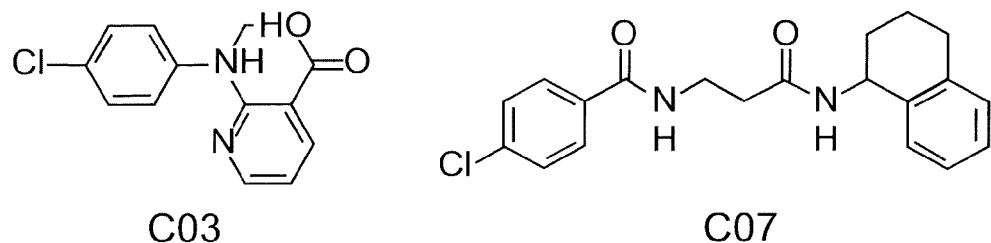
Figure 2E:
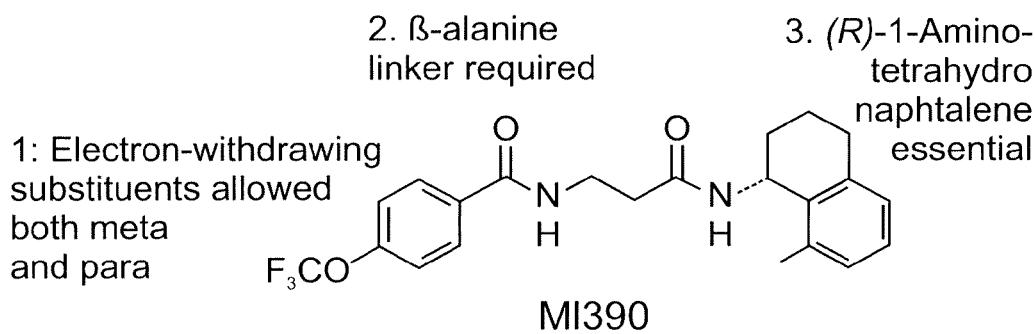
Figure 2F:
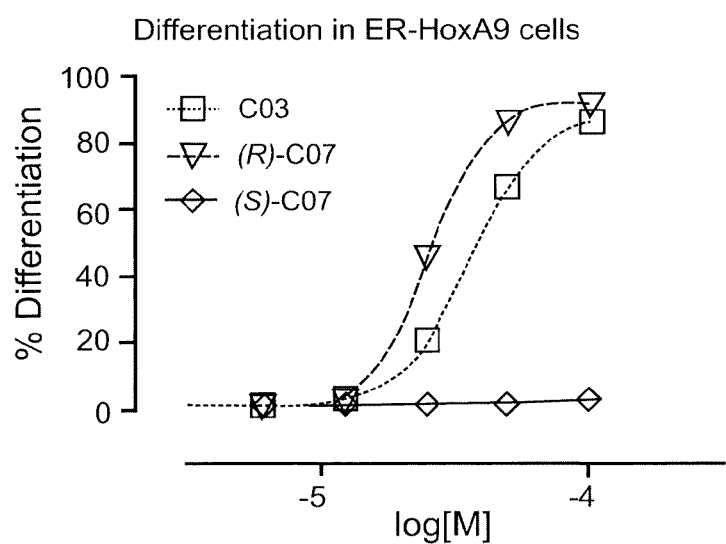
Figure 2G:
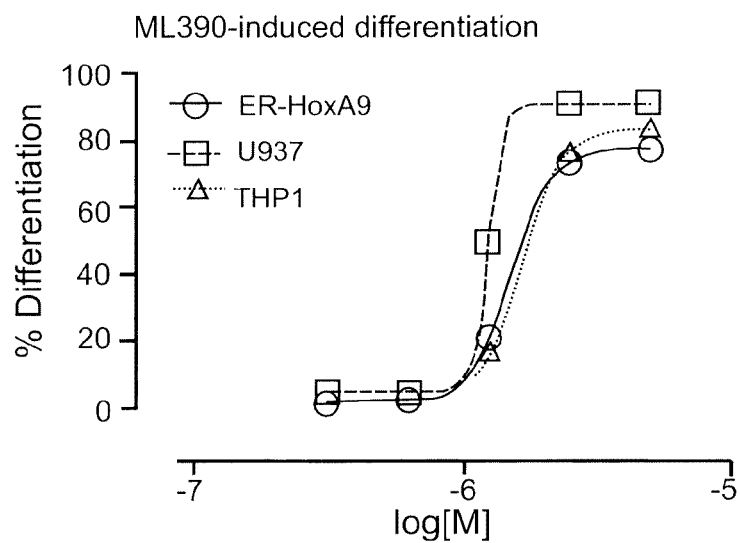
Figure 2H:
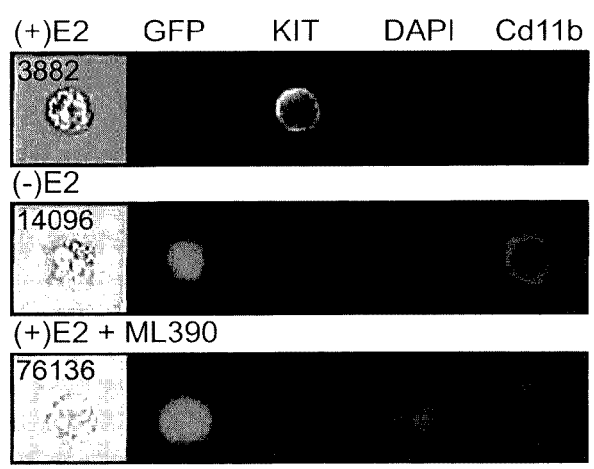
Figure 2I:
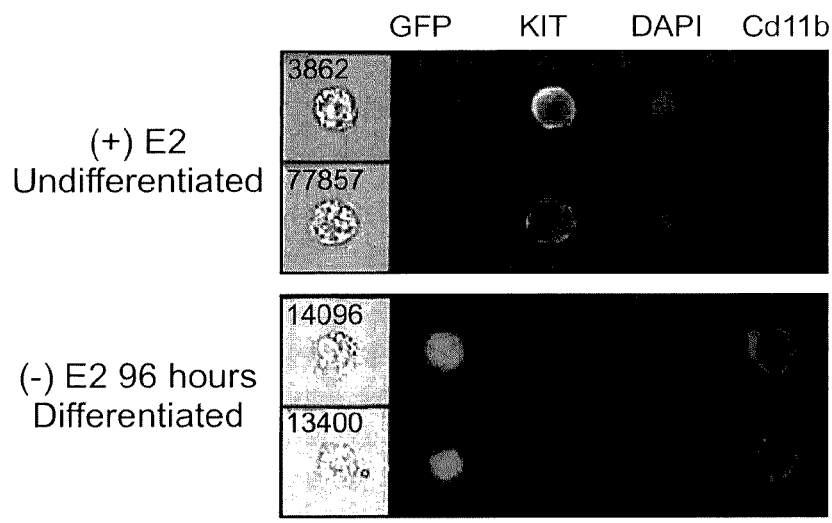
FIG. 2I shows imaging flow cytometry analysis of GFP, KIT, CD11b, and DAPI in undifferentiated and differentiated Lys-GFP-ER-HoxA9 cells at 96 hours (top: undifferentiated, in the presence of beta-estradiol, (+) E2; bottom: differentiated, 96 hrs. after removal of E2, (−) E2 96 hours).

In the Lys-GFP-ER-HoxA9 cell line, GFP expression accompanied the normal process of myeloid differentiation (FIGS. 1E, 2A) and paralleled the expression of the myeloid markers CD11b and Gr-1 (FIG. 2B). Imaging flow cytometry showed that the single-cell morphologic changes associated with differentiation were accompanied by an increase in cell-surface CD11b staining, a decrease in cell-surface CD117 (CKIT) staining, and an increase in cytoplasmic GFP expression (FIG. 2I). Example 20 provides a method for screening compounds that may promote myeloid differentiation.

Figure 2J:
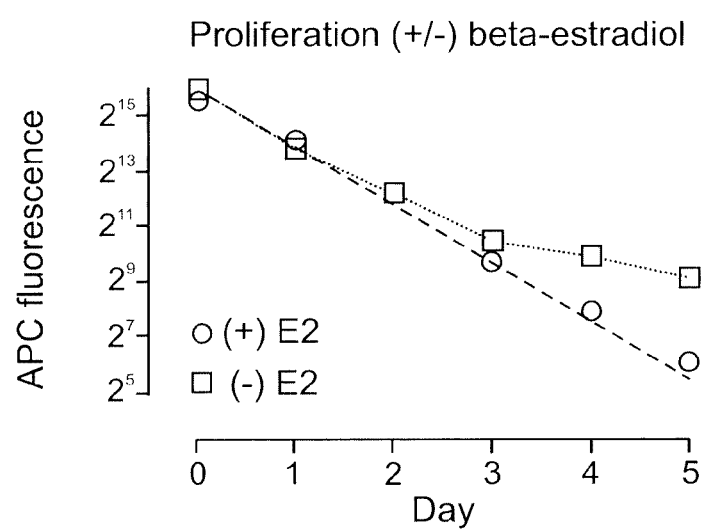
FIG. 2J is a graph showing an analysis of cell proliferation in Lys-GFP-ER-HoxA9 cells in the presence (+)E2, graph with dots/absence of beta estradiol (−E2), graph with squares.

Like the wild-type ER-HoxA9 GMPs, the Lys-GFP-ER-HoxA9 cells were SCF-dependent, had a doubling time of approximately 12 hours and underwent 4-5 doublings prior to terminal differentiation over a period of 5 days when cultured out of beta-estradiol (FIG. 2J).

Example 3: A High-Throughput Screen Identifies 12 Small Molecules as Mediators of Myeloid Differentiation Using the Lys-GFP-ER-HoxA9 GMPs, a high-throughput small-molecule phenotypic screen was performed to identify compounds that could trigger myeloid differentiation in the presence of active HoxA9. (See Example 20 for assay details.) After four days of compound treatment, cells were assessed by high-throughput flow cytometry for viability based on forward and side-scatter properties, and for differentiation as determined by the endogenous expression of GFP and cell-surface expression of CD11b (APC fluorescence, FIG. 2C). The assay achieved a Z-factor of 0.9, indicating an excellent signal-to-noise ratio. The differentiation potential of more than 330,000 small molecules within the NIH Molecular Library Program's Molecular Library Small-Molecule Repository (MLSMR) library was assessed over approximately 25 screening days.

Active compounds were re-screened by flow cytometry in concentration-response experiments to eliminate toxic compounds (<10% viable cells), autofluorescent (green and/or far-red fluorescent) compounds, and estrogen antagonists. 12 compounds demonstrated reproducible myeloid differentiation in multiple clones of ER-HoxA9 and wild-type HoxA9 murine GMP cell lines. The 12 active compounds were screened for cross-species differentiation activity in four human cell-line models of AML (HL60, NB4, THP1, and U937). Compounds designated 3 and 7 (C03 and C07, FIG. 2D) promoted differentiation (as assayed by upregulation of CD11b expression) in the U937 and THP1 human leukemia cell lines and were selected as starting points for compound optimization.

Example 4: ML390 is a Potent Derivative of C07

Two compounds with distinct chemical scaffolds (C03 and C07) were chosen for further study based on their cross-species activity in both murine and human AML models. Compound C03 was structurally similar to known non-steroidal anti-inflammatory compounds (NSAIDs) as well as to known inhibitors of aldo-keto reductase 3 (AKR3). However, treatment of the Lys-GFP-ER-HoxA9 cells with a variety of confirmed NSAIDs or AKR3 inhibitors did not result in myeloid differentiation, suggesting that this was not the mechanism of action. Several structural analogs of C03 were no more potent than the parent compound in our differentiation assay (See Example 20).

The enantiomers of C07 were synthesized separately and the biological activity was specific to the (R)-enantiomer. (FIG. 2F). See Example 12 for synthetic details. The (R)-C07 halide group was varied to increase the potency, resulting in the lead compound designated ML390 (FIG. 2E). ML390 was active with an $ED_{50}$ (effective concentration triggering 50% of its maximal differentiation activity) of approximately 2 µM in murine and human AML cell lines (FIG. 2G). The differentiation triggered by incubation with ML390 was similar to the normal differentiation accompanying ER-HoxA9 inactivation as measured by imaging flow cytometry to simultaneously compare cell morphology, intracellular GFP fluorescence, and cell-surface staining (FIG. 2H).

Example 5: Analysis of Resistant Cell Lines Identifies Dihydroorotate Dehydrogenase as the Target of ML390

Having undertaken a phenotypic screen of a largely un-annotated library, the protein targets of the 12 active small molecules were unknown. Target identification via the generation of compound-resistant cell lines was an approach that had been previously successful in our laboratories. To generate resistant cell lines, the murine Lys-GFP-ER-HoxA9 and human U937 leukemia cells were cultured in slowly escalating (5 µM to 50 µM) concentrations of DMSO, C03, or (R)-C07. Initially the treated cells grew very slowly and appeared more differentiated (on the basis of morphology and CD11b staining) than the parental cells.

Figure 3A:
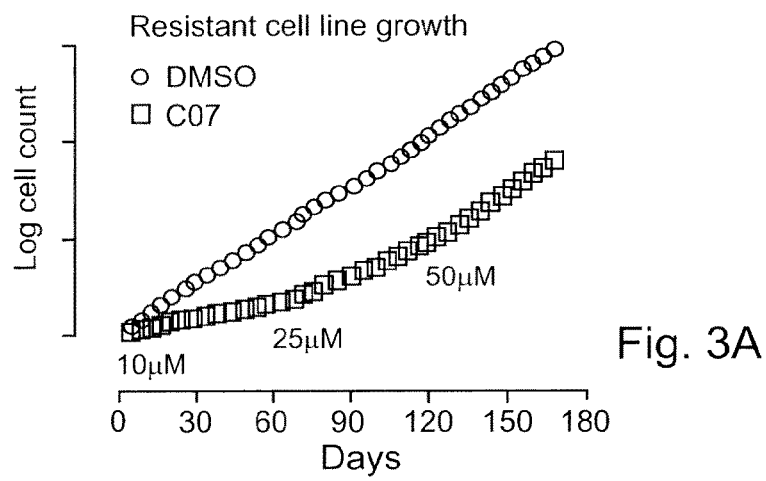
FIG. 3A-3G shows that resistant cell lines identify DHODH as the target of ML390.
Figure 3B:
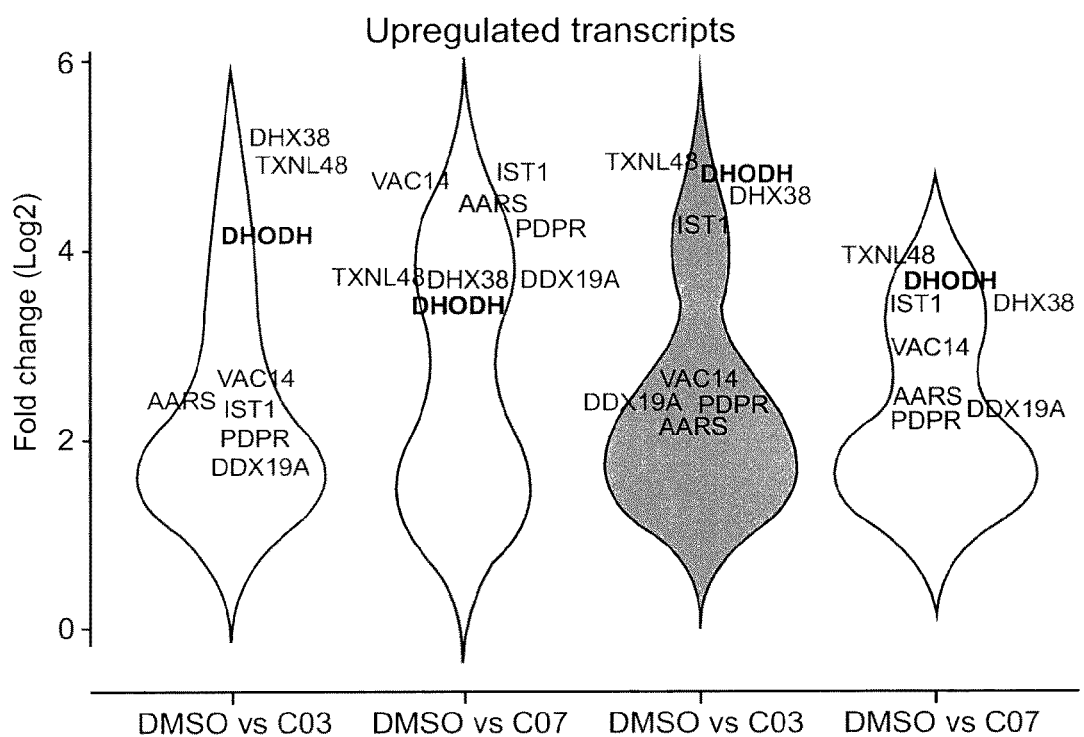

Over a period of six months, with passage every 3-4 days, resistant undifferentiated cells emerged that proliferated at the same rate and were indistinguishable from cells cultured in DMSO vehicle (FIGS. 3A, 3B). Resistant cell lines emerged in a similar time frame in both the (R)-C07 and C03-treated cultures, as well as in both murine and human cell lines. Despite their seemingly unrelated chemical structures, cells resistant to (R)-C07 exhibited cross-resistance to C03, and vice versa, suggesting a similar resistance mechanism. Furthermore, cells retained their resistance for more than six weeks after discontinuing treatment with either compound, suggesting a stable genetic alteration as the mechanism of resistance.

Figure 3C:
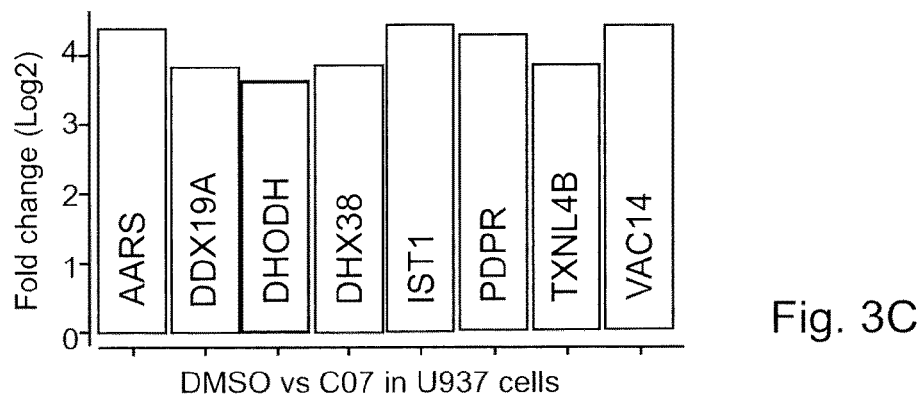
Figure 3D:
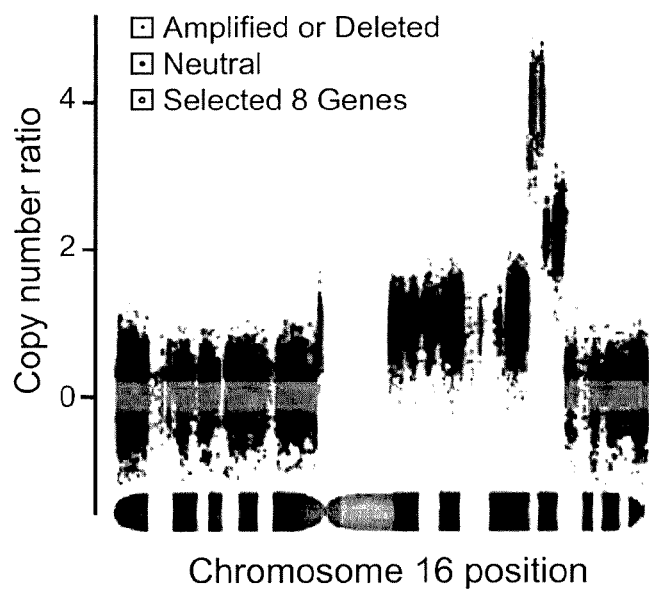
Figure 3E:
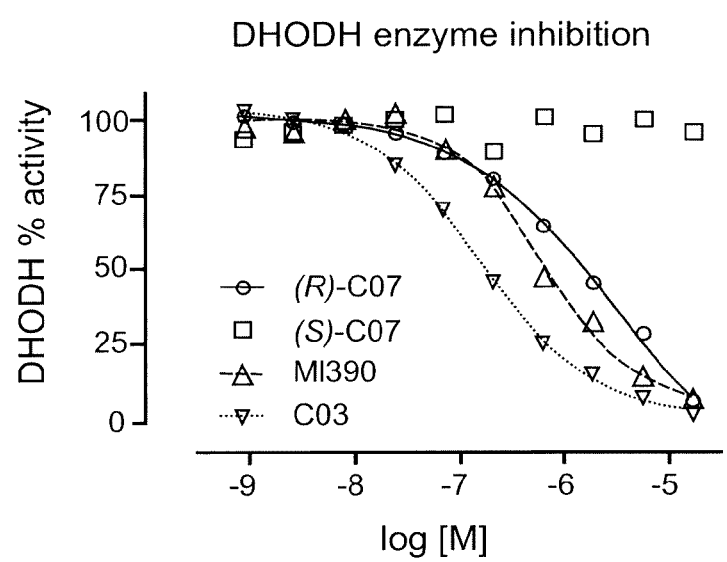
Figure 3F:
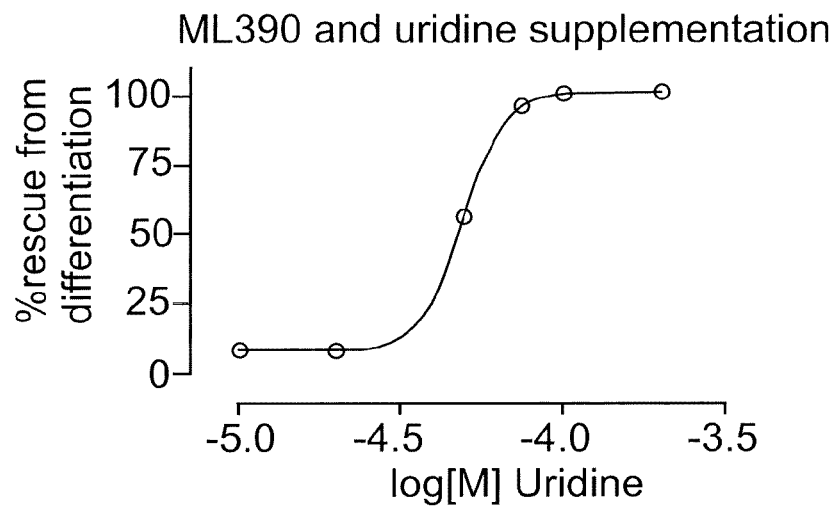
Figure 3G:
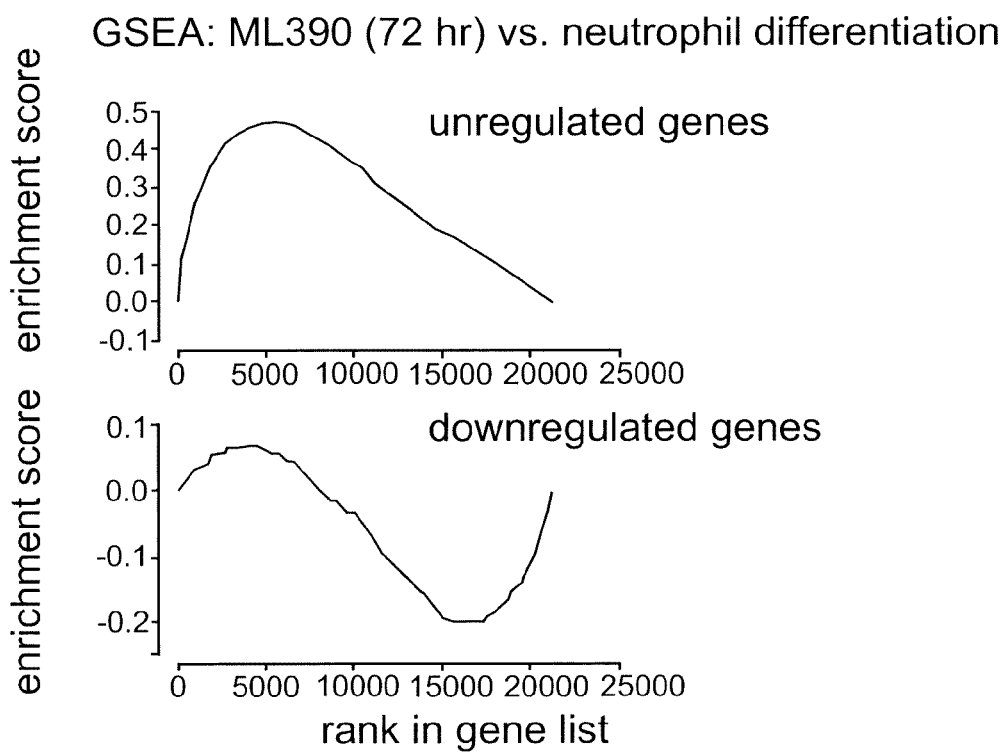
Figure 3H:
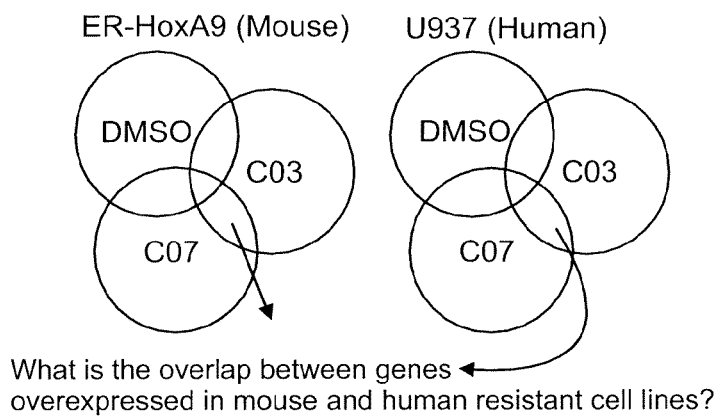
FIG. 3H provides a Ven diagram illustrating the overlap in genes overexpressed in mouse and human resistant cell lines.
Figure 3I:
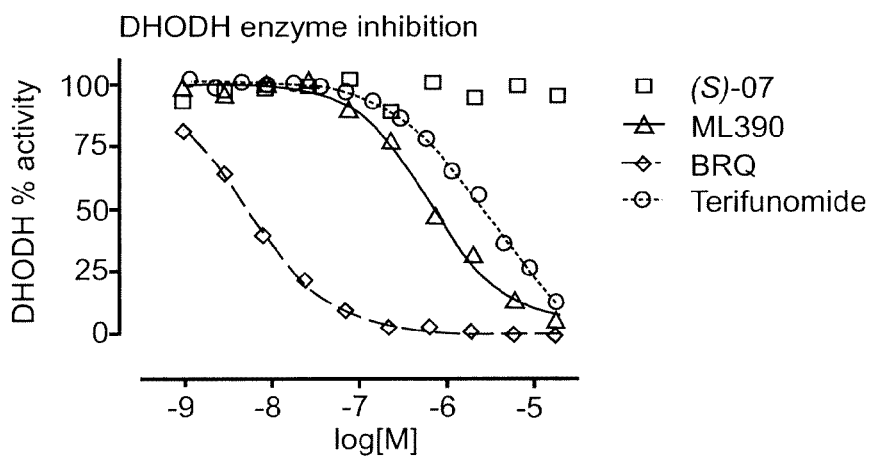
FIG. 3I is a graph showing DHODH enzyme inhibition in cells treated with brequinar (graph with rhombs) (BRQ), ML390 (graph with triangles), (S)-C07 (graph with squares), and teriflunomide (graph with dots).
Figure 3J:
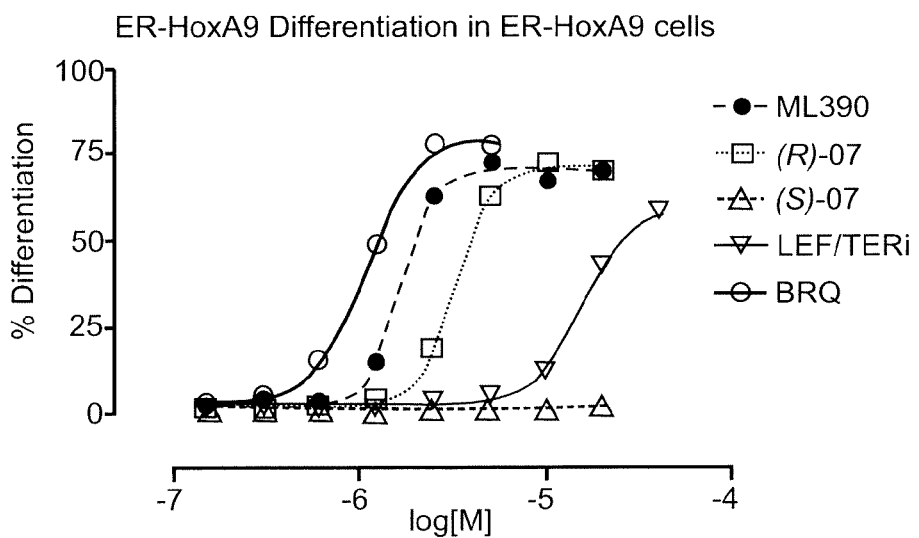
FIG. 3J is a graph showing percent differentiation in cells treated with brequinar (BRQ) (graph with black dots), ML390 (graph with lighter dots), (S)-C07 (graph with pointing up), (R)-C07 (graph with squares), and leflunomide (LEF)/teriflunomide (TERI)(graph with triangles pointing down).

The gene expression of our four resistant cell lines was analyzed by RNA-Seq, and compared the overlap of expression changes between cells resistant to C03 and (R)-C07 as well as the overlap between murine and human cells (FIG. 3H). The analysis revealed that only 8 shared genes were highly (>4-fold) upregulated among the C03-resistant and (R)-C07-resistant populations in both Lys-GFP-ER-HoxA9 and U937 cell lines (FIGS. 3I, 3J). Interestingly, these 8 transcripts were gene neighbors within the same 100 kb region of the long-arm of chromosome 16 (human) or chromosome 8 (mouse), suggesting chromosomal amplification as the mechanism of resistance. Analysis of the whole-exome sequencing (WES) data confirmed this hypothesis, demonstrating a higher degree of coverage within this region (FIGS. 3C, 3D). WES did not identify any consistent point mutations.

One of the amplified genes encoded the enzyme dihydroorotate dehydrogenase (DHODH), a critical enzyme in the intracellular de novo synthesis of pyrimidines. The enzyme is highly conserved between human and mouse (90% amino acid homology), consistent with the ability of C03 and (R)-C07 to trigger differentiation in both murine and human AML models.

C03 and (R)-C07 were inhibitors of DHODH as demonstrated using a recombinant human DHODH protein in an in vitro enzyme inhibition assay. The enzyme inhibitory activity ($IC_{50}$) closely paralleled the biological differentiation effect ($ED_{50}$) (FIG. 3E). Likewise, known inhibitors of DHODH including leflunomide, its active metabolite teriflunomide, and brequinar sodium were also active in both our enzyme-inhibition and cellular differentiation assays (FIGS. 3I, 3J).

While cells depend on DHODH for intracellular uridine synthesis, they can also salvage extracellular uridine through nucleoside transporters. Supplementing media with increasing concentrations of uridine abrogated the differentiation effect of C03 and (R)-C07 in the Lys-GFP-ER-HoxA9, U937, and THP1 cell lines (FIG. 3F shows the Lys-GFP-ER-HoxA9 cells). This "uridine rescue" demonstrated that the myeloid differentiation effect was completely due to interference with uridine monophosphate (UMP) synthesis (FIG. 5A) and does not involve an additional alternate mechanism unrelated to inhibition of DHODH.

Figure 3K:
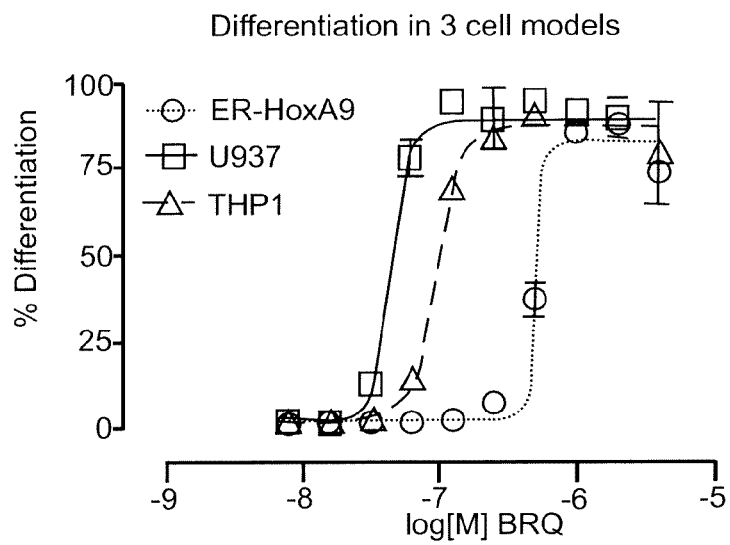
FIG. 3K a graph showing percent differentiation in ER-HoxA9 cells (graph with dots), U937 (graph with squares) and THP1 human leukemia cell lines (graph with triangels).
Figure 3L:
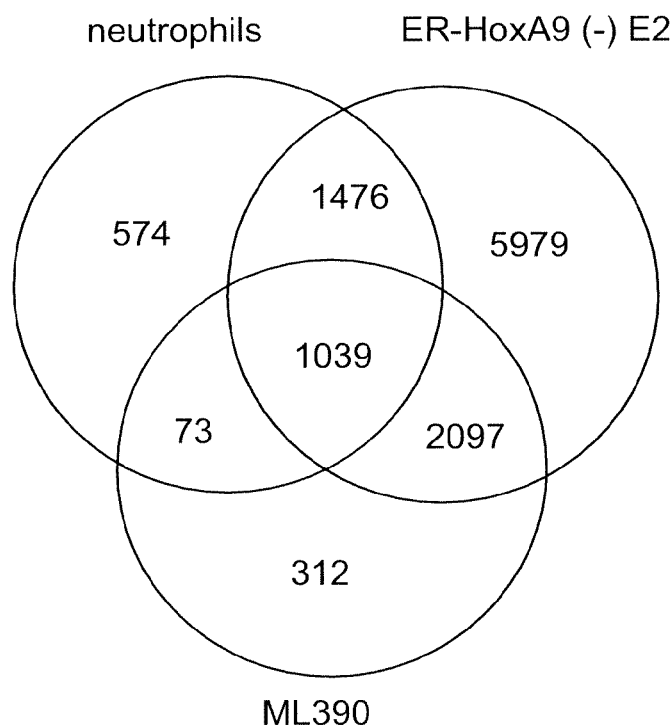
FIG. 3L provides a Ven diagram showing overlap in genes overexpressed in neutrophils vs. ER-HoxA9 cells in the absence of beta estradiol (–E2) vs. ER-HoxA9 cells treated with ML390.
Figure 3M:
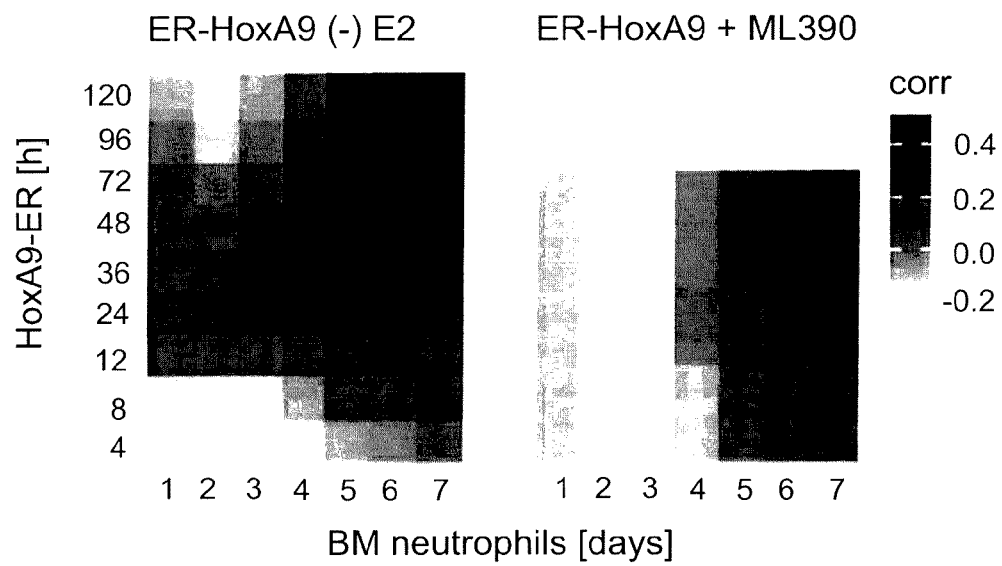
FIG. 3M is a heat map showing ER-HoxA9 cells in the absence of beta estradiol (–E2) vs. ER-HoxA9 cells treated with ML390.

Example 6: DHODH Inhibition Triggers a Gene-Expression Pattern Consistent with Myeloid Differentiation The gene-expression changes in Lys-GFP-ER-HoxA9 cells treated with ML390 for 12, 36, and 72 hours resembled the changes that accompany primary neutrophil differentiation (FIG. 3G). However, these patterns were less pronounced compared to those following inactivation of ER-HoxA9 (FIGS. 1F, 1I, 3M). Gene-expression changes following treatment with ML390 that were not observed during normal differentiation (FIG. 3L) were likely related to decreased pyrimidine availability and a global suppression of RNA and DNA synthesis.

Example 7: Brequinar Sodium, a Potent and Selective Inhibitor of DHODH, is Suitable for In Vivo Studies Because ML390's low solubility and bioavailability limited its potential as an in vivo tool compound, the suitability of other DHODH inhibitors for in vivo studies was evaluated. Brequinar sodium is a potent inhibitor of DHODH originally developed by DuPont Pharmaceuticals (DUP 785; NSC 368390) as an anti-proliferative agent. Brequinar inhibits DHODH activity in vitro with an $IC_{50}$ of <10 nM (FIG. 3I) and triggers differentiation in the ER-HoxA9, U937, and THP1 cells with an $ED_{50}$ of <1 µM (FIG. 3K). The potency of brequinar is dependent on extracellular concentrations of uridine; cells cultured in 50% FBS (to better approximate the extracellular plasma concentrations of uridine in vivo) showed a ~2-fold increase in their $ED_{50}$.

Figure 4A:
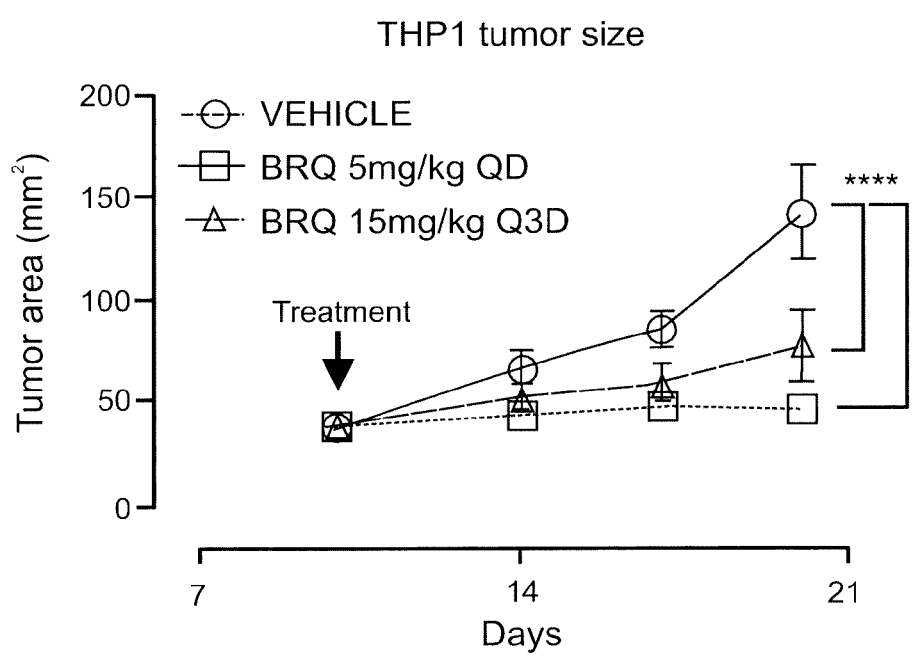
FIG. 4A-4D shows that brequinar causes differentiation and shows anti-tumor activity in an in vivo xenotransplant model of acute myeloid leukemia (AML).
Figure 4B:
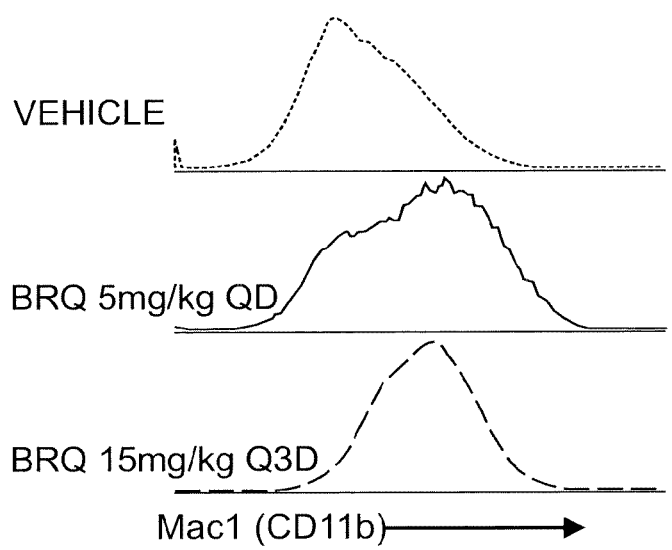
Figure 4C:
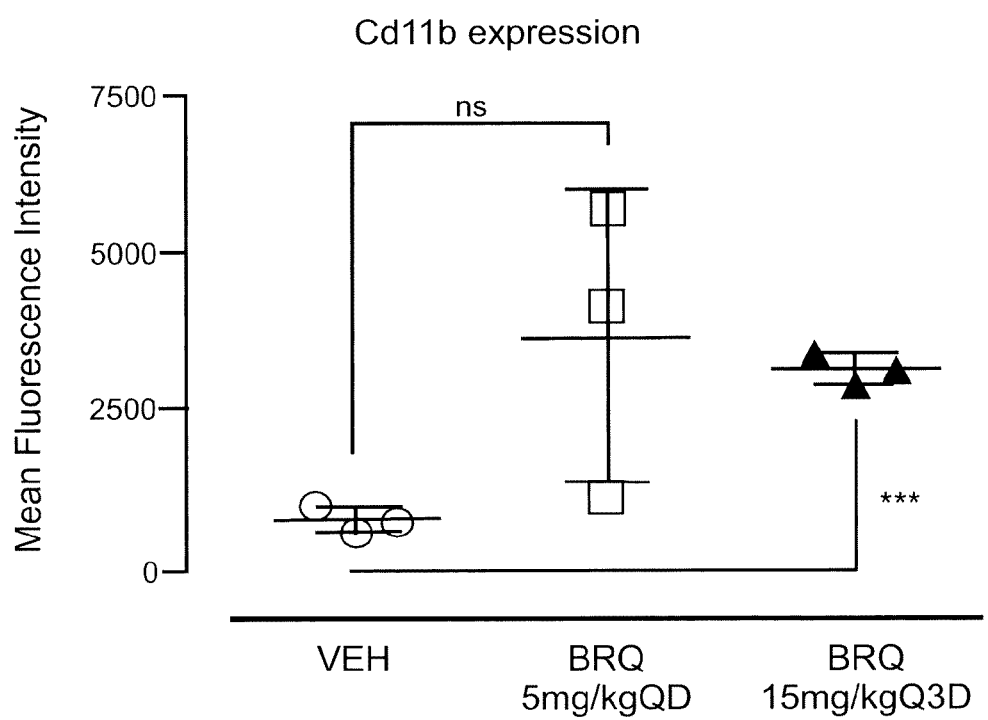
Figure 4D:
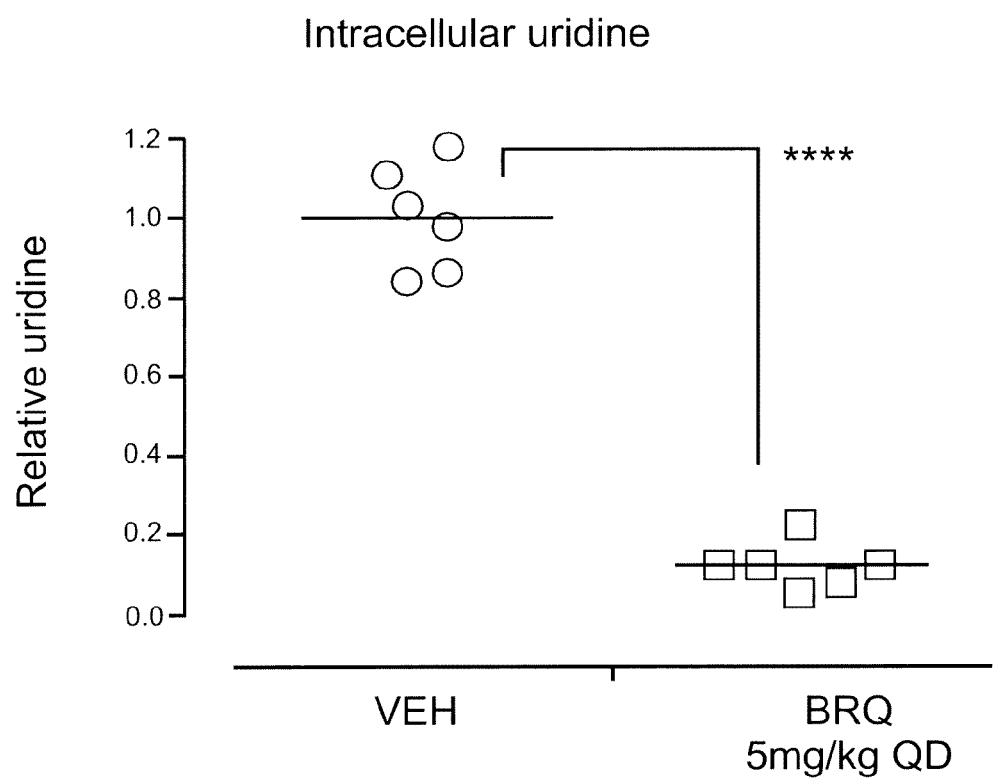
Figure 4E:
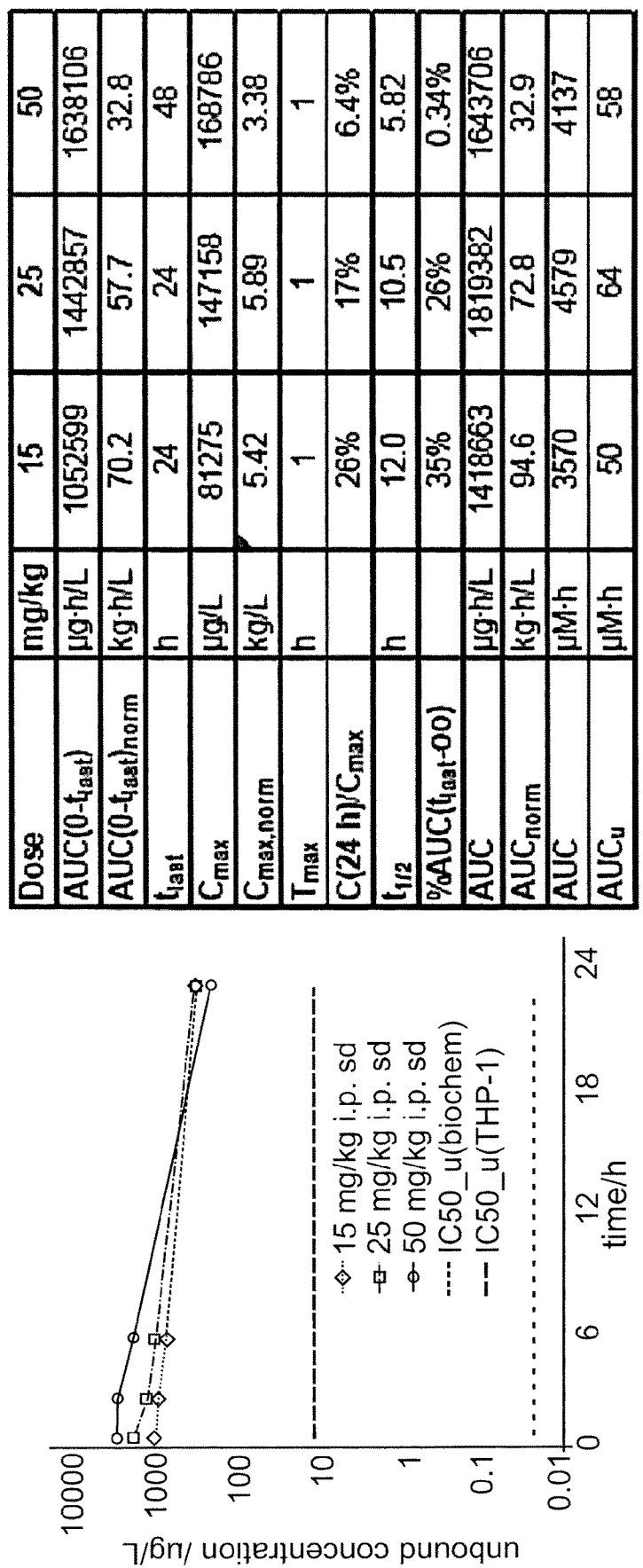
FIG. 4E an analysis of brequinar plasma concentration after a single IP dose (left: graph of plasma concentration; right: chart of pharmacokinetic data). From top to bottom: Continuous lines: Top graph for 50 mg/kg i.p. sd, below for 25 mg/kg i.p. sd and bottom graph, dotted lines: IC50_u (THP-1) and bottom line IC50_u(ubiochem), "unbound concentration [µg/L]".
Figure 4F:
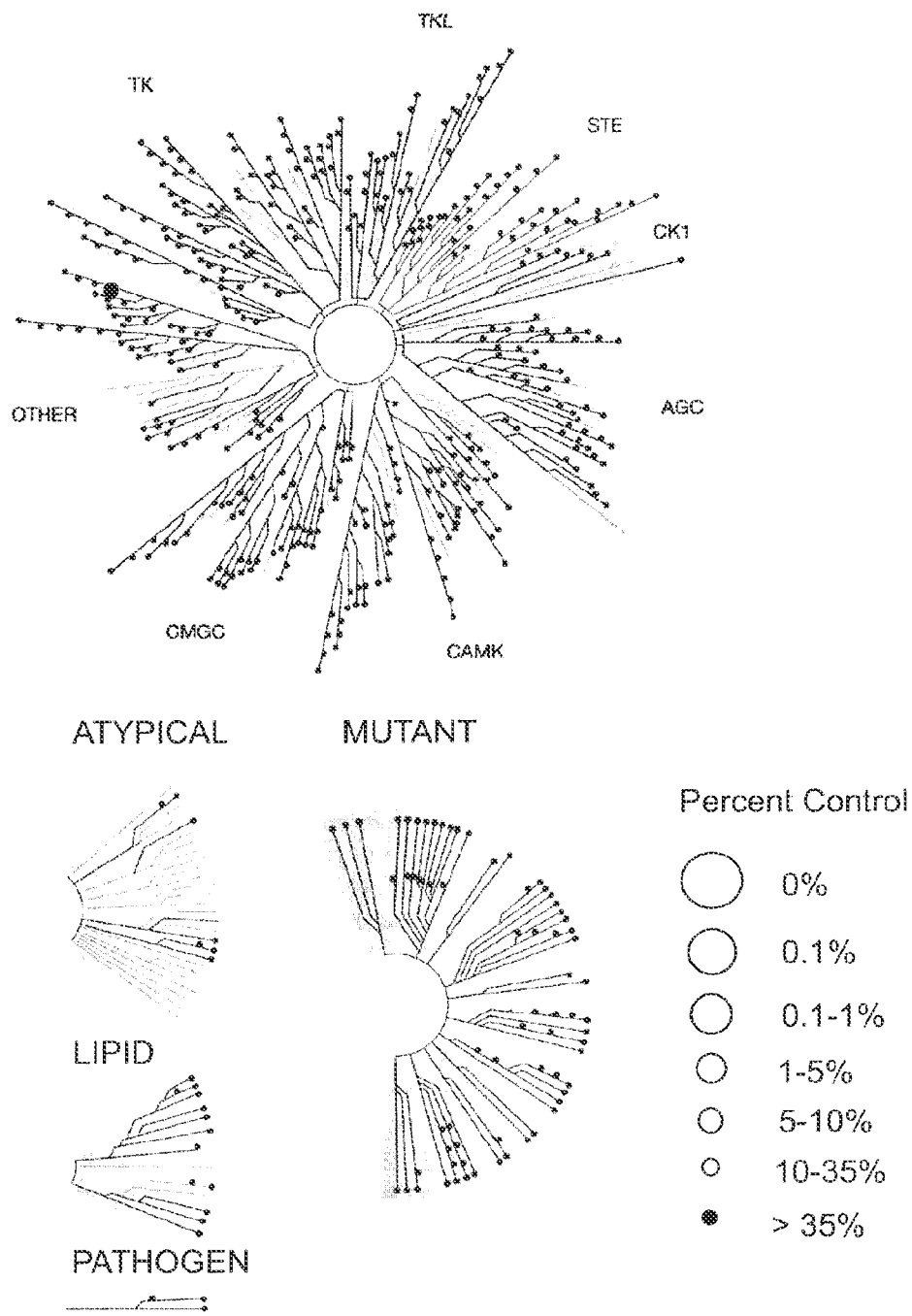
FIG. 4F provides an analysis of brequinar kinase inhibitory activity in the DiscoverX kinase assay.
Figure 4G:
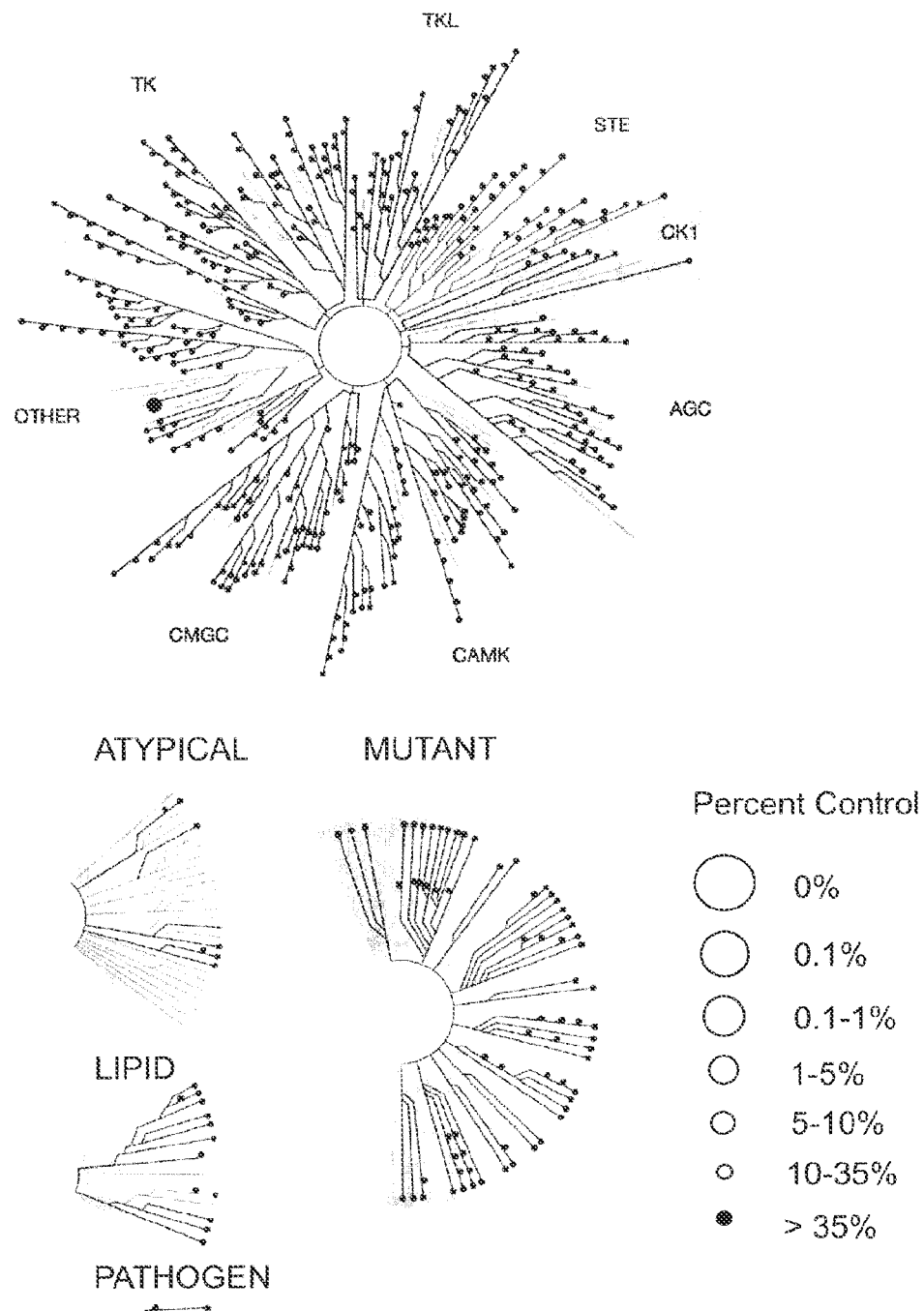
FIG. 4G provides an analysis of brequinar kinase inhibitory activity in the DiscoverX kinase assay.

Brequinar has a half-life of approximately 12 hours in vivo (FIG. 4E) and is highly protein-bound (98-99%), consistent with published literature (Cramer, 1995). To help exclude the possibility that brequinar was inhibiting kinases in addition to DHODH, we profiled brequinar against a panel of >400 known kinases (DiscoverX KinomeScan). Brequinar showed a near-complete absence of kinase inhibitory activity at 100 nM and 1 µM concentrations (FIG. 4F and 4G).

The maximum tolerated dose (MTD) of brequinar was evaluated in wild-type C57B1/6 mice (see, Example 21). When administered daily, brequinar was tolerated at doses up to 15 mg/kg. Mice receiving doses higher than 15 mg/kg exhibited both weight loss and thrombocytopenia after 6 days of daily dosing. This toxicity was reversible, and mice recovered fully following discontinuation of treatment. Measurements of plasma brequinar concentration after a single intraperitoneal (IP) dose of 15 mg/kg or 25 mg/kg suggested that an intermittent dosing schedule could also maintain concentrations above the in vitro cellular $ED_{50}$ of approximately 1 µM (FIGS. 3K, 4E). Furthermore, this intermittent schedule was better tolerated, and mice given doses up to 50 mg/kg once every three days (Q3D) showed no weight loss or thrombocytopenia.

Figure 4H:
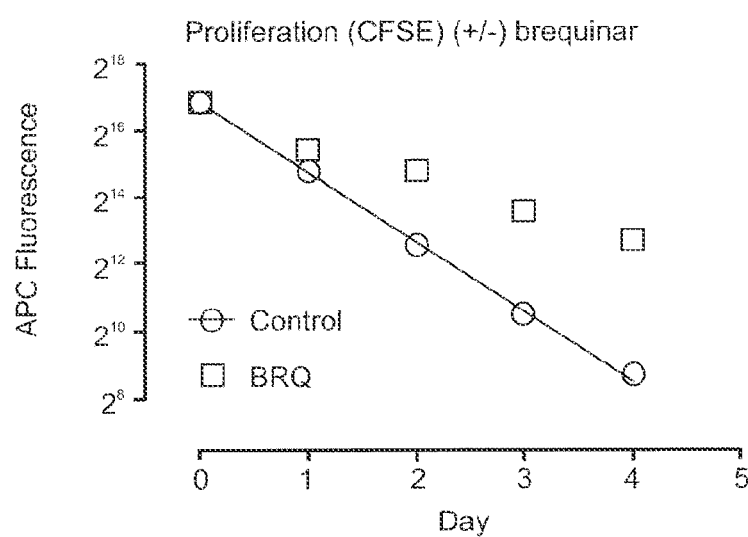
FIG. 4H is a graph showing proliferation in a carboxyfluorescein (CFSE) assay of tumor cells cultured in the presence or absence of brequinar, control graph with dots and BRQ graph with squares, "APC fluorescence" vs "day".

Example 8: Brequinar Demonstrates Anti-Leukemia Activity and Differentiation In Vivo in a THP-1 Xenograft Model of AML THP1 cells were implanted subcutaneously into the flank of SCID mice, and allowed 10 days to engraft to tumor size of ~40 mm². Mice were treated with vehicle control or brequinar given by IP injection at a dosage of 5 mg/kg daily or 15 mg/kg every third day (Q3D). Brequinar slowed tumor growth at the 15 mg/kg Q3D dosage and arrested tumor growth at the 5 mg/kg daily dosage (FIGS. 4A, 4H). THP1 tumors were explanted for differentiation analysis; THP1 cells from mice treated with brequinar exhibited marked differentiation as evidenced by their increase in CD11b expression (depicted graphically in FIG. 4B and by geometric mean fluorescence intensities in FIG. 4C).

Example 9: DHODH Inhibition Leads to a Depletion of Uridine and UDP-Metabolites In Vitro and In Vivo DHODH catalyzes the conversion of dihydroorotate (DHO) to orotate in the endogenous synthesis of uridine monophosphate (UMP, FIG. 5A). In vitro, the treatment of Lys-GFP-ER-HoxA9 cells with ML390 for 48 hours inhibited DHODH activity leading to the dramatic (>500-fold) accumulation of the upstream metabolite dihydroorotate (FIG. 5B) and to the depletion of uridine and other downstream metabolites (FIG. 5C).

Figure 5A:
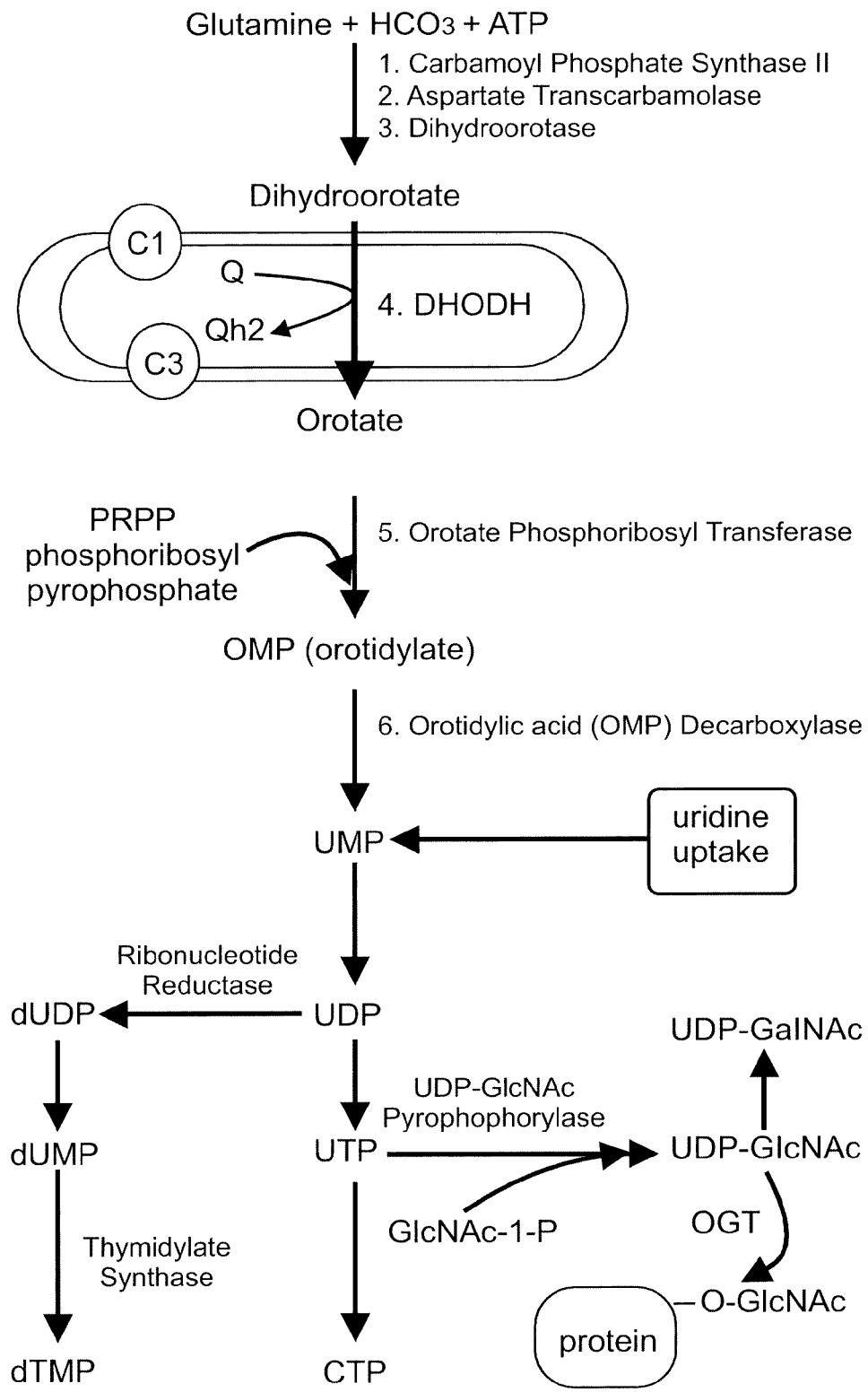
FIG. 5A-5E show that inhibition of DHODH leads to an accumulation of upstream metabolites and to a depletion of downstream metabolites.
Figure 5B:
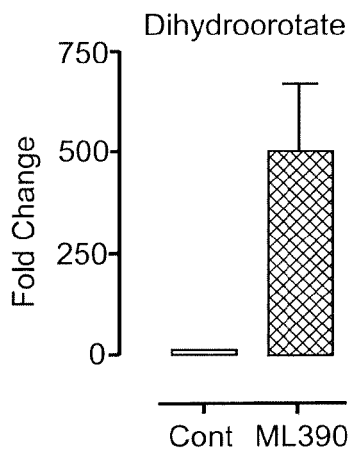
Figure 5C:
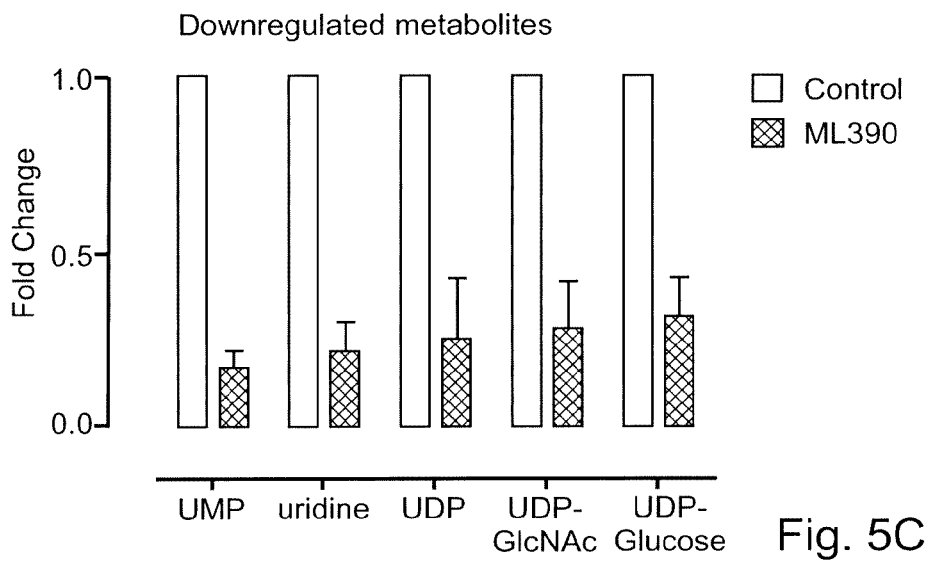
Figure 5D:
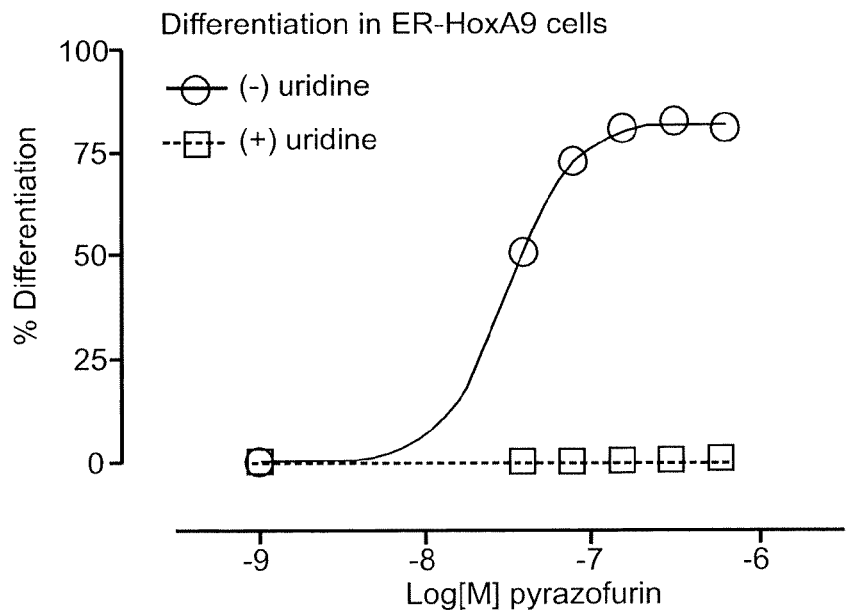

While DHODH catalyzes the fourth step of uridine biosynthesis, the enzyme OMP decarboxylase (OMPD) catalyzes the sixth step (FIG. 5A). Pyrazofurin is a potent small-molecule inhibitor of OMPD (Dix et al., 1979), and treatment of the Lys-GFP-ER-HoxA9 cells with pyrazofurin phenocopied the differentiation effect of DHODH inhibition (FIG. 5D). Uridine supplementation of the cell-culture medium abrogated the differentiation effect of ML390 or pyrazofurin (FIGS. 3G, 5D). Uridine supplementation also reversed the depletion of downstream metabolites, but did not reverse the accumulation of DHO. Together, these findings demonstrate that inhibition of UMP synthesis at two points along the pathway, but not the accumulation of dihydroorotate, leads to myeloid differentiation. Thus, while dihydroorotate is a marker of enzyme inhibition, it is not an oncometabolite such as in the case of 2-hydroxyglutarate (2HG) in patients with IDH-mutant leukemias (Ward et al., 2010). To confirm in vivo DHODH inhibition, cellular metabolite analysis of subcutaneous THP1 cells as well as HoxA9-Meis1 bone marrow leukemia cells was performed. THP1 cells isolated from BRQ-treated mice showed a significant (90% AUC) reduction in cellular uridine levels compared to vehicle-treated controls (FIG. 4D). In similar fashion, HoxA9-Meis1 leukemia cells isolated from the bone marrow of BRQ-treated mice also showed a significant reduction in cellular uridine in addition to UDP and UDP-glycoconjugates (e.g. UDP-GlcNAc, UDP-GalNAc).

Figure 5E:
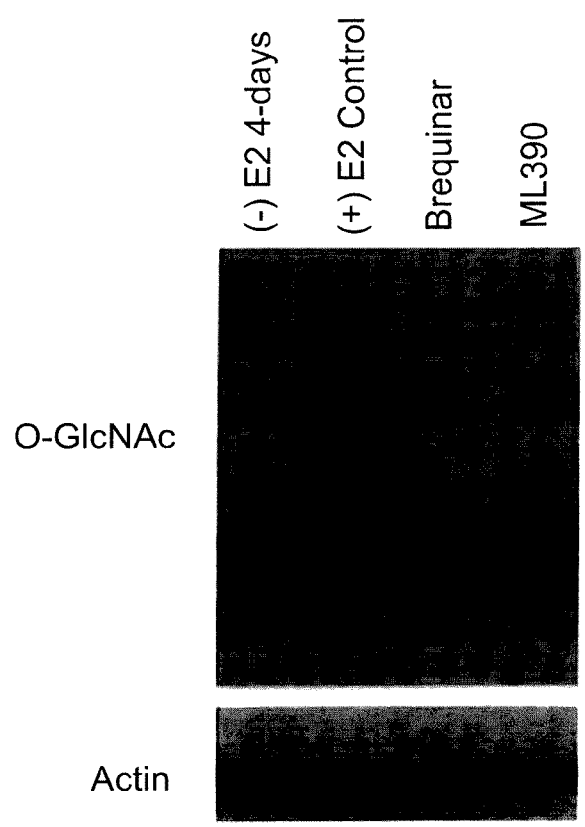

DHODH and OMPD inhibitors lead to depletion of uridine and to myeloid differentiation in model systems. However, downstream inhibitors of DNA and RNA biosynthesis (methotrexate, hydroxyurea) or DNA-damaging agents (cytarabine, daunorubicin) caused cytotoxicity without differentiation. (See, Example 24.) Without intending to be bound by theory, part of the differentiation effect may be due to depletion of UDP-GlcNAc leading to decreased O-linked N-acetylglycosylation (GlcNAc) post-translational modification of proteins. DHODH inhibition with ML390 or BRQ led to a global reduction of protein O-GlcNAc modification (FIG. 5E).

Figure 6A:
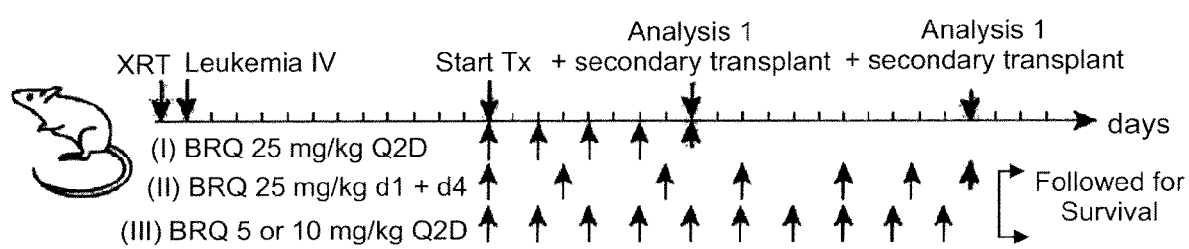

Example 10: Brequinar Demonstrates Anti-Leukemia Activity and Differentiation In Vivo in a Syngeneic HoxA9 Model of AML To address the anti-leukemic and differentiation effect of DHODH inhibition in vivo, we chose a syngeneic retroviral transduction model of AML. In this model, bone marrow cells are transduced with MSCV-based retrovirus expressing both HoxA9 and Meis1 oncoproteins and introduced intravenously into recipient mice that have been pre-conditioned with a sub-lethal dose of radiation. Mice that developed acute myeloid leukemia were sacrificed and bone marrow cells were expanded in vitro in media supplemented with SCF and IL-3. To permit easy tracking in vivo, leukemic cells were transduced with lentivirus expressing the Venus fluorescent protein, and double-sorted by fluorescence activated cell sorting (FACS) to purity. These Venus-expressing cultured leukemic cells were re-transplanted into pre-conditioned secondary recipient mice, and these secondary recipients were used in all described experiments. IP treatment with brequinar or vehicle was initiated after 14 days, when the burden of leukemic blasts in the bone marrow was approximately 5% (FIG. 6A). Mice were treated at six dosages: (1) vehicle Q2D, (2) BRQ 5 mg/kg Q2D, (3) BRQ 10 mg/kg Q2D, (4) BRQ 25 mg/kg Q2D, (5) vehicle days 1+4 of a 7-day schedule or (6) BRQ 25 mg/kg days 1+4 of a 7-day schedule. Scheduled interim euthanasia and leukemia analyses were performed at two planned time points (FIG. 6A).

Figure 6B:
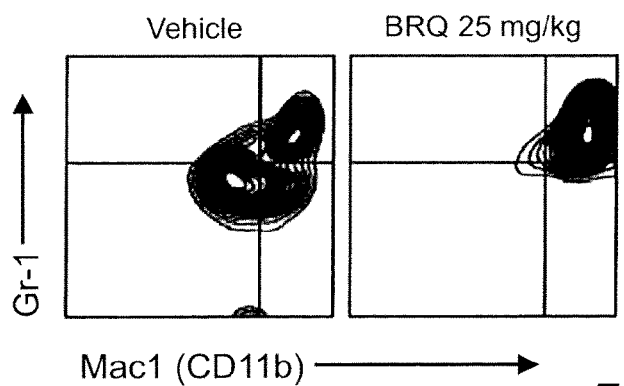
Figure 6C:
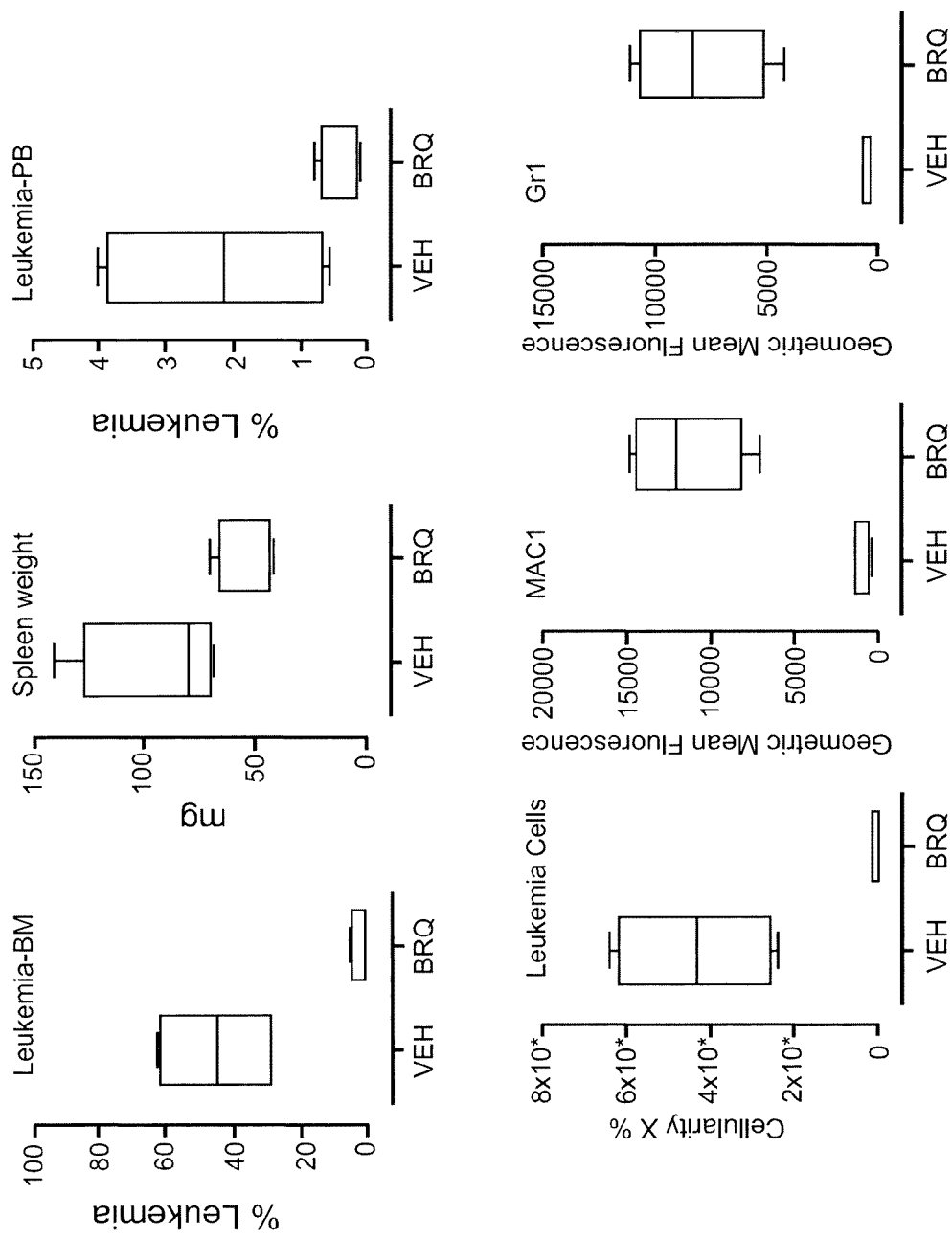

The first analysis and secondary transplant were performed following BRQ 25 mg/kg given Q2D for four doses. Given the intensity of this regimen, the mice demonstrated side effects of weight loss, anemia, and thrombocytopenia (FIG. 6A). Similar to the differentiation effect of BRQ in vitro, leukemic cells were more mature as evidenced by upregulation of differentiation markers CD11b (Mac-1) and Gr-1 (Ly6C/G) (FIG. 6B). Mice treated with BRQ showed a dramatic decrease in the leukemic involvement of their bone marrow, spleen, and peripheral blood (FIG. 6C).

Figure 6D:
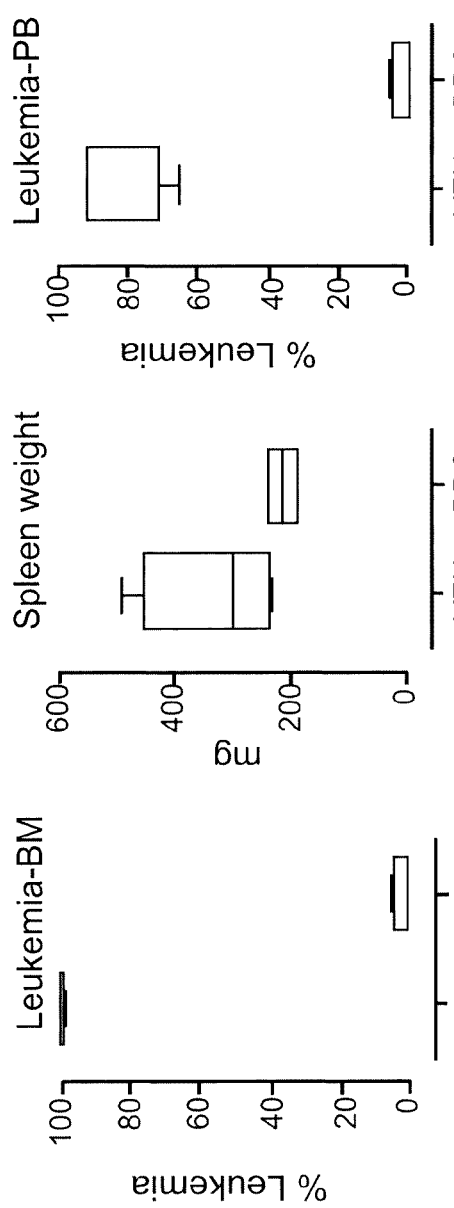
Figure 6D:
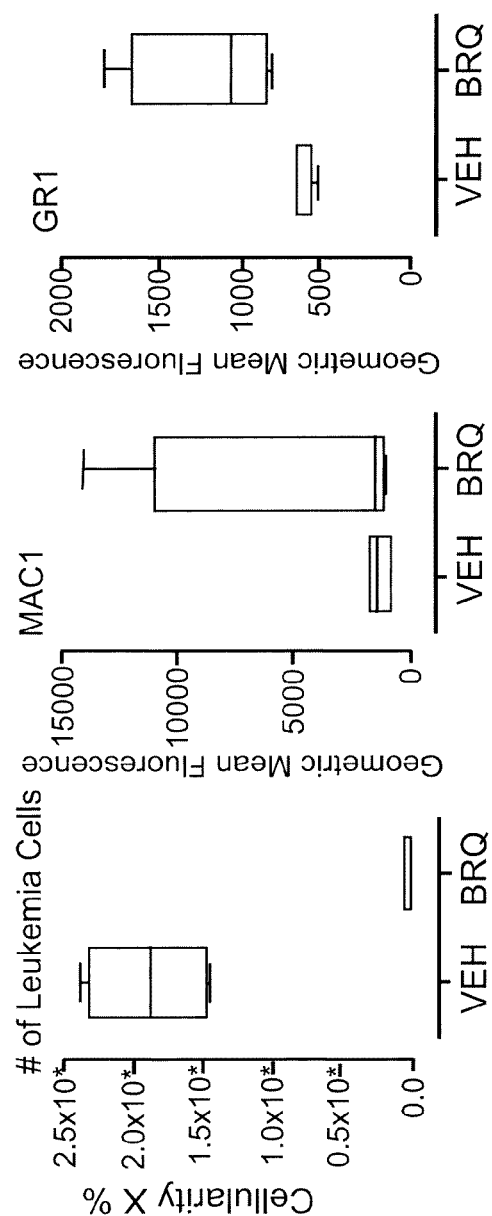

The second analysis and secondary transplant were performed at the time when the vehicle-control mice exhibited signs of terminal leukemia (e.g. ruffled fur, decreased activity, weight loss). This group had received BRQ 25 mg/kg given day 1+4 of a 7-day schedule for a total of 6 doses. Remarkably, the mice treated on this extended schedule demonstrated none of the side effects of mice treated on the every-other-day schedule (FIGS. 6E, 6F). Furthermore, mice treated with brequinar showed an even more dramatic decrease in the leukemic involvement of their bone marrow, spleen, and peripheral blood (FIG. 6D).

Treatment of mice with BRQ 5 mg/kg or 10 mg/kg every other day led to a prolongation of survival (FIG. 6E, left panel). This treatment was well tolerated without hematologic toxicity or weight loss. Treatment of mice with BRQ 25 mg/kg given day 1+4 of a 7-day schedule led to an even more dramatic prolongation of survival (FIG. 6E, right panel), again without toxicity. (See, Example 24.) In this treatment group, the decision was made to discontinue treatment after 14 doses of BRQ (day 59). The mice eventually relapsed with leukemia after approximately 4 weeks off of treatment.

Figure 7A:
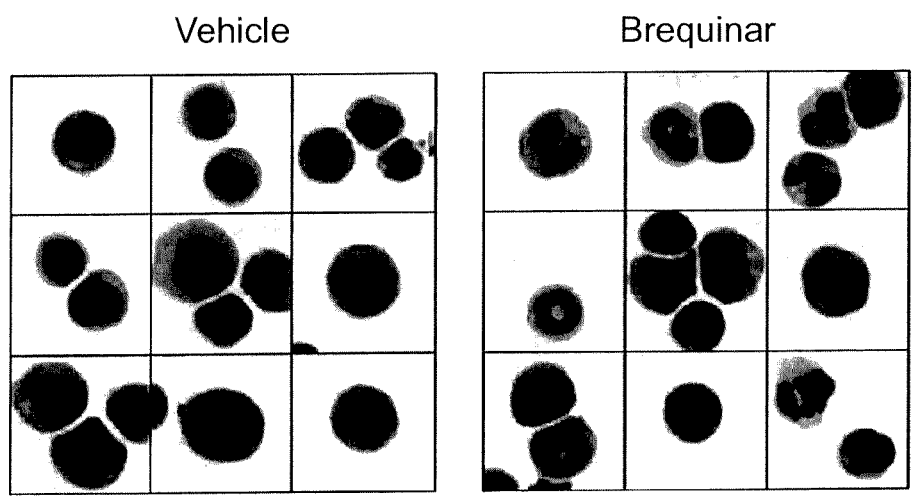
FIG. 7A-7B show that brequinar triggers morphologic evidence of differentiation in vivo and leads to a depletion of leukemia-initiating cell activity.

Example 11: DHODH Inhibitors Cause Differentiation and Depletion of Leukemia Initiating Cell Activity In Vivo Leukemic cells isolated from the BRQ-treated mice were more differentiated on the basis of their CD11b and Gr-1 cell-surface expression (FIGS. 6C, 6D). To assess their morphology as well as their functional potential as leukemia initiating cells, live Venus-positive leukemic cells were freshly isolated from vehicle or BRQ-treated mice by fluorescence-activated cell sorting (FACS). Wright-Giemsa-stained cytospin preparations of leukemic cells demonstrated that, in aggregate, cells isolated from BRQ-treated mice exhibited morphologic granulocytic differentiation, with signs of nuclear condensation (FIG. 7A).

Figure 7B:
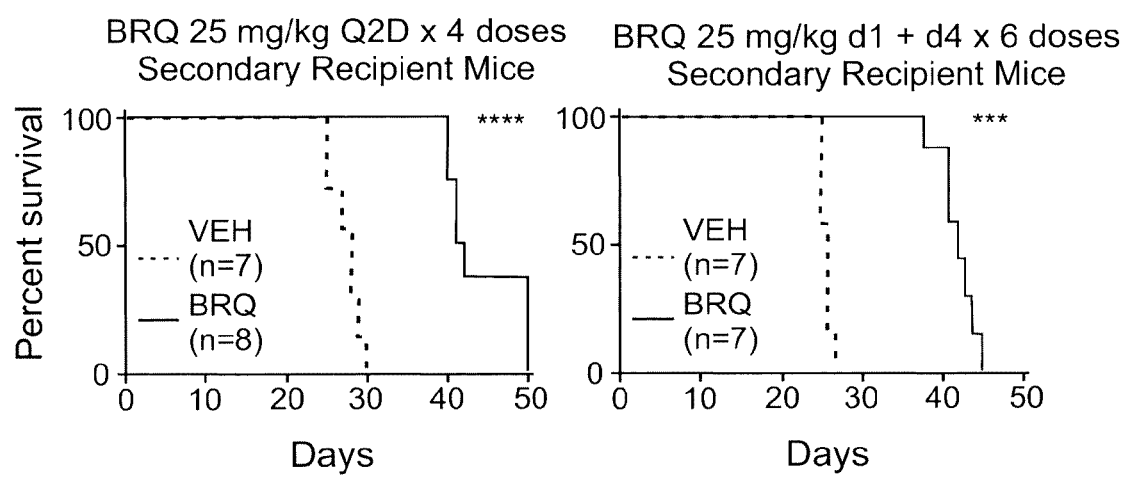

FACS-purified leukemia cells from vehicle or BRQ-treated mice were re-introduced into sub-lethally irradiated tertiary recipient mice. The experiment was performed twice: from mice that received BRQ 25 mg/kg every other day for 4 doses (FIG. 7B, left panel), and from mice that received BRQ day 1+4 of a 7-day cycle for a total of 6 doses (FIG. 7B, right panel). In both cases, mice that received the same number of live leukemic cells from BRQ-treated primary donors took longer to develop symptoms of leukemia, consistent with a decrease in leukemia-initiating cell potential.

When DHODH inhibitors were administered to mice on a daily basis, the mice became severely anemic, exhibited severe thrombocytopenia, and died after about 10-days of treatment. In contrast, when brequinar was administered every 3-days in a mouse model of acute myeloid leukemia, brequinar was well-tolerated and effective. To explore this observation, plasma levels of brequinar, dihydroorotate (DHO), and uridine were analyzed. DHODH catalyzes the conversion of dihydroorotate (DHO) to orotate in the endogenous synthesis of uridine monophosphate. Inhibition of DHODH activity results in dihydroorotate accumulation and uridine depletion.

Figure 8:
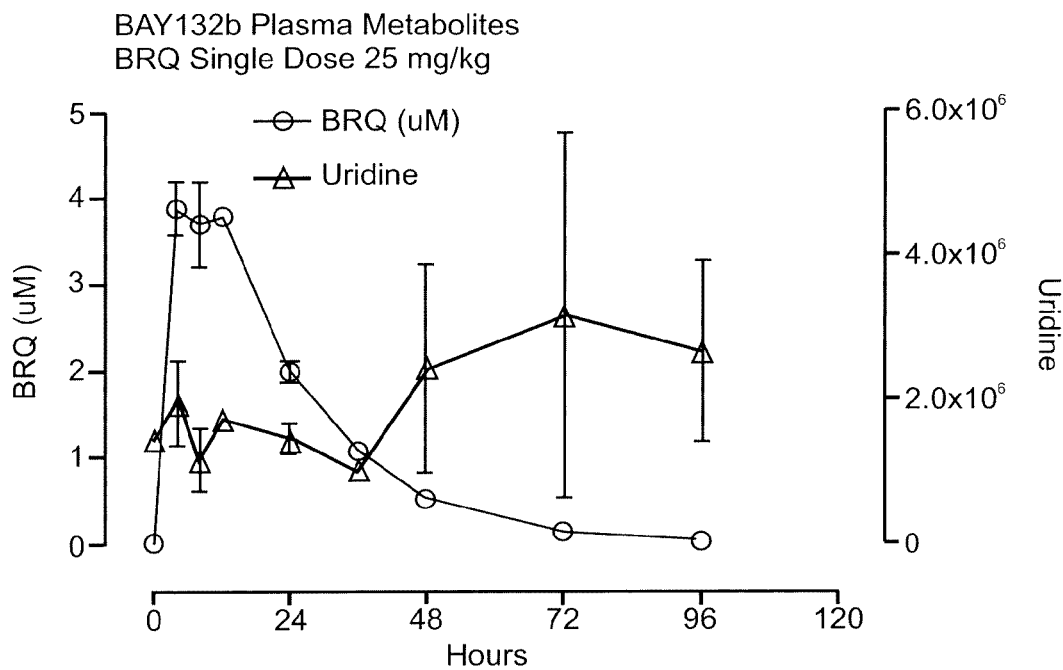
FIG. 8 is a graph showing levels of plasma uridine following a single 25 mg/kg dose of brequinar (BRQ). Brequinar was administered to a syngeneic murine model of acute myeloid leukemia (AML) (Time 0, graph with dots). Plasma levels of uridine were analyzed thereafter (graph with triangles), "Brequinar [uM]" and "uridine[z.y x 106]" vs "hours".
Figure 9:
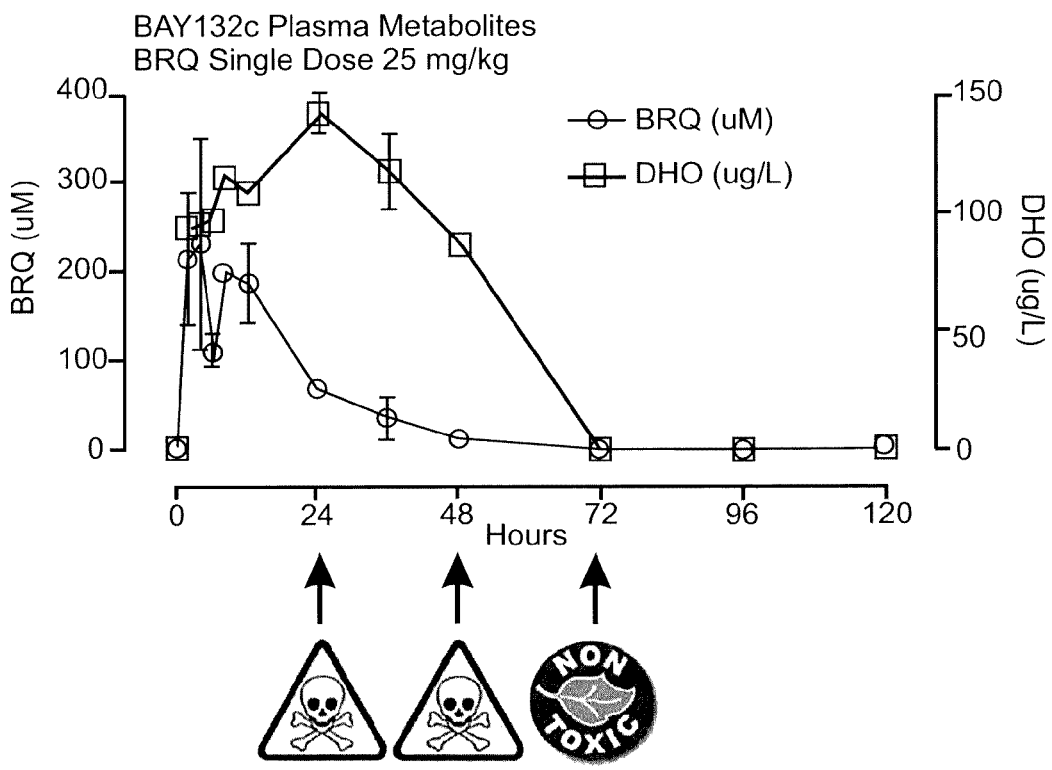
FIG. 9 is a graph showing levels of dihydroorotate (DHO) following a single 25 mg/kg dose of brequinar. Levels of DHO fell to undetectable levels within 72 hours of brequinar administration, DHO [ug/L] graph with squares, BRQ [uM] graph with dots, "BRQ[uM]" and DHO[uM/L] vs hours.
Figure 10:
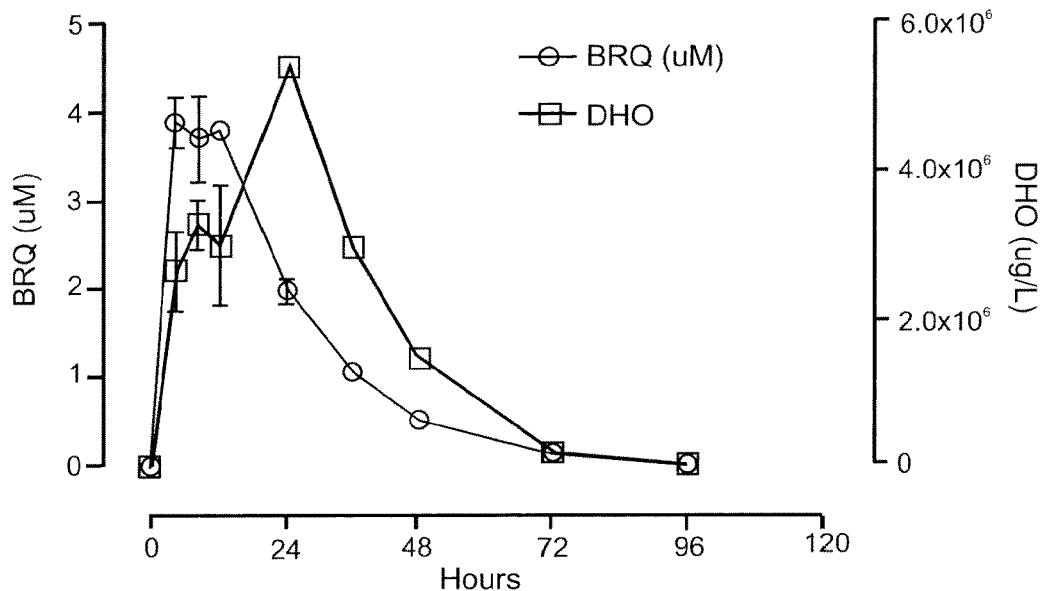
FIG. 10 includes two graphs (top) showing DHO levels following a single 25 mg/kg dose of brequinar and a third graph (bottom) showing fold-change in DHO following administration of DHODH inhibitor, ML390(right), or control (left).
Figure 10:
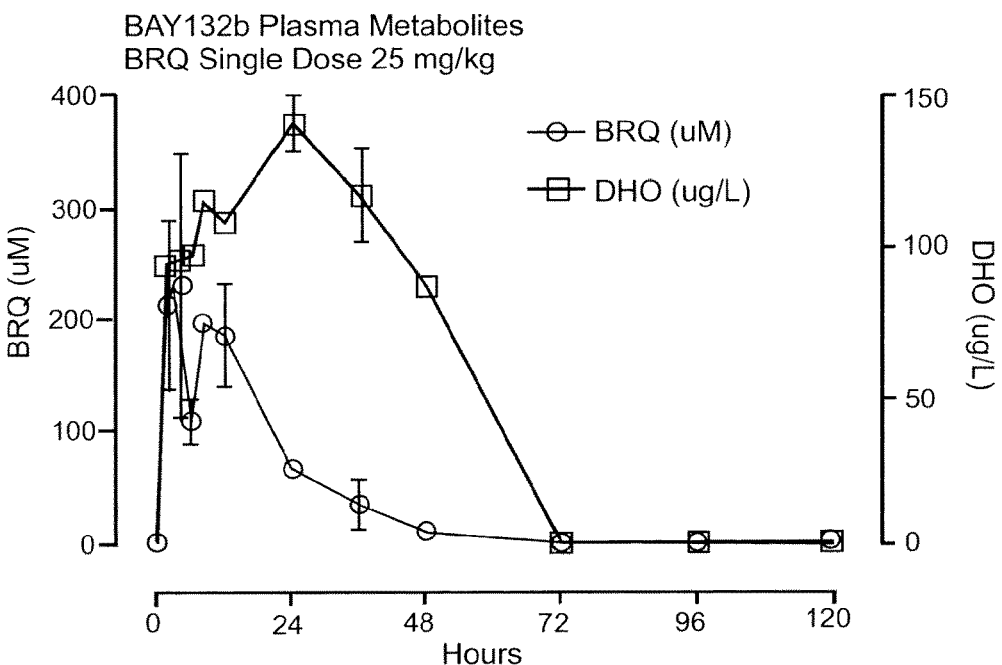
Figure 10:
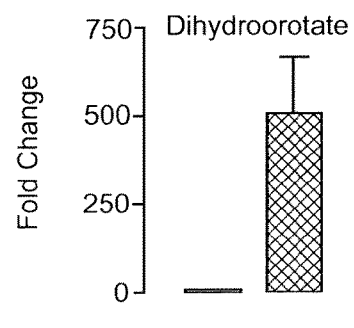
Figure 11:
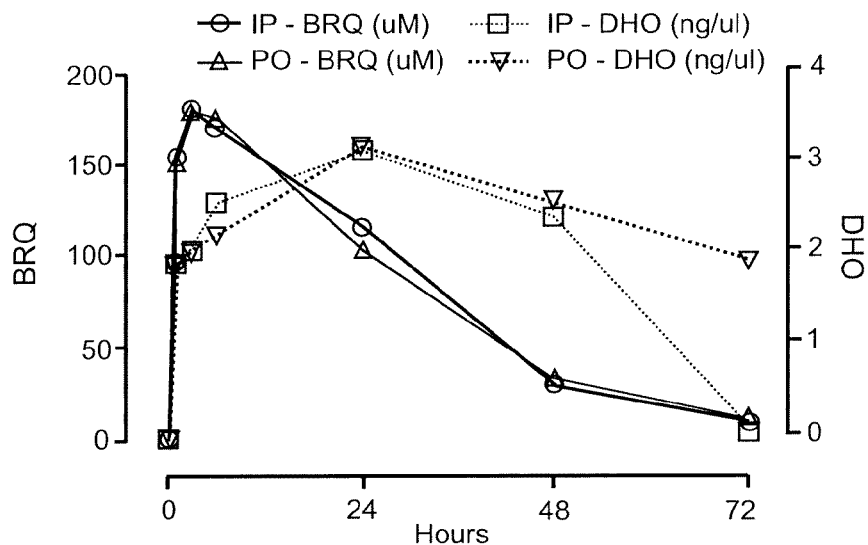
FIG. 11 is a graph showing that the change in DHO levels was similar regardless of whether brequinar administration [uM] was interperitoneally (IP, graph with dots) or by mouth (PO graph with triangles pointing up), dotted graphs DHO [ng/ul] (IP graph with squares), (PO graph with triangles pointing down).
Figure 12:
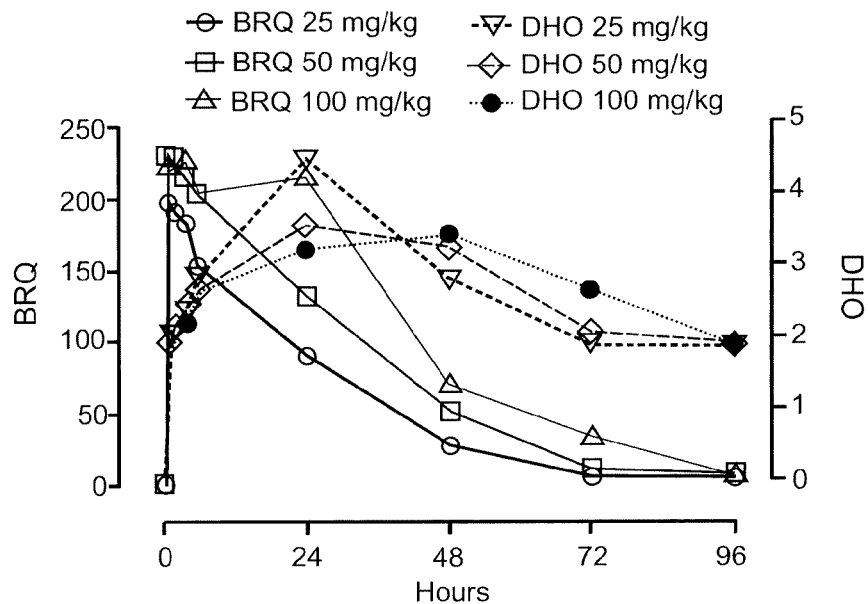
FIG. 12 is a graph showing that similar changes in DHO levels occurred at 25, 50, or 100 mg/kg. Shown Brequinar: 25 (graph with light dots), 50 (graph with squares), or 100 mg/kg (graph with triangles pointing up), for DHO: dotted graphs, 25 (graph with triangles pointing down), 50 (graph with rhombs) and 100 mg/kg (graph with black dots), "BRQ" and "DHO" vs "hours".
Figure 13:
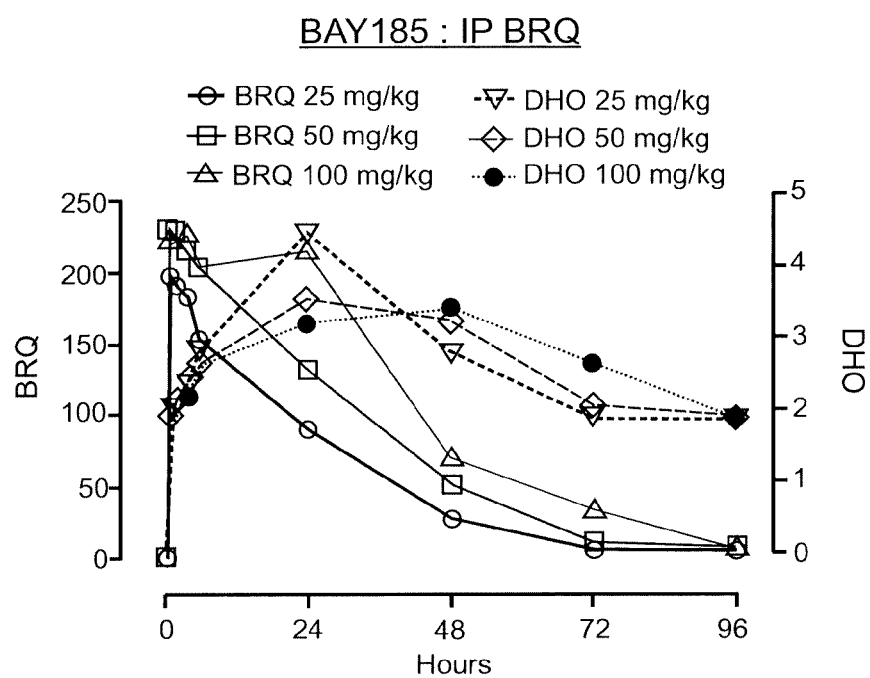
FIG. 13 is a graph showing that a similar time above threshold was observed at 3 different dosages of brequinar administered interperitoneally (IP).

A single dose of brequinar (25 mg/kg) was administered to a syngeneic murine model of acute myeloid leukemia (AML). Plasma uridine levels were analyzed at various times thereafter (FIG. 8). Plasma uridine decreased initially, and rebounded after about 48 hours. DHO levels were undetectable at time 0 (FIG. 9). DHO accumulated rapidly, but within seventy two hours of brequinar administration, DHO levels were once again undetectable (FIG. 9, FIG. 10). These results indicate that plasma levels of DHO alone or in combination with uridine can be used as a marker for DHODH activity. Administration of a DHODH inhibitor should be timed to allow DHO to return to baseline prior to administering a further dose of DHODH inhibitor. This will maximize efficacy and minimize adverse side effects, including risk of death. Patient-specific dosing will be accomplished by adjusting the dose of DHODH inhibitor based on the patient's metabolism. This will involve adjusting the dosage based on the measurement of plasma DHO. This will maximize the efficacy and minimize the toxicity.

Reported herein is a novel model system of conditional myeloid differentiation using an estrogen-dependent form of the homeobox protein HoxA9. When expressed in primary murine bone marrow mononuclear cells from a Lysozyme-GFP knock-in mouse, ER-HoxA9 generates factor-dependent granulocyte-monocyte progenitor (GMP) cell lines that undergo normal, synchronous, and terminal neutrophil differentiation upon inactivation of ER-HoxA9. The cells provide an unlimited source of myeloid progenitors for the study of normal myelopoiesis as well as an unlimited supply of model leukemic granulocyte-monocyte progenitors (GMPs) to identify small molecules that overcome differentiation arrest. Using these cells, an unbiased small-molecule phenotypic screen for compounds that could trigger myeloid differentiation was performed.

This is the first use of an estrogen-dependent HoxA9 system of conditional myeloid differentiation as a model of myeloid differentiation arrest. The most potent bioactive compounds were identified as inhibitors of the enzyme dihydroorotate dehydrogenase (DHODH). In fact, 11 of the 12 hits from a library of more than 330,000 compounds were inhibitors of DHODH, highlighting the unanticipated finding that the pyrimidine biosynthetic pathway serves as a regulator of myeloid differentiation. This study stresses the importance of phenotypic screens, as compared to target-based screens, in the identification of novel and relevant protein targets in oncology and demonstrates that they can reveal novel biology about the disease. The difficulty in a phenotypic screen is often one of target identification. Cell lines with acquired resistance to the differentiation effects of small molecules were used to determine the mechanism of action.

DHODH catalyzes the fourth step in pyrimidine synthesis, the conversion of dihydroorotate to orotate. The enzyme is located in the inner mitochondrial membrane and transfers electrons between dihydroorotate and complex 3 of the electron-transport chain via the reduction of its ubiquinone (CoenzymeQ$_{10}$) cofactor. Its role in electron transport is not thought to be associated with the in vitro myeloid-differentiation effect because inhibition of the downstream enzyme OMPD (which is not involved in electron transport) phenocopies the differentiation effects of DHODH inhibition.

DHODH is important during development, and a complete lack of enzyme activity is not compatible with life (murine or human). The Miller syndrome is a rare autosomal recessive disorder in which patients have inherited hypomorphic mutations in both alleles of DHODH, resulting in multi-organ dysfunction. Though ubiquitously expressed, mutations in DHODH in the context of malignancy have not been reported. Of peripheral interest, DHODH is also recognized as an anti-malarial drug target given the ability to design small molecules that specifically bind and inhibit *Plasmodium falciparum* DHODH without inhibiting the human enzyme.

Two inhibitors of human DHODH have been approved for clinical use in humans. Leflunomide is a pro-drug that is effective as a disease-modifying and anti-inflammatory agent in the treatment of patients with rheumatoid arthritis. Its active form teriflunomide was also approved for the treatment of patients with multiple sclerosis. Leflunomide and teriflunomide are weak inhibitors of DHODH (IC$_{50}$~5 µM), are readily bioavailable, have long half-lives, and are well tolerated.

Leukemic (HoxA9 and Meis1-expressing) mice were treated with leflunomide. At the highest dosage, leflunomide (25 mg/kg daily) treatment resulted in a very mild increase in the expression of the differentiation marker CD11b, but did not result in a reduction in leukemic burden. Furthermore, it was poorly tolerated at this dosage, causing weight loss and lethargy in recipient mice.

Brequinar is a potent (IC$_{50}$~20 nM) and specific inhibitor of DHODH that was developed by DuPont Pharmaceuticals (DUP 785, NSC 368390). Brequinar was not studied in the context of patients with leukemia or with other hematologic malignancies. In model systems described herein, sustained exposure to brequinar was required for its myeloid differentiation effect in vitro; brequinar pulses that lasted fewer than 48-hours had almost no effect. Without intending to be bound by theory, it may be that prolonged suppression of uridine production is required to kill cancer cells, or to induce AML differentiation, in vivo.

Brequinar was evaluated as an immunosuppressive agent, alone and in combination with cyclosporine and FK506. Brequinar was effective in preventing organ rejection in pre-clinical transplant models, consistent with the hypothesis that activated T-cells have a 2-fold expansion of their purine (ATP, GTP) pools and an 8-fold expansion of their pyrimidine (UTP, UDP-glucose, CTP) pools, pointing towards a potential sensitivity of activated lymphocytes to inhibitors of endogenous pyrimidine synthesis (Fairbanks et al., 1995).

Results reported herein show that brequinar and other DHODH inhibitors triggered myeloid differentiation in vitro and in vivo, and led to the depletion of functional leukemia-initiating cells in vivo. Wild-type mice bearing syngeneic leukemia and immunocompromised mice implanted with human xenografts (THP1) tolerated extended doses of brequinar. Without intending to be bound by theory, it is likely that there is a differential sensitivity to DHODH inhibition between normal and malignant cells in vivo. This observation points to a therapeutic window in the treatment of patients with acute myeloid leukemia.

What could be the biological basis of a therapeutic window in the context of an enzyme that is ubiquitously expressed in normal and malignant cells? DHODH inhibition leads to the depletion of pyrimidine precursors and therefore inhibits nucleic acid synthesis. Unlike traditional anti-metabolite purine and pyrimidine analog chemotherapies that lead to cumulative DNA damage, DHODH inhibition results in periods of nucleotide depletion, driving a dependency on salvage pathways or autophagy. Efficacy in model systems was observed from extended pulsatile (Q2D or Q3D) brequinar exposure. Without wishing to be bound by theory, this may be attributed to the differential sensitivity of malignant cells as compared to normal cells to intermittent periods of nucleotide 'starvation'. This would be consistent with the importance of dose schedule in the mouse model, where a high dose administered every three days demonstrates a potent anti-leukemia effect without the weight loss and thrombocytopenia that was observed with daily dosing.

Without wishing to be bound by theory, the observation that the differentiation effect can be phenocopied by pyrazofurin, an inhibitor of OMPD, but not by cytarabine, hydroxyurea or methotrexate, implicates upstream depletion of uridine/UMP/UDP as being of specific importance in the differentiation effect. One intriguing potential mechanism of differentiation is the alteration of O-linked N-acetylglycosylation, a common protein post-translational modification. The enzyme O-GlcNAc transferase (OGT) is a ubiquitous enzyme that transfers GlcNAc from UDP-GlcNAc to serine and threonine residues, and this modification can compete with other modifications including phosphorylation in the regulation of protein function. Particularly interesting proteins that undergo GlcNAc post-translational modification include Akt, the TET family of proteins, and c-Myc (reviewed in (Hanover et al., 2012; Jóźwiak et al., 2014)). Inhibition of DHODH lead to a global decrease in protein N-acetylglycosylation, and future work will help to elucidate whether any specific protein modifications are critical to the differentiation phenotype.

The efficacy of differentiation therapy in the treatment of leukemia has been proven by the overwhelming benefits of the small molecules all-trans retinoic acid (ATRA) and arsenic trioxide (As2O3) in those patients with PML/RAR-alpha translocations and acute promyelocytic leukemia. The lack of differentiation therapy for other forms of non-APL AML has been hampered by imperfect model systems. Reported herein is a novel phenotypic screening system that led to the unexpected identification of DHODH as a potential therapeutic target in AML, and identification of the efficacy of DHODH-inhibition in vitro and in animal models of syngeneic and xenotransplant AML.

This work highlights the importance of phenotypic screens in identifying previously unrecognized molecular pathways relevant for normal and malignant cell biology.

Chemical Examples

All reactions were carried out under nitrogen ($N_2$) atmosphere. All reagents and solvents were purchased from commercial vendors and used as received. NMR spectra were recorded on a Bruker 300 (300 MHz $^1$H, 75 MHz $^{13}$C, 282 MHz $^{19}$F) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Flash chromatography was performed using 40-60 μm Silica Gel (60 Å mesh) on a Teledyne Isco Combiflash $R_f$. Tandem Liquid Chromatography/Mass Spectrometry (LC/MS) was performed on a Waters 2795 separations module and 3100 mass detector.

Example 12: Synthesis of Compound C03

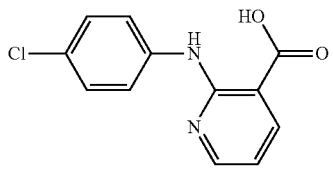

Compound C03 was synthesized following a literature procedure (*J. Org. Chem.* 2006, 71, 3270): To 4 mL of n-butanol was added 1.0 g of 2-chloronicotinic acid (6.4 mmol), 1.6 g of 4-chloro aniline (13 mmol), 1.3 g of $K_2CO_3$ (9.5 mmol), and 40 mg of copper powder (640 mmol) and the mixture was heated at 130° C. overnight. After cooling, 20 mL of water was added and the mixture was filtered, the filtrate made acidic with conc. HCl. The tan precipitate was filtered off and recrystallized from EtOH yielding 380 mg of tan solid (24%) which was identical to purchased material by LC/MS analysis. $^1$H NMR (300 MHz, DMSO) δ 13.60 (s, 1H), 10.51 (s, 1H), 8.41 (dd, J=1.9, 4.7, 1H), 8.27 (dd, J=1.9, 7.7, 1H), 7.78 (d, J=8.9, 2H), 7.36 (d, J=8.8, 2H), 6.91 (dd, J=4.8, 7.7, 1H). $^{13}$C NMR (75 MHz, DMSO) δ 168.91, 155.22, 152.51, 140.52, 138.65, 128.45, 125.49, 121.32, 114.22, 107.88. MS 247 (M-1).

Example 13: Synthesis of Compound C07 Enantiomers and ML390

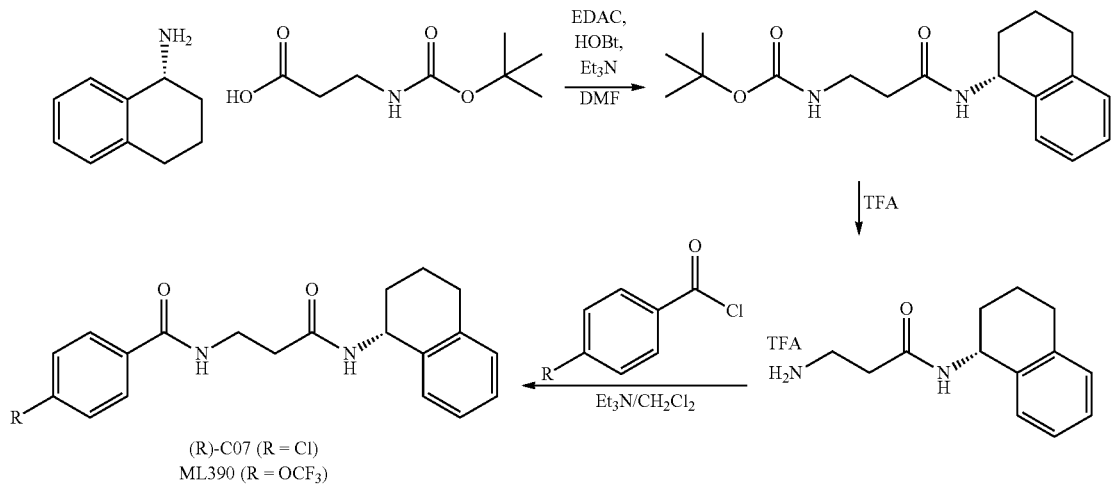

(R)-C07 (R = Cl)
ML390 (R = OCF$_3$)

To 2.00 g of (R)-1-amino-1,2,3,4-tetrahydronaphthalene (13.6 mmol) in 20 mL of DMF was added 2.58 g of N-tBOC-β-alanine (13.6 mmol), 14 mL of Et$_3$N (140 mmol), 1.84 g of HOBt (13.6 mmol) and 3.90 g of EDAC HCl (10.2 mmol) and the mixture was stirred overnight at room temperature. Water and CH$_2$Cl$_2$ were added and separated, the water was rinsed several times with CH$_2$Cl$_2$, the combined CH$_2$Cl$_2$ layers were rinsed several times with brine before drying (MgSO₄), filtering, and concentration, chasing the residual DMF off with toluene. Chromatography with 25-50% EtOAc in hexane yielded 3.58 g of product as a white solid (83%). $^1$H NMR (300 MHz, CDCl$_3$) δ 7.20-7.25 (m, 1H), 7.17 (t, J=3.5, 2H), 7.08-7.12 (m, 1H), 5.91 (d, J=6.5, 1H), 5.19 (t, J=6.8, 2H), 3.43 (q, J=6.1, 2H), 2.89-2.67 (m, 2H), 2.42 (t, J=5.9, 2H), 2.10-1.97 (m, 1H), 1.90-1.77 (m, 3H), 1.42 (s, 9H). $^{13}$C NMR (75 MHz, CDCl$_3$) δ 170.54, 156.04, 137.50, 136.56, 129.14, 128.55, 127.27, 126.25, 79.25, 47.42, 36.93, 36.45, 30.17, 29.18, 28.38, 19.97.

This material was dissolved in 150 mL of CH$_2$Cl$_2$ and cooled in an ice bath before addition of 40 mL of TFA and removing the ice bath. After stirring 2 h, the reaction was concentrated to an oil, addition of ether produced white solids which were filtered and rinsed with ether, 3.70 g (99%). $^1$H NMR (300 MHz, DMSO-d$_6$) δ 8.48 (d, J=8.5, 1H), 7.24-7.02 (m, 4H), 4.99 (dd, J=5.9, 13.7, 1H), 3.05 (s, 2H), 2.73 (d, J=5.9, 2H), 1.95-1.79 (m, 2H), 1.79-1.60 (m, 2H).

ML390: To 304 mg of the TFA salt (0.916 mmol) stirred in 10 mL of CH$_2$Cl$_2$ was added 280 mg of Et$_3$N (2.79 mmol), dissolving the solids, then 226 mg (1.01 mmol) of 4-trifluoromethoxy benzoyl chloride and the reaction was stirred overnight. Aqueous NaHCO$_3$ and CH$_2$Cl$_2$ were added and separated, the CH$_2$Cl$_2$ was dried, concentrated and chromatographed with 20-70% EtOAc in hexanes before recrystallization from CH$_2$Cl$_2$ and hexane which yielded 292 mg of product (78%). $^1$H NMR (300 MHz, DMSO-d$_6$) δ 8.70 (t, J=5.4, 1H), 8.30 (d, J=8.7, 1H), 7.97 (d, J=8.7, 2H), 7.47 (d, J=8.2, 2H), 7.15-7.01 (m, 3H), 7.01-6.91 (m, 1H), 4.99 (dd, J=5.8, 12.7, 1H), 3.52 (dd, J=6.5, 12.6, 2H), 2.79-2.61 (m, 2H), 2.40 (ddd, J=6.9, 14.2, 27.5, 2H), 1.94-1.75 (m, 2H), 1.75-1.54 (m, 2H). $^{19}$F NMR (282 MHz, CDCl$_3$) δ −57.71. $^{13}$C NMR (75 MHz, DMSO-d$_6$) δ 169.76, 164.92, 150.16, 137.50, 136.96, 133.58, 129.42, 128.58, 128.12, 126.51, 125.62, 120.50, 119.96 (q, J$_{C-F}$=5.4) 46.20, 36.36, 35.35, 29.85, 28.72, 19.92. HRMS: Calcd. for C$_{21}$H$_{21}$F$_3$N$_2$O$_3$ 407.1577 (M+H); found, 407.1578.

(R)-C07 was made using the same procedure but using 4-chlorobenzoyl chloride and isolated in 73% as a white solid: $^1$H NMR (300 MHz, DMSO) δ 8.67 (t, J=5.4, 1H), 8.31 (d, J=8.7, 1H), 7.87 (d, J=8.6, 2H), 7.54 (d, J=8.5, 2H), 7.12 (t, J=7.9, 2H), 7.08-6.95 (m, 2H), 5.00 (t, J=7.1, 1H), 3.52 (dd, J=6.6, 12.7, 2H), 2.70 (d, J=4.9, 2H), 2.48-2.41 (m, 1H), 2.37 (dd, J=6.8, 14.2, 1H), 1.85 (dd, J=3.7, 9.4, 2H), 1.77-1.57 (m, 2H). $^{13}$C NMR (75 MHz, DMSO) δ 169.68, 165.03, 137.49, 136.91, 135.82, 133.20, 129.00, 128.53, 128.20, 128.09, 126.49, 125.61, 46.14, 36.29, 35.32, 29.81, 28.69, 19.89. MS 357 (M+1).

Example 14: Synthesis of Brequinar

Briefly, Brequinar sodium was prepared according to that recited in U.S. Pat. No. 4,680,299. Utilizing a Pfitzinger reaction, 5-fluoroisatin was condensed with 4-(2-fluorophenyl)propiophenone in the presence of KOH to give Brequinar as the free acid which was recrystallized from DMF. Subsequent salt formation using sodium hydroxide gave Brequinar sodium in 47% over 2 steps. LC and quantitative $^1$H NMR spectroscopy studies found the purity of the salt to be >95%

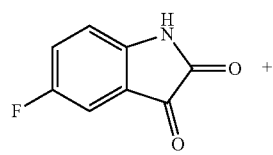

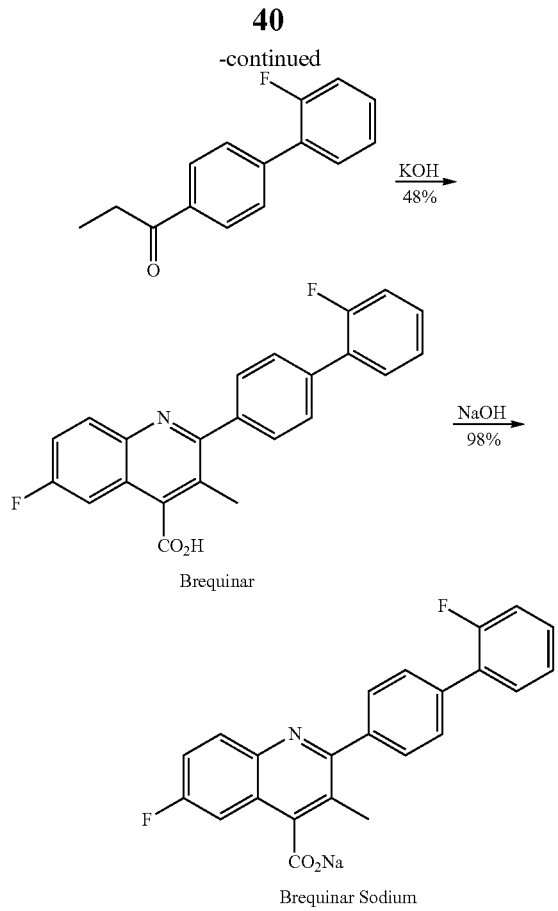

Brequinar

To a room temperature stirred solution of 5-fluoroisatin (18.1 g, 110 mmol, 1.00 eq.) and 4-(2-fluorophenyl)propiophenone (25.0 g, 110 mmol, 1.00 eq.) in absolute ethanol (183 mL, 0.60 M) was added dropwise, a 9.0 M aq. solution of potassium hydroxide (81.0 mL, 729 mmol, 6.66 eq.). The resulting mixture was heated at 100° C. for 24 h, cooled to room temperature and concentrated under reduced pressure. Water (500 mL) was added to the residue and extracted with Et$_2$O (500 mL). The aq. layer was then cooled to 0° C. and acidified with glacial acetic to give a cloudy solution. The precipitate was filtered and washed with water (100 mL) followed by Et$_2$O (100 mL) to give the crude product. The solid was recrystallized from hot DMF/water to give Brequinar as a white crystalline solid (19.9 g, 53.0 mmol, 48%). m.p. 314°-316°. $^1$H NMR (300 MHz, DMSO-d6) 14.4 (1H, s, COOH), 8.15 (1H, dd, J=9.0, 5.6 Hz, ArH), 7.77-7.67 (5H, m, ArH), 7.64 (1H, t, J=7.9 hz, ArH), 7.53-7.43 (2H, m, ArH), 7.40-7.30 (2H, m, ArH), 2.47 (3H, s, CCH$_3$); LRMS m/z (ESI$^+$) 376 ([M+H]$^+$, 100); LRMS m/z (ESI$^-$) 374 ([M−H]$^-$, 100), 749 ([2M−H]$^-$, 20).

Brequinar Sodium

To a room temperature stirred solution of Brequinar (18.1 g, 48.2 mmol, 1.00 eq.) in absolute ethanol (482 mL, 0.10 M) was added a 1.0 M aq. solution of sodium hydroxide (48.2 mL, 48.2 mmol, 1.00 eq.). The resulting mixture was heated at 50° C. for 4 h (until clear), filtered and concentrated under reduced pressure. The residue was lyophilized from water to give Brequinar sodium as a white powder (18.8 g, 47.3 mmol, 98%). $^1$H NMR (300 MHz, DMSO-$d_6$) 7.94 (1H, dd, J=9.0, 5.7 Hz, ArH), 7.69-7.66 (4H, m, ArH), 7.63 (1H, t, J=8.4 hz, ArH), 7.60-7.49 (2H, m, ArH), 7.49-7.41 (1H, m, ArH), 7.40-7.30 (2H, m, ArH), 2.36 (3H, s, CCH$_3$). LRMS m/z (ESI$^+$) 376 ([M+H]$^+$, 100); LRMS m/z (ESI$^-$) 374 ([M−H]$^-$, 100), 749 ([2M−H]$^-$, 15).

Example 15: Solubility Determination

Solubility was determined in phosphate buffered saline (PBS) pH 7.4 with 1% DMSO. Each compound was prepared in duplicate at 100 µM in both 100% DMSO and PBS with 1% DMSO. Compounds were allowed to equilibrate at room temperature with a 250 rpm orbital shake for 24 hours. After equilibration, samples were analyzed by UPLC-MS (Waters, Milford, Mass.) with compounds detected by SIR detection on a single quadrupole mass spectrometer. The DMSO samples were used to create a two point calibration curve to which the response in PBS was fit.

Example 16: PBS Stability

Stability was determined in the presence of PBS pH 7.4 with 0.1% DMSO. Each compound was prepared in duplicate on six separate plates and allowed to equilibrate at room temperature with a 250 rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

Example 17: GSH Stability

Stability was determined in the presence of PBS pH 7.4 µM and 50 µM glutathione with 0.1% DMSO. Each compound was prepared in duplicate on six separate plates and allowed to equilibrate at room temperature with a 250 rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

Example 18: Plasma Protein Binding

Plasma protein binding was determined by equilibrium dialysis using the Rapid Equilibrium Dialysis (RED) device (Pierce Biotechnology, Rockford, Ill.) for both human and mouse plasma. Each compound was prepared in duplicate at 5 µM in plasma (0.95% acetonitrile, 0.05% DMSO) and added to one side of the membrane (200 µl) with PBS pH 7.4 added to the other side (350 µl). Compounds were incubated at 37° C. for 5 hours with a 250 rpm orbital shake. After incubation, samples were analyzed by UPLC-MS (Waters, Milford, Mass.) with compounds detected by SIR detection on a single quadrupole mass spectrometer.

Example 19: Plasma Stability

Plasma stability was determined at 37° C. at 5 hours in both human and mouse plasma. Each compound was prepared in duplicate at 5 µM in plasma diluted 50/50 (v/v) with PBS pH 7.4 (0.95% acetonitrile, 0.05% DMSO). Compounds were incubated at 37° C. for 5 hours with a 250 rpm orbital shake with time points taken at 0 and 5 hours. Samples were analyzed by UPLC-MS (Waters, Milford, Mass.) with compounds detected by SIR detection on a single quadrupole mass spectrometer.

Example 20: Primary Screen to Identify Compounds that Promote Myeloid Differentiation The cell line used was ERHoxA9 myeloblast cell line. A conditional version of HoxA9 was generated by fusing it with the hormone binding domain of the estrogen receptor, such that HoxA9 is active only in the presence of estrogen. When introduced into primary murine bone marrow mononuclear cells by retroviral transduction, and cultured in the presence of stem cell factor (SCF) and beta-estradiol, the ERHoxA9 protein arrests myeloid differentiation, causing the outgrowth of myeloblast cell lines. These cell lines proliferate indefinitely in the presence of beta-estradiol and SCF. Removal of beta-estradiol from the culture media inactivates ERHoxA9 and the cells are freed from the HoxA9-differentiation arrest and undergo normal myeloid differentiation. The system was further adapted by generating cell lines using bone marrow harvested from transgenic mice in which green fluorescent protein (GFP) is inserted downstream of the endogenous lysozyme promoter. Lysozyme is a secondary granule protein, only expressed in differentiated myeloid cells. Thus, the ERHoxA9 myeloblast cell lines derived from the bone marrow of the LysozymeGFP transgenic mice were GFP negative in the presence of beta-estradiol but became brightly GFP-positive upon removal of beta-estradiol and inactivation of ERHoxA9.

Cells were cultured in RPMI (Cellgro) supplemented with 10% fetal bovine serum (Serum Source Int'l), penicillin/streptomycin, L-glutamine (Omega Scientific), 5% conditioned media containing stem cell factor (SCF), and 0.5 µM beta-estradiol (Sigma). On day 1, 25 µL of complete media supplemented with 0.04% Pluronic F-68 (GIBCO) was added to a sterile 384 well culture plate (Greiner) followed by the addition of 0.2 µL of test compound in DMSO (Sigma). Wells contained complete media supplemented with Pluronic F-68 and the 5 µM of the estrogen receptor antagonist fulvestrant that served as a positive control for differentiation. 25 µL of cells (1.2×10$^5$/ml) in complete media were added and the plates were incubated (37° C./5% CO$_2$) for 4 days. Final concentrations of components were 3,000 cells/well, 4 µM test compound, and 0.4% DMSO.

On day 5, plates were harvested as follows: 5 µL of an antibody/bead solution consisting of a 1:100 dilution of APC-conjugated anti-mouse CD11b (eBioscience, cloneM1/70) and a 1/500 dilution of polystyrene beads (Spherotech) were added to wells and the plates were incubated for 20 min prior to sampling using the HyperCyt® high throughput flow cytometry platform.

Detailed Assay Protocols for Example 20:
Propagation Media
450 mL of RPMI (Cellgro, VWR cat #45000-412), 50 mL fetal bovine serum (Serum Source International, cat #FB02-500HI), 5 mL penicillin/streptomycin/L-glutamine (Omega Scientific, cat #PG-30), 25 mL conditioned media containing stem cell factor (SCF) and 0.05 µM beta-estradiol (Sigma, cat #P5556).

Screening Media

Propagation media plus 0.04% Pluronic F-68 (Gibco, Life Technologies cat #24040-032).

Conditioned Media

Generated by a Chinese Hamster Ovary (CHO) cell line which constitutively expresses and secretes SCF into the supernatant.

Cell Propagation

ERHoxA9 myeloblast cell line is thawed and placed into a T175 flask with 100 mL of propagation media; incubated at 37° C., 5% $CO_2$. For passaging: cells are transferred to a 50 mL conical tube and spun at 1,500 rpm for 5 min; the old media is discarded; cells are washed with propagation media; and enough propagation media is added to make a 1:10 dilution.

Cell Screening

Cells are counted and transferred to a 50 mL conical tube. Cells are spun at 1,500 rpm for 5 min; old media is discarded. Pellets are resuspended in screening media to a concentration of $1.2 \times 10^5$ cells/mL.

384-well plate preparation: 25 µL of screening media are added to columns 1 and columns 3-24 of a sterile 384 well culture plate (Greiner, cat #781182); 0.2 µL of test compound in DMSO (Sigma, cat #D2650) are added into columns 3-23 using a pin tool; final concentration of compound is 4 µM with 0.4% DMSO; 25 µL of screening media containing 5 µM of fulvestrant (Sigma, cat #I4409) are added to wells in column 2 (positive control wells).

25 µL of cells ($1.2 \times 10^5$/ml) prepared as stated above are added to columns 2-23 (final concentration of cells is 3,000 cells/well). Plates are incubated for 4 days at 37° C. and 5% $CO_2$. On day 5, 5 µL of an antibody/bead solution consisting of a 1:100 dilution of APC-conjugated anti-mouse CD11b (eBioscience, cloneM1/70) and a 1:500 dilution of polystyrene beads (5 micron; Spherotech, cat #CPX-50-10) are added to wells in columns 2-23. Plates are incubated for 20 minutes.

Samples are read on the HyperCyt® high throughput flow cytometry platform. Cells of interest are gated using forward and side light scatter. GFP fluorescence is excited at 488 nm and detected with a 575/25 optical band pass filter. APC~αCD11b fluorescence is excited at 635 nm and detected with a 665/20 optical band pass filter.

Example 21: Primary Dose Response

Cells were cultured in RPMI (Cellgro) supplemented with 10% fetal bovine serum (Serum Source Int'l), penicillin/streptomycin, L-glutamine (Omega Scientific), 5% conditioned media containing stem cell factor (SCF), and 0.5 µM beta-estradiol (Sigma, E2758). On day 1, 25 µL of complete media supplemented with 0.04% Pluronic F-68 (GIBCO) was added to a sterile 384 well culture plate (Greiner) followed by the addition of 0.2 µL of compound dilution arrays in DMSO. Some wells contained complete media supplemented with Pluronic F-68 and 5 µM of the estrogen receptor antagonist fulvestrant that served as a positive control for differentiation. 25 µL of cells ($1.2 \times 10^5$/ml) in complete media were added and the plates were incubated (37° C./5% $CO_2$) for 4 days. Final concentrations of components were 3,000 cells/well and 0.4% DMSO. Test compounds were serially diluted 1:3 six times starting at 40 µM, resulting in a concentration range of 40 µM to 6 nM. The resultant data points were fitted by Prism® software (GraphPad Software Inc., San Diego, Calif.) using nonlinear least-squares regression in a sigmoidal dose-response model with variable slope, also known as the 4-parameter logistic equation. Curve fit statistics were used to determine the concentration of test compound that resulted in 50% of the maximal effect ($EC_{50}$), the confidence interval of the $EC_{50}$ estimate, the Hill slope, and the correlation coefficient.

On day 5, plates were harvested as follows: 5 µL of an antibody/bead solution consisting of a 1:100 dilution of APC-conjugated anti-mouse CD11b (eBioscience, cloneM1/70) and a 1/500 dilution of polystyrene beads (Spherotech) were added, and the plates were incubated for 20 min prior to sampling using the HyperCyt® high throughput flow cytometry platform. Cell viability and green fluorescence was stable for 24 h after the day 4 incubation. Gating on the inert bead population provided a measure of sampling quality, as the same number of beads are seeded into each well. The percent of GFP and APC positive live cells was used to determine whether the test compound has a differentiating effect.

Detailed Assay Protocols for Example 21:

Propagation Media 450 mL of RPMI (Cellgro, VWR cat #45000-412), 50 mL fetal bovine serum (Serum Source International, cat #FB02-500HI), 5 mL penicillin/streptomycin/L-glutamine (Omega Scientific, cat #PG-30).

Screening Media

Propagation media plus 0.04% Pluronic F-68 (Gibco, Life Technologies cat #24040-032).

Cell Propagation

Cells are thawed and placed into a T175 flask with 100 mL of propagation media, and incubated at 37° C., 5% $CO_2$. For passaging: cells are transferred to a 50 mL conical tube, and spun at 1,500 rpm for 5 minutes; the old media is discarded; cells are washed with propagation media; and enough propagation media is added to make a 1:10 dilution.

Cell Screening

Cells are counted and transferred to a 50 mL conical tube; spun at 1500 rpm for 5 minutes. old media is discarded, and pellets are resuspended in screening media to a concentration of $1.2 \times 10^5$ cells/mL.

96-well plate preparation: 100 µL of screening media is added to columns 1 and columns 3-24 of a sterile 96-well culture plate (Greiner, cat #655161); 0.8 µL of test compound in DMSO (Sigma, cat #D2650) are added into columns 3-23 using a pin tool; final concentration of compound is 4 µM with 0.4% DMSO. 100 µL of screening media containing 5 µM of fulvestrant (Sigma, cat #I4409) are added to wells in column 2 (positive control wells).

100 µL of cells ($1.2 \times 10^5$/ml) as prepared above are added to columns 2-23. Final concentration of cells is 12,000 cells/well. Plates are incubated for 4 days at 37° C. and 5% $CO_2$. On day 5, 20 µL of an antibody/bead solution consisting of a 1:100 dilution of APC-conjugated anti-mouse CD11b (eBioscience, cloneM1/70) and a 1:500 dilution of polystyrene beads (5 micron; Spherotech, cat #CPX-50-10) are added to wells in columns 2-23. Plates are incubated for 20 minutes.

Samples are read on the HyperCyt® high throughput flow cytometry platform. Cells of interest are gated using forward and side light scatter. APC~αCD11b (MAC1) fluorescence is excited at 635 nm and detected with a 665/20 optical band pass filter.

Example 22: Counterscreen Assay

The counterscreen assay was run to eliminate compounds that do not act on target of interest. Fluorescent compounds were identified and discarded by assaying for green or red fluorescence. Murine cells immortalized by HoxA9/Meis1, and lacking the GFP-reporter, were cultured in the same fashion as described above for the cells in the primary screen using RPMI (Cellgro) supplemented with 10% fetal bovine serum (Serum Source Int'l), penicillin/streptomycin, L-glutamine (Omega Scientific). On day 1, 25 µL of complete media supplemented with 0.04% Pluronic F-68 (GIBCO) was added to sterile 384 well culture plate (Greiner) followed by the addition of 0.2 µL of test compound in DMSO. 25 µL of cells ($1.2 \times 10^5$/ml) in complete media were added and the plates were incubated (37° C./5% $CO_2$) for 24 h. Final concentrations of components were 3,000 cells/well, 4 uM test compound, and 0.4% DMSO. After 24 h incubation plates were harvested using the HyperCyt® platform and cells of interest were gated using forward and side light scatter. Green fluorescence was excited at 488 nm and detected with a 575/25 optical band pass filter. Red fluorescence was excited at 635 nm and detected with a 665/20 optical band pass filter. Wells that were scored as fluorescent in either emission channel were flagged as auto-fluorescent, either a result of the compound's intrinsic fluorescence, or the ability of the cell to metabolize a non-fluorescent compound into a fluorescent compound.

Example 23: Differentiation Confirmatory Screen

Data for MAC1 expression was extracted from the primary screen data set.

Example 24: Cellular Toxicity Counterscreen

Promega CellTiter-Glo(R) Assay was utilized to measure ATP (as a surrogate for viability) in the fibroblast cell line NIH 3T3 as a measure of cellular viability. Opaque-walled multiwell plates with mammalian cells in culture medium, 100 µL per well for 96-well plates or 25 mL per well for 384-well plates were prepared. After background luminescence was obtained, the test compounds were added and incubated according to culture protocol. After 30 min, a volume of CellTiter-Glo(R) Reagent equal to the volume of cell culture medium present in each well, the contents were mixed 2 min on an orbital shaker, incubated for 10 min before recording luminescence for 200 msec.

Example 25: Estrogen Receptor Artifact Counterscreen

The wild-type HoxA9 myeloblast cell line was used within the same procedure as in the primary assay, except using wild-type HoxA9 (i.e., the constitutively active HoxA9 protein lacking the estrogen-receptor fusion) cell line and on day 4, a MAC1-APC antibody was added.

Example 26: HoxA9 Cytotoxicity Panel

HoxA9: Human Leukemic Cells

The THP-1 and U937 human leukemic cell lines were used within the same procedure as in the primary assay, except using human leukemic cell lines. These are factor-independent cell lines and estrogen-independent cell lines, such that cells were grown simply in RPMI supplemented with 10% fetal bovine serum.

The cytotoxicity assay used HEK293T, HepG2 and A549 cells obtained from ATCC to test for cytotoxicity at a range of concentrations (0.05-26 uM). Compounds were added to cells and incubated for 72 h. Cellular ATP levels were measured as a surrogate for cell viability using the luminescence reagent, CellTiter-Glo (Promega).

Detailed Assay Protocol for HEK293:

Day 0: HEK293 cells (HEK293T, ATCC) grown in Triple flask (NUNC) to ~95% confluence (TrypLE Phenol Red free) and resuspended for dispensing at 50,000 cells/mL of DMEM, 10% FBS/Pen/Strep/L-Glutamine (Compact SelecT).

Day 1: Cells @2000 per well are plated in 40 µL media (DMEM/10% FBS/Pen/Strep/L-Glutamine) using Corning 8867BC 384 well plates; and incubated in standard TC conditions (5% $CO_2$; 95% humidity, 37° C.) for 24 h (Compact SelecT).

Day 2: 100 nL compound per well at dose are added 40 uL assay volume using a pin tool (CyBi Well). 100 nL cytotoxic compounds, Mitoxandrone (CID 4212) are pinned to positive control wells to a final concentration of 10 µM (100 nL 4 mM DMSO stock). System is incubated for 72 hours at 37° C. in Liconic incubator, 95% humidity 5% $CO_2$.

Day 4: Plate is removed from incubator to cool for 15 minutes to room temperature; 20 µL 50% Promega CellTiterGlo (diluted 1:1 with PBS, pH 7.4) are added with Thermo Combi. System is incubated at RT for 5 minutes.

Readings are obtained with Perkin-Elmer EnVision with US LUM settings for 0.1 sec per well.

Detailed Assay Protocol for HepG2:

Day 0: HepG2 cells (ATCC) are grown in Triple flasks (NUNC) to ~95% confluence (TrypLE Phenol Red free) and resuspended for dispensing at 50,000 cells/mL of DMEM, 10% FBS/Pen/Strep/L-Glutamine (using the TAP Compact SelecT automated c11 culture system).

Day 1: Cells @2000 per well are plated in 40 µL media (DMEM/10% FBS/Pen/Strep/L-Glutamine) using Corning 8867BC 384 well plates; and incubated in standard TC conditions (5% $CO_2$; 95% humidity, 37° C.) for 24 hours (Compact SelecT).

Day 2: 100 nL compound per well at dose is added into 40 uL assay volume using a pin tool (CyBi Well). 100 nL cytotoxic compounds, mitoxantrone are pinned in positive control wells to a final concentration of 10 µM (100 nL 4 mM DMSO stock). System is incubated for 72 h at 37° C. in Liconic incubator, 95% humidity 5% $CO_2$.

Day 4: Plate is removed from incubator, cooled for 15 min to room temperature; 20 µL 50% Promega CellTiter-Glo (diluted 1:1 with PBS, pH 7.4) is added with Thermo Combi. System is incubated at RT for 5 min.

Plates are read on a Perkin-Elmer EnVision plate reader with standard luminescence settings for 0.1 sec per well.

Detailed Assay Protocol for A549:

Day 0: A549 cells (ATCC) are grown in a Triple flask (NUNC) to ~95% confluence (TrypLE Phenol Red free) and resuspended for dispensing at 25,000 cells/mL of DMEM, 10% FBS/Pen/Strep/L-Glutamine (using the TAP Compact SelecT automated cell culture system).

Day 1: Cells at 1000 per well are plated in 40 uL media (DMEM/10% FBS/Pen/Strep/L-Glutamine) using Corning 8867BC 384 well plates; system is incubated in standard TC conditions (5% $CO_2$; 95% humidity, 37° C.) for 24 hours (Compact SelecT).

Day 2: 100 nL compound per well at dose are added into 40 uL assay volume using a pin tool (CyBi Well). 100 nL cytotoxic compounds, mitoxantrone (CID 4212) are pinned to positive control wells to a final concentration of 10 uM (100 nL 4 mM DMSO stock). System is incubated for 72 hours at 37° C. in Liconic incubator, 95% humidity 5% $CO_2$.

Day 4: Plate is removed from incubator, cooled for 15 minutes to room temperature; 20 µL 50% Promega CellTiterGlo (diluted 1:1 with PBS, pH 7.4) are added with Thermo Combi. System is incubated at room temperature for 5 minutes.

Plates are read on Perkin-Elmer EnVision with standard luminescence settings for 0.1 sec per well.

Example 27: HoxA9: CD34+ Counter Screen

CD34+ human primary cells were used within the same procedure as in the primary assay except using primary CD34+ cells. Cells were isolated using magnetic bead positive selection (Stem Cell Technologies) from the discarded bone marrow filters from normal human bone marrow donors. In this case, the cells were cultured in RPMI supplemented with 10% fetal bovine serum, 50 uM beta-mercaptoethanol, as well as 10 ng/ml stem cell factor, interlukin-3, interlukin-6, thrombopoeitin, and flt-3-ligand.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating a hematological cancer in a subject in need thereof, the method comprising administering to the subject a therapeutically effective amount of a dihydroorotate dehydrogenase (DHODH) inhibitor, wherein the dihydroorotate inhibitor is selected from the group consisting of 6-fluoro-2-(2'-fluoro-[1,1'-biphenyl]-4-yl)-3-methylquinoline-4-carboxylic acid; salts, or solvates thereof; wherein said DHODH inhibitor is administered to the subject with a frequency less than or equal to once every 48 hours; wherein said administration results in intermittent periods of nucleotide depletion that differentially starves malignant cells as compared to normal cells; and wherein the 6-fluoro-2-(2'-fluoro-[1,1'-biphenyl]-4-yl)-3-methylquinoline-4-carboxylic acid is administered to the subject by injection.

2. The method according to claim 1, wherein 6-fluoro-2-(2'-fluoro-[1,1'-biphenyl]-4-yl)-3-methylquinoline-4-carboxylic acid or a salt or solvate thereof is administered to the subject with a frequency less than or equal to once every 72 hours.

3. The method according to claim 1, wherein the hematological cancer comprises acute myeloid leukemia (AML), acute promyelocytic leukemia (APL), mixed-lineage leukemia (MLL), myelodysplastic syndrome (MDS), and/or chronic myeloid leukemia (CML).

4. The method according to claim 3, wherein the hematological cancer comprises AML.

5. The method according to claim 1, wherein the subject has been treated or is being treated for a hematological cancer characterized by differentiation arrest.

6. The method according to claim 1, wherein 6-fluoro-2-(2'-fluoro-[1,1'-biphenyl]-4-yl)-3-methylquinoline-4-carboxylic acid is administered to the subject by an injection route selected from intravenous, intradermal, intramuscular, subcutaneous, intracutaneous, intrauterine, epidural and intracerebroventricular injections.

7. The method according to claim 1, wherein at least one additional agent useful for treating a hematological cancer is further administered to the subject.

8. The method according to claim 7, wherein the additional agent is arsenic trioxide.

9. The method according claim 1, wherein the subject is not responsive to one or more anticancer agents.

10. The method according to claim 1, wherein the method comprises administering to the subject a composition comprising a dihydroorotate dehydrogenase (DHODH) inhibitor in an amount and for a duration sufficient to increase levels of dihydroorotate and/or to reduce levels of uridine in a biological sample obtained from the subject, thereby treating the hematological cancer.

* * * * *